US012637720B2

(12) United States Patent
Gay et al.

(10) Patent No.: US 12,637,720 B2
(45) Date of Patent: May 26, 2026

(54) MOLECULAR SUBTYPING OF SMALL CELL LUNG CANCER TO PREDICT THERAPEUTIC RESPONSES

(71) Applicant: Board of Regents, The University of Texas System, Austin, TX (US)

(72) Inventors: Carl M. Gay, Houston, TX (US); Lauren A. Byers, Houston, TX (US); John V. Heymach, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 18/344,010

(22) Filed: Jun. 29, 2023

(65) Prior Publication Data

US 2024/0011103 A1     Jan. 11, 2024

Related U.S. Application Data

(62) Division of application No. 17/011,519, filed on Sep. 3, 2020, now Pat. No. 11,732,306.

(60) Provisional application No. 62/895,322, filed on Sep. 3, 2019.

(51) Int. Cl.
    *C12Q 1/6886* (2018.01)

(52) U.S. Cl.
    CPC ...... *C12Q 1/6886* (2013.01); *C12Q 2600/112* (2013.01); *C12Q 2600/154* (2013.01)

(58) Field of Classification Search
    None
    See application file for complete search history.

(56) References Cited

U.S. PATENT DOCUMENTS

2009/0269772 A1* 10/2009 Califano ................. G16B 5/20
707/E17.014

OTHER PUBLICATIONS

Cobb et al (Crit Care Med 2002 vol. 30 p. 2711) (Year: 2002).*
Stewart et al. (Oncotarget 2017 vol. 8 p. 28575) (Year: 2017).*
Mollaoglu et al. (Cancer Cell 2017 vol. 31 p. 270-285) (Year: 2017).*
Antonia et al., "Nivolumab alone and nivolumab plus ipilimumab in recurrent small-cell lung cancer (CheckMate 032): a multicentre, open-label, phase 1/2 trial," *Lancet Oncol*, 17:883-895, 2016.
Augustyn et al., "ASCL1 is a lineage oncogene providing therapeutic targets for high-grade neuroendocrine lung cancers," *PNAS*, 111(41):14788-14793, 2014.
Ayers et al., "IFN-gamma-related mRNA profile predicts clinical response to PD-1 blockade," *J Clin Invest*, 127:2930-2940, 2017.
Baine et al., "SCLC Subtypes Defined by ASCL1, NEUROD1, POU2F3, and YAP1: A Comprehensive Immunohistochemical and Histopathologic Characterization," *J Thorac Oncol*, 15:1823-1835, 2020.
Bonnafous et al., "Targeting MICA with therapeutic antibodies for the treatment of cancer," *Journal for ImmunoTherapy of Cancer*, 1(Suppl 1):P41, 2013.
Borromeo et al., "ASCL1 and NEUROD1 reveal heterogeneity in pulmonary neuroendocrine tumors and regulate distinct genetic programs," *Cell Reports*, 16:1259-1272, 2016.
Böttger et al., "Tumor Heterogeneity Underlies Differential Cisplatin Sensitivity in Mouse Models of Small-Cell Lung Cancer," *Cell Rep*, 27:3345-3358, 2019.
Butler et al., "Integrating single-cell transcriptomic data across different conditions, technologies, and species," *Nat Biotechnol*, 36:411-420, 2018.
Byers and Rudin, "Small cell lung cancer: where do we go from here?" *Cancer*, 121:664-672, 2015.
Byers et al., "An epithelial-mesenchymal transition gene signature predicts resistance to EGFR and PI3K inhibitors and identifies Axl as a therapeutic target for overcoming EGFR inhibitor resistance," *Clin Cancer Res*, 19:279-290, 2013.
Byers et al., "Proteomic profiling identifies dysregulated pathways in small cell lung cancer and novel therapeutic targets including PARP1," *Cancer Discov*, 2:798-811, 2012.
Cañadas et al., "Tumor innate immunity primed by specific interferon-stimulated endogenous retroviruses," *Nat Med*, 24:1143-1150, 2018.
Cardnell et al., "Protein expression of TTF1 and cMYC define distinct molecular subgroups of small cell lung cancer with unique vulnerabilities to aurora kinase inhibition, DLL3 targeting, and other targeted therapies," *Oncotarget*, 8:73419-73432, 2017.
Carney et al., "Establishment and identification of small cell lung cancer cell lines having classic and variant features," *Cancer Res*, 45:2913-2923, 1985.
Chalishazar et al., "MYC-Driven Small-Cell Lung Cancer is Metabolically Distinct and Vulnerable to Arginine Depletion," *Clin Cancer Res*, 25:5107-5121, 2019.
Chung et al., "Pembrolizumab After Two or More Lines of Previous Therapy in Patients With Recurrent or Metastatic SCLC: Results From the KEYNOTE-028 and KEYNOTE-158 Studies," *J Thorac Oncol*, 15:618-627, 2020.
Chung et al., "Phase 2 study of pembrolizumab in advanced small-cell lung cancer (SCLC): KEYNOTE-158.," Abstract 8506, ASCO Annual Meeting, 2018.
Cobb, J. P. et al., "Sepsis gene expression profiling: Murine splenic compared with hepatic responses determined by using complementary DNA microarrays," *Crit Care Med*, 30 (2002): 2711-2721.
Das, "Labetuzumab govitecan in metastatic colorectal cancer," *Lancet Oncol*, 18:e563, 2017.
Dotan et al., "Phase I/II Trial of Labetuzumab Govitecan (Anti-CEACAM5/SN-38 Antibody-Drug Conjugate) in Patients With Refractory or Relapsing Metastatic Colorectal Cancer," *J Clin Oncol*, 35:3338-3346, 2017.

(Continued)

*Primary Examiner* — Katherine D Salmon
(74) *Attorney, Agent, or Firm* — pH IP Law

(57) ABSTRACT

Provided herein are methods for determining a subtype of a small cell lung cancer in a patient based on the express status of ASCL1, NEUROD1, and POU2F3, which are expressed in a mutually exclusive fashion. The subtype of the cancer can be used to determine the sensitivity of the cancer to certain anti-cancer therapies. As such, also provided are methods of treating patients having small cell lung cancer based on the subtyping results.

9 Claims, 28 Drawing Sheets
(25 of 28 Drawing Sheet(s) Filed in Color)

(56)                    References Cited

OTHER PUBLICATIONS

Farago et al., "Combination Olaparib and Temozolomide in Relapsed Small Cell Lung Cancer," *Cancer Discov*, 9(10):1372-1387, 2019.

Fiegl et al., "Methylated NEUROD1 promoter is a marker for chemosensitivity in breast cancer," *Clin Cancer Res*, 14:3494-3502, 2008.

Gay et al., "ASCL1, NEUROD1, and POU2F3 Drive Distinct Subtypes of Small Cell Lung Cancer with Unique Therapeutic Vulnerabilities," *Oral Abstract Sessions, Journal of Thoracic Oncology*, Abstract OA03.06, 14(10 Supplement):S213, 2019.

Gay et al., "Differential Sensitivity Analysis for Resistant Malignancies (DISARM) Identifies Common Candidate Therapies across Platinum-Resistant Cancers," *Clin Cancer Res*, 25:346-357, 2019.

Gay et al., "Inter- and intra-tumoral variations in ASCL1, NEUROD1, and POU2F3 transcriptional programs underlie three distinct molecular subtypes of small cell lung cancers," In: Proceedings of the American Association for Cancer Research Annual Meeting, *Cancer Res*, 79(13 Supplement):Abstract No. 3772, 2019.

Gay et al., "Inter- and intra-tumoral variations in ASCL1, NEUROD1, and POU2F3 transcriptional programs underlie three distinct molecular subtypes of small cell lung cancers," Poster, American Association for Cancer Research Annual Meeting , Abstract No. 3772, 2019.

Gay et al., "Patterns of transcription factor programs and immune pathway activation define four major subtypes of SCLC with distinct therapeutic vulnerabilities," *Cancer Cell*, 39:346-360, 2021.

Gazdar et al., "Characterization of variant subclasses of cell lines derived from small cell lung cancer having distinctive biochemical, morphological, and growth properties," *Cancer Res*, 45:2924-2930, 1985.

George et al., "Comprehensive genomic profiles of small cell lung cancer," *Nature*, 524:47-53, 2015.

Hamilton et al., "Immunotherapy for small cell lung cancer: mechanisms of resistance," *Expert Opin Biol Ther*, 19:423-432, 2019.

Hellmann et al., "Tumor Mutational Burden and Efficacy of Nivolumab Monotherapy and in Combination with Ipilimumab in Small-Cell Lung Cancer," *Cancer Cell*, 33:853-861 e854, 2018.

Hodgkinson et al., "Tumorigenicity and genetic profiling of circulating tumor cells in small-cell lung cancer," *Nat Med*, 20:897-903, 2014.

Horn et al., "First-Line Atezolizumab plus Chemotherapy in Extensive-Stage Small-Cell Lung Cancer," *N Engl J Med*, 379:2220-2229, 2018.

Huang et al., "POU2F3 is a master regulator of a tuft cell-like variant of small cell lung cancer," *Genes & Development*, 32:915-928, 2018.

Ireland et al., "MYC Drives Temporal Evolution of Small Cell Lung Cancer Subtypes by Reprogramming Neuroendocrine Fate," *Cancer Cell*, 38(1):60-78, 2020.

Kitajima et al., "Suppression of STING Associated with LKB1 Loss in KRAS-Driven Lung Cancer," *Cancer Discov*, 9:34-45, 2019.

Lim et al., "Intratumoural heterogeneity generated by Notch signalling promotes small- cell lung cancer," *Nature*, 545:360-364, 2017.

Lin et al., "Genes suppressed by DNA methylation in non-small cell lung cancer reveal the epigenetics of epithelial-mesenchymal transition," *BMC Genomics*, 15:1079, 2014.

Lochmann et al., "Venetoclax Is Effective in Small-Cell Lung Cancers with High BCL-2 Expression," *Clin Cancer Res*, 24:360-369, 2018.

Lok et al., "PARP Inhibitor Activity Correlates with SLFN11 Expression and Demonstrates Synergy with Temozolomide in Small Cell Lung Cancer," *Clin Cancer Res*, 23:523-535, 2017.

Mak et al., "A Patient-Derived, Pan-Cancer EMT Signature Identifies Global Molecular Alterations and Immune Target Enrichment Following Epithelial-to-Mesenchymal Transition," *Clin Cancer Res*, 22:609-620, 2016.

Mollaoglu et al., "MYC drives progression of small cell lung cancer to a variant neuroendocrine subtype with vulnerability to aurora kinase inhibition," *Cancer Cell*, 31:270-285, 2017.

Murai et al., "Resistance to PARP inhibitors by SLFN11 inactivation can be overcome by ATR inhibition," *Oncotarget*, 7:76534-76550, 2016.

Ott et al., "T-Cell-Inflamed Gene-Expression Profile, Programmed Death Ligand 1 Expression, and Tumor Mutational Burden Predict Efficacy in Patients Treated With Pembrolizumab Across 20 Cancers: KEYNOTE-028," *J Clin Oncol*, 37:318-327, 2019.

Owonikoko et al., "OA05.05 Randomized Phase 2 Study: Alisertib (MLN8237) or Placebo + Paclitaxel as Second-Line Therapy for Small-Cell Lung Cancer (SCLC)," *Journal of Thoracic Oncology*, 12:S261-S262, 2017.

Pantelidou et al., "PARP Inhibitor Efficacy Depends on CD8(+) T-cell Recruitment via Intratumoral STING Pathway Activation in BRCA-Deficient Models of Triple-Negative Breast Cancer," *Cancer Discov*, 9:722-737, 2019.

Parkes et al., "Activation of STING-Dependent Innate Immune Signaling By S-Phase-Specific DNA Damage in Breast Cancer," *J Natl Cancer Inst*, 109(1):djw199, 2017.

Paz-Ares et al., "Durvalumab plus platinum-etoposide versus platinum-etoposide in first-line treatment of extensive-stage small-cell lung cancer (CASPIAN): a randomised, controlled, open-label, phase 3 trial," *Lancet*, 394:1929-1939, 2019.

Pietanza et al., "Randomized, Double-Blind, Phase II Study of Temozolomide in Combination With Either Veliparib or Placebo in Patients With Relapsed-Sensitive or Refractory Small-Cell Lung Cancer," *J Clin Oncol*, 36:2386-2394, 2018.

Polley et al., "Small Cell Lung Cancer Screen of Oncology Drugs, Investigational Agents, and Gene and microRNA Expression," *J Natl Cancer Inst*, 108:djw122, 2016.

Reck et al., "Efficacy and safety of nivolumab (nivo) monotherapy versus chemotherapy (chemo) in recurrent small cell lung cancer (SCLC): Results from CheckMate 331," *Annals of Oncology*, 29(suppl_10):x39-x43, 2018.

Rudin et al., "Molecular subtypes of small cell lung cancer: a synthesis of human and mouse model data," *Nature Reviews Cancer*, 19(5):289-297, 2019.

Rudin et al., "Rovalpituzumab tesirine, a DLL3-targeted antibody-drug conjugate, in recurrent small-cell lung cancer: a first-in-human, first-in-class, open-label, phase 1 study," *Lancet Oncol*, 18:42-51, 2017.

Sato et al., "PRC2 overexpression and PRC2-target gene repression relating to poorer prognosis in small cell lung cancer," *Sci Rep*, 3:1911, 2013.

Sen et al., "Targeting DNA damage repair in small cell lung cancer and the biomarker landscape," *Transl Lung Cancer Res*, 7:50-68, 2018.

Sharkey et al., "Selective and Concentrated Accretion of SN-38 with a CEACAM5-Targeting Antibody-Drug Conjugate (ADC), Labetuzumab Govitecan (IMMU-130)," *Mol Cancer Ther*, 17:196-203, 2018.

Simpson et al., "A biobank of small cell lung cancer CDX models elucidates inter- and intratumoral phenotypic heterogeneity," *Nature Cancer*, 1:437-451, 2020.

Skoulidis et al., "Co-occurring genomic alterations define major subsets of KRAS-mutant lung adenocarcinoma with distinct biology, immune profiles, and therapeutic vulnerabilities," *Cancer Discov*, 5:860-877, 2015.

Stewart et al., "Dynamic variations in epithelial-to-mesenchymal transition (EMT), ATM, and SLFN11 govern response to PARP inhibitors and cisplatin in small cell lung cancer," *Oncotarget*, 8:28575-28587, 2017.

Stewart et al., "Single-cell analyses reveal increasing intratumoral heterogeneity as an essential component of treatment resistance in small cell lung cancer," AACR Annual Meeting, *Cancer Res*, 79(13 Suppl): Abstract 2899, 2019.

Stewart et al., "Single-cell profiling of small cell lung cancer circulating tumor cell-derived xenograft models reveals intratumoral heterogeneity among mediators of chemoresistance," AACR Annual Meeting, *Cancer Res*, 78(13 Suppl):Abstract 990, 2018.

Thistlethwaite et al., "The clinical efficacy of first-generation carcinoembryonic antigen (CEACAM5)-specific CAR T cells is

(56)          References Cited

OTHER PUBLICATIONS limited by poor persistence and transient pre-conditioning-dependent respiratory toxicity," *Cancer Immunol Immunother*, 66:1425-1436, 2017.

Truong et al., "Hypermethylation of adjacent CpG sites is negatively correlated with the expression of lineage oncogene ASCL1 in pulmonary neuroendocrine tumors," *Tumour Biol*, 39:1010428317706225, 2017.

Whalen et al., "Targeting the Somatostatin Receptor 2 with the Miniaturized Drug Conjugate, PEN-221: A Potent and Novel Therapeutic for the Treatment of Small Cell Lung Cancer," *Mol Cancer Ther*, 18:1926-1936, 2019.

White et al., "Discovery of an SSTR2-Targeting Maytansinoid Conjugate (PEN-221) with Potent Activity in Vitro and in Vivo," *J Med Chem*, 62:2708-2719, 2019.

Zhang et al., "Small cell lung cancer tumors and preclinical models display heterogeneity of neuroendocrine phenotypes," *Transl Lung Cancer Res*, 7:32-49, 2018.

Zimmermann et al., "Immune Checkpoint Inhibitors in the Management of Lung Cancer," *Am Soc Clin Oncol Educ Book*, 38:682-695, 2018.

* cited by examiner

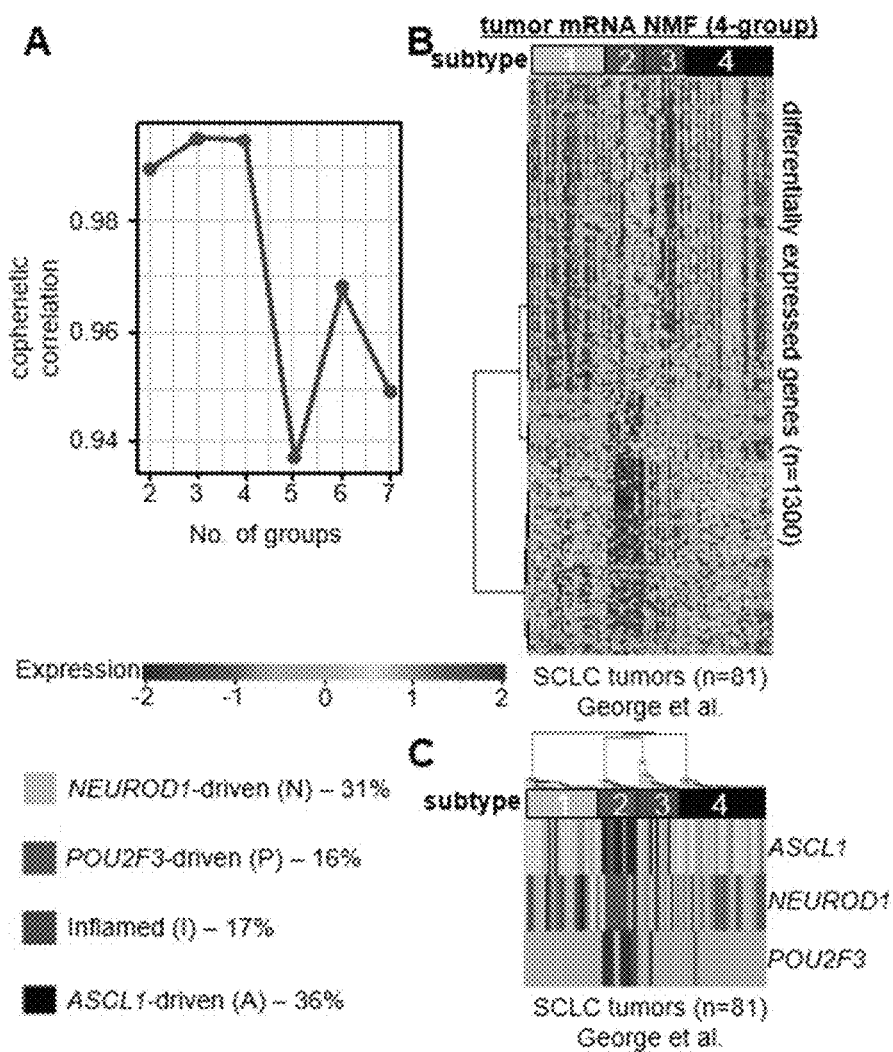
FIGS. 1A-C

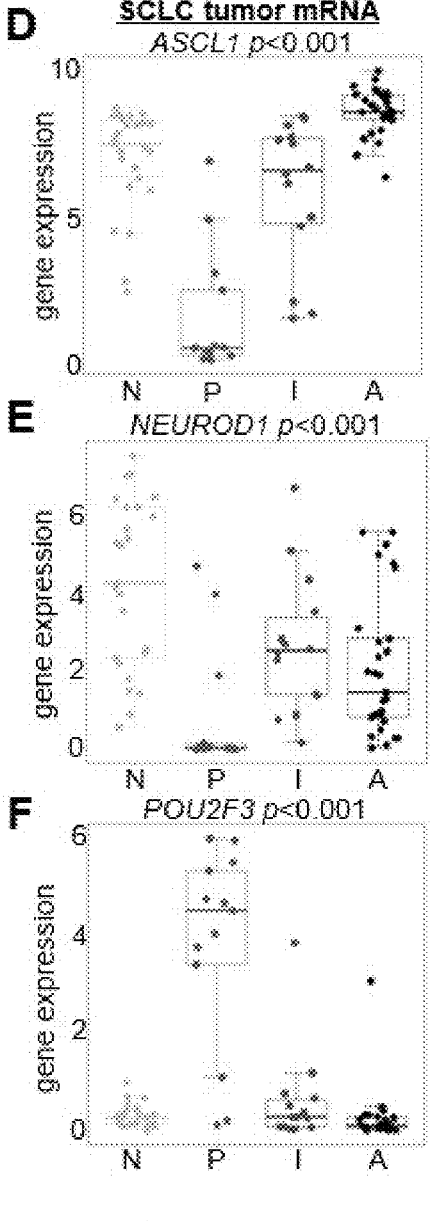
FIGS. 1D-F

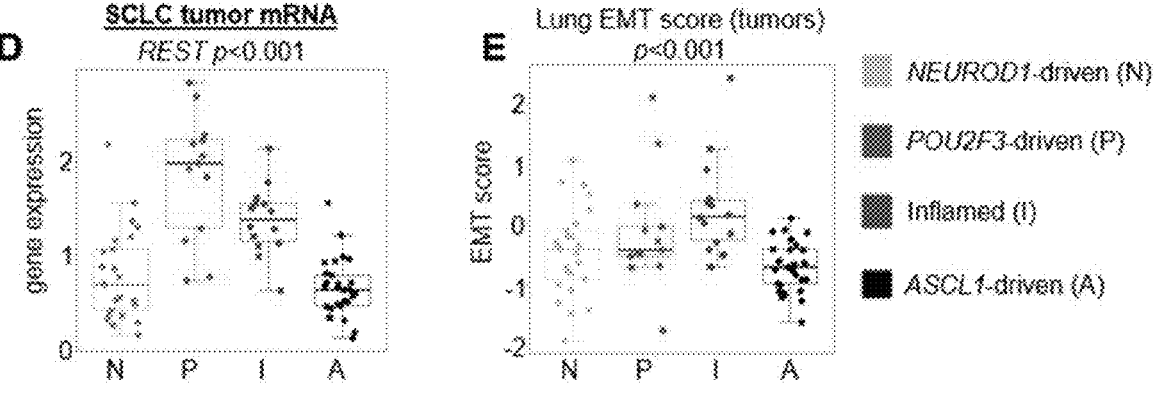
FIGS. 2D-E
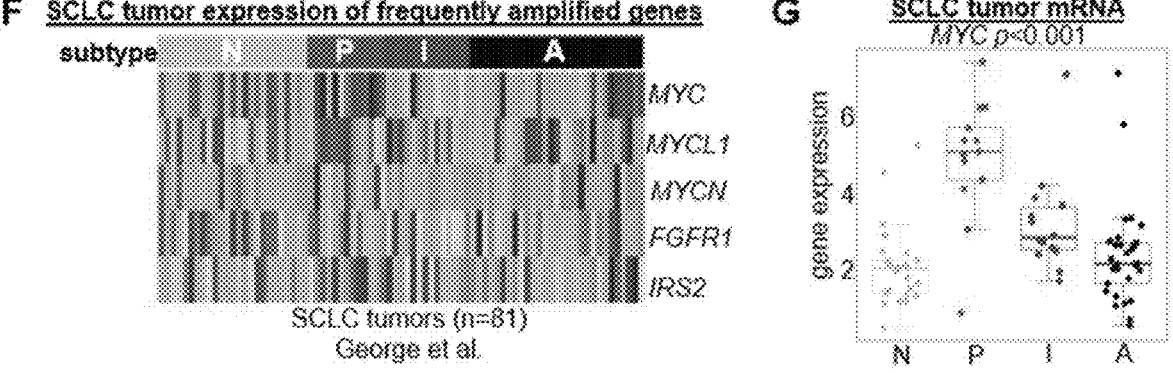
FIGS. 2F-G
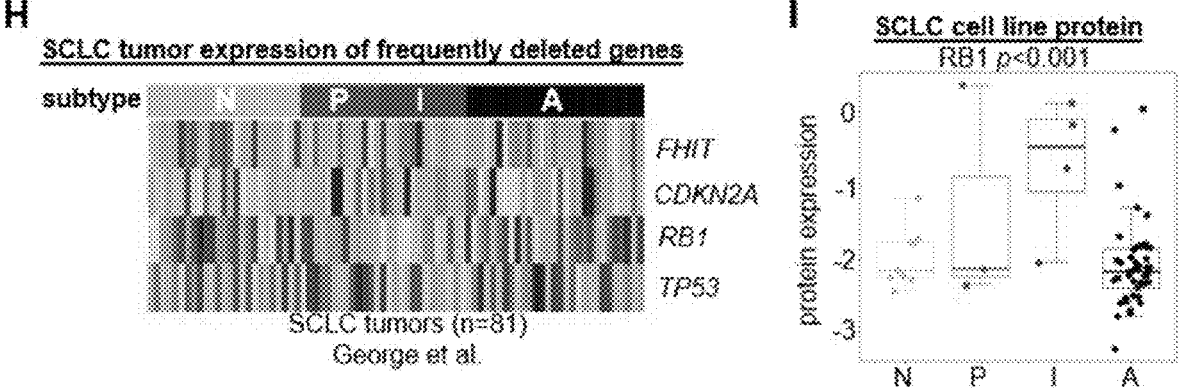
FIGS. 2H-I

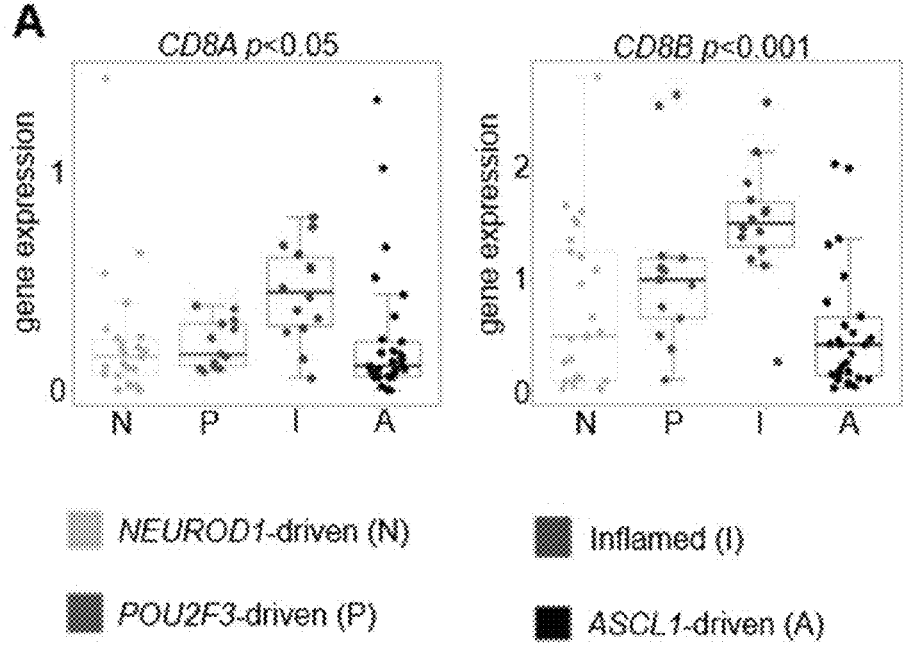
FIG. 3A
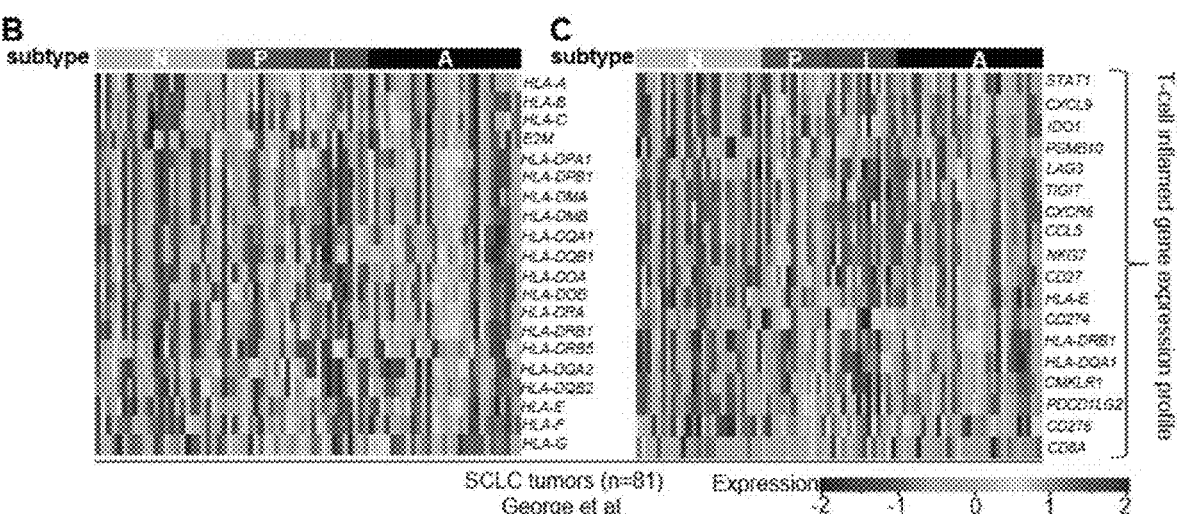
FIGS. 3B-C

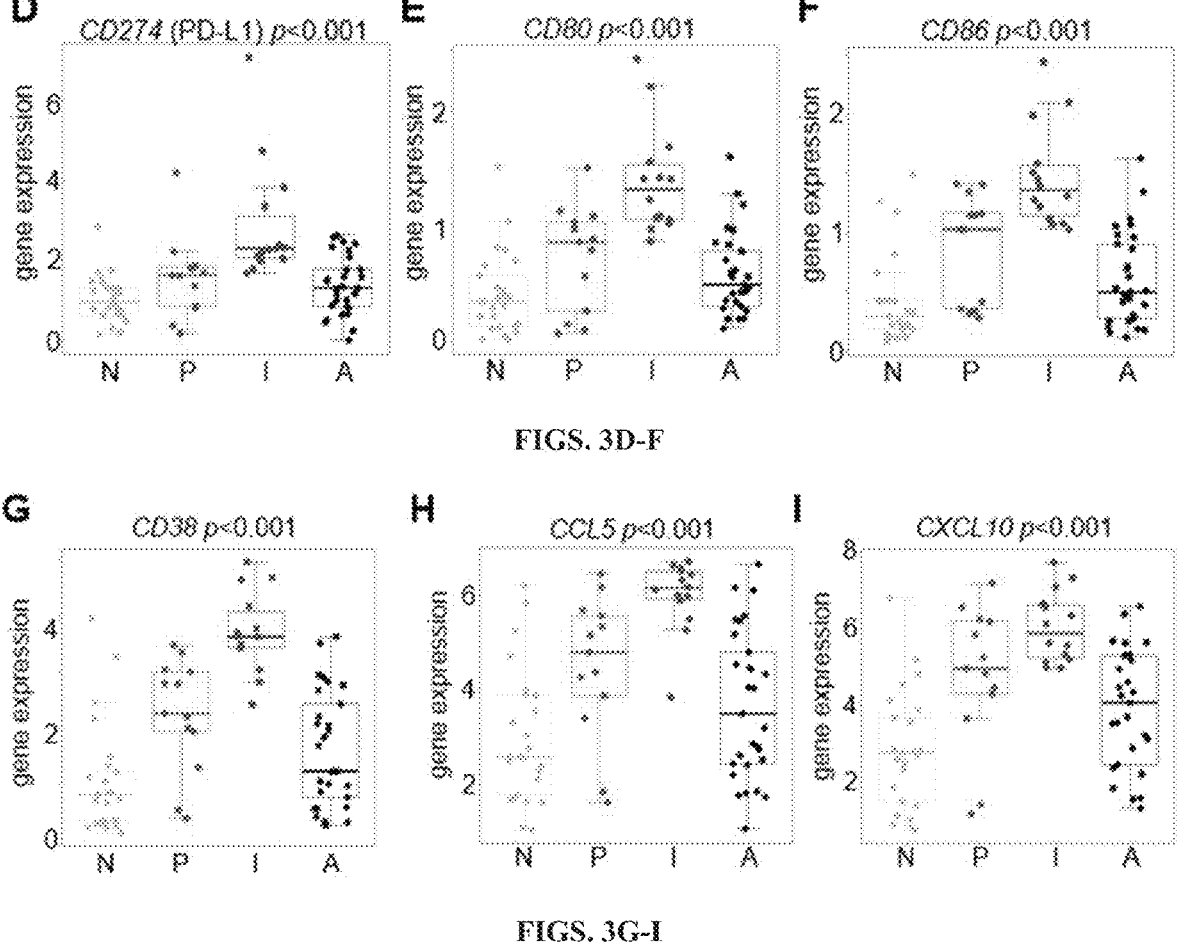
FIGS. 3D-F
FIGS. 3G-I

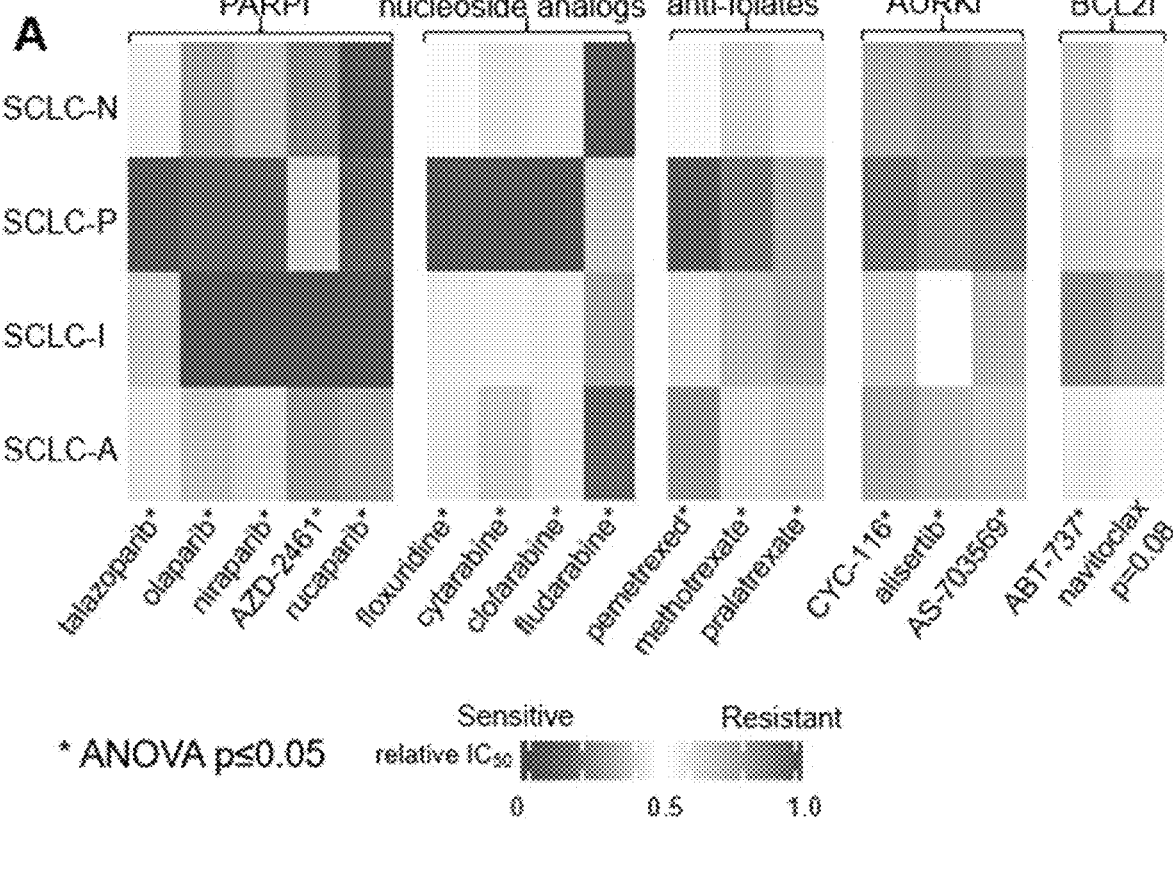
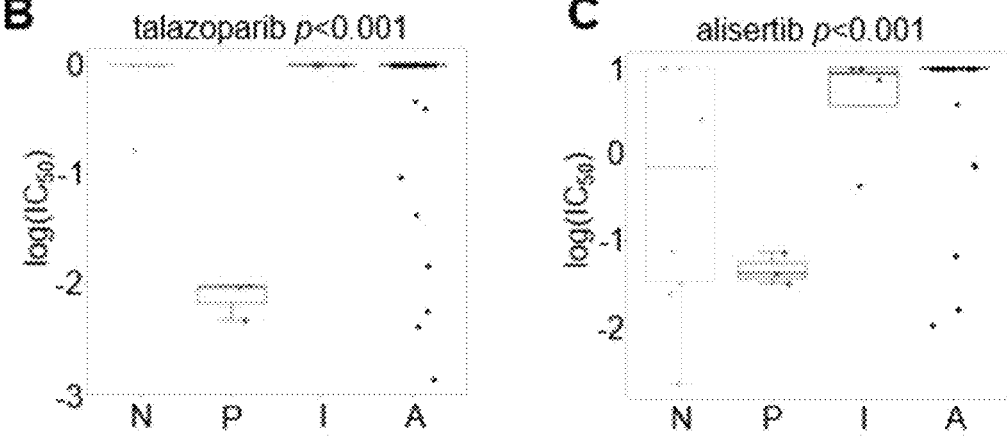
FIGS. 4A-C

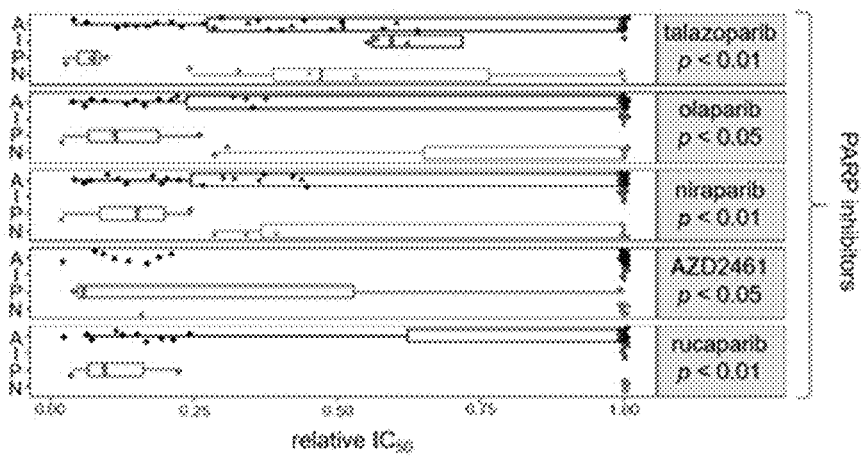
FIG. 4D
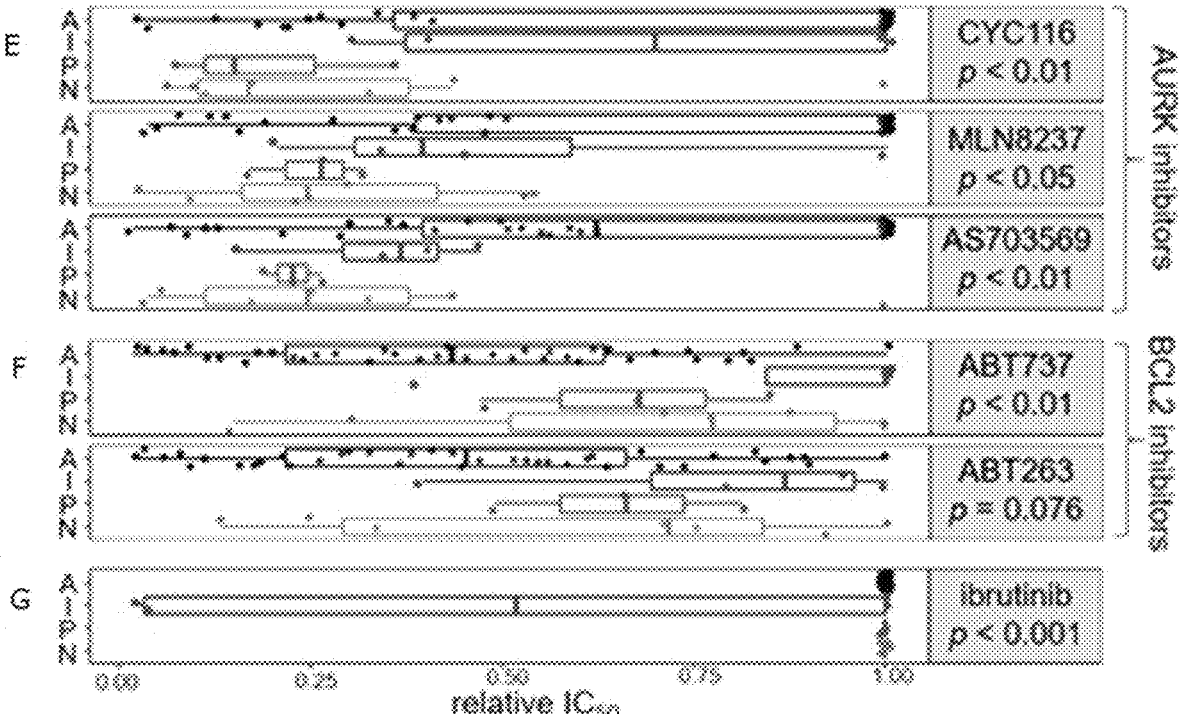
FIGS. 4E-G

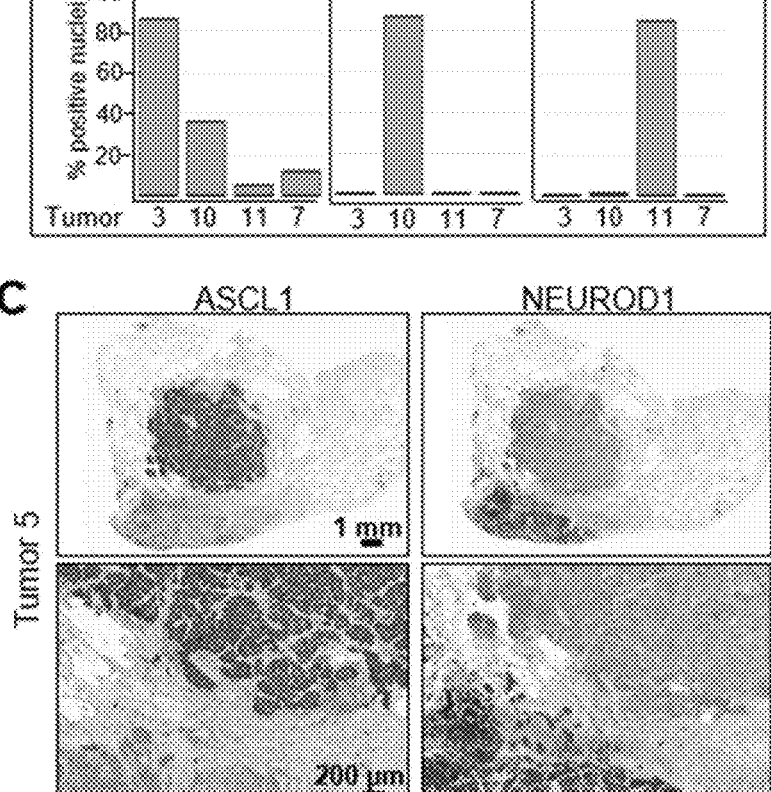
FIGS. 5B-C

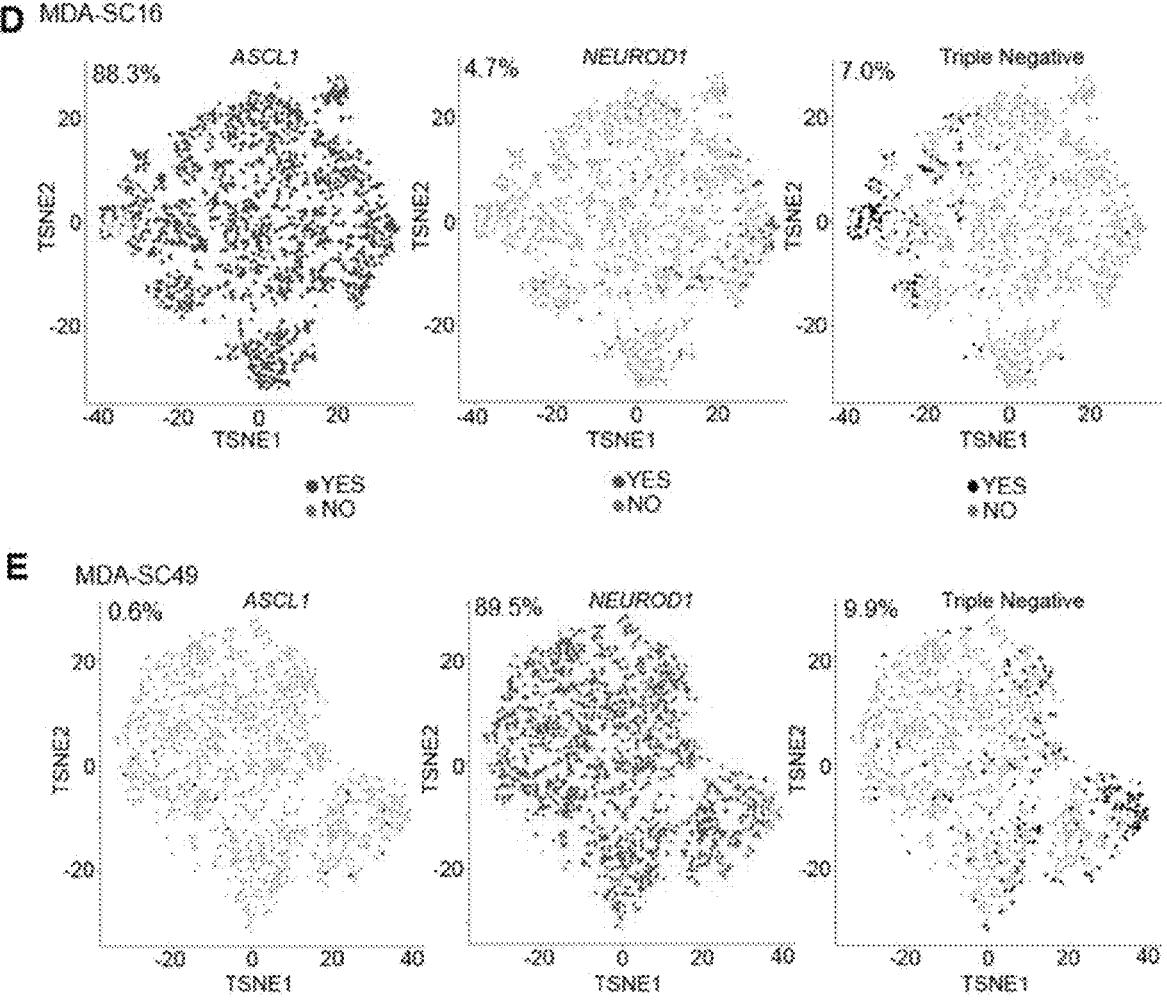
FIGS. 5D-E
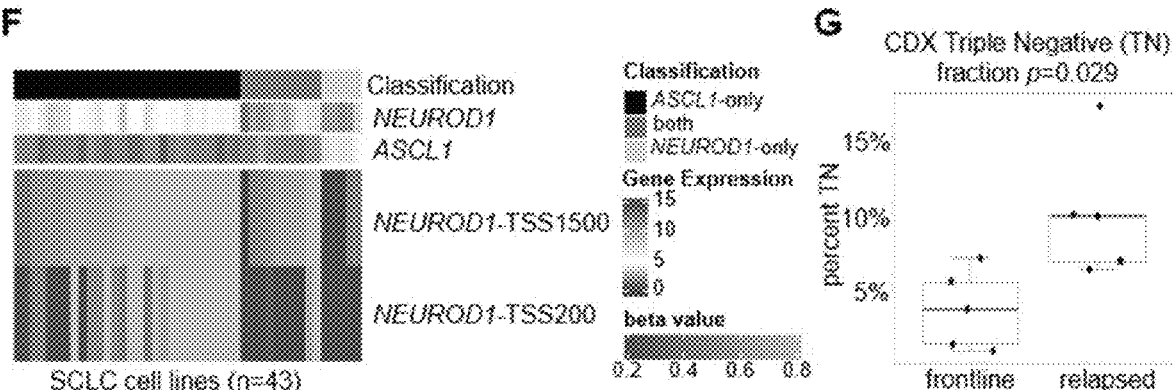
FIGS. 5F-G

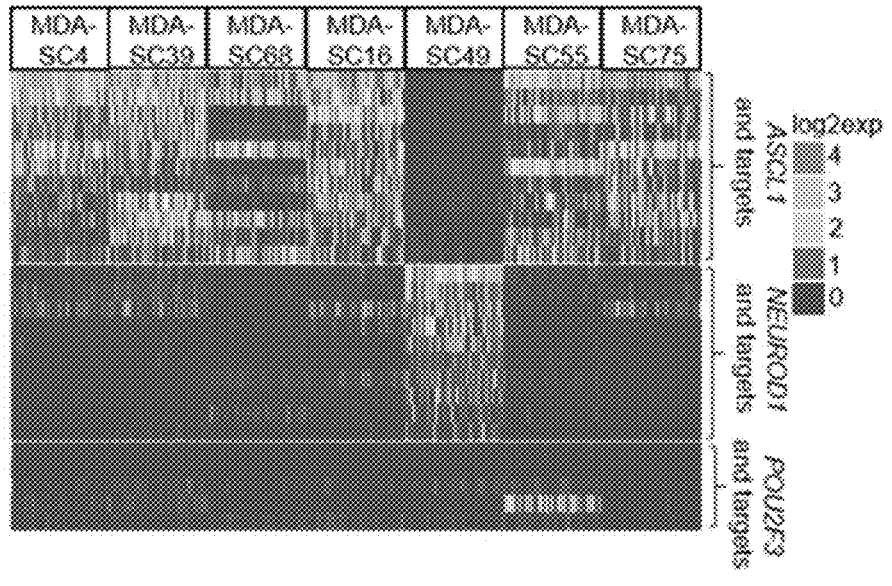
FIG. 5H
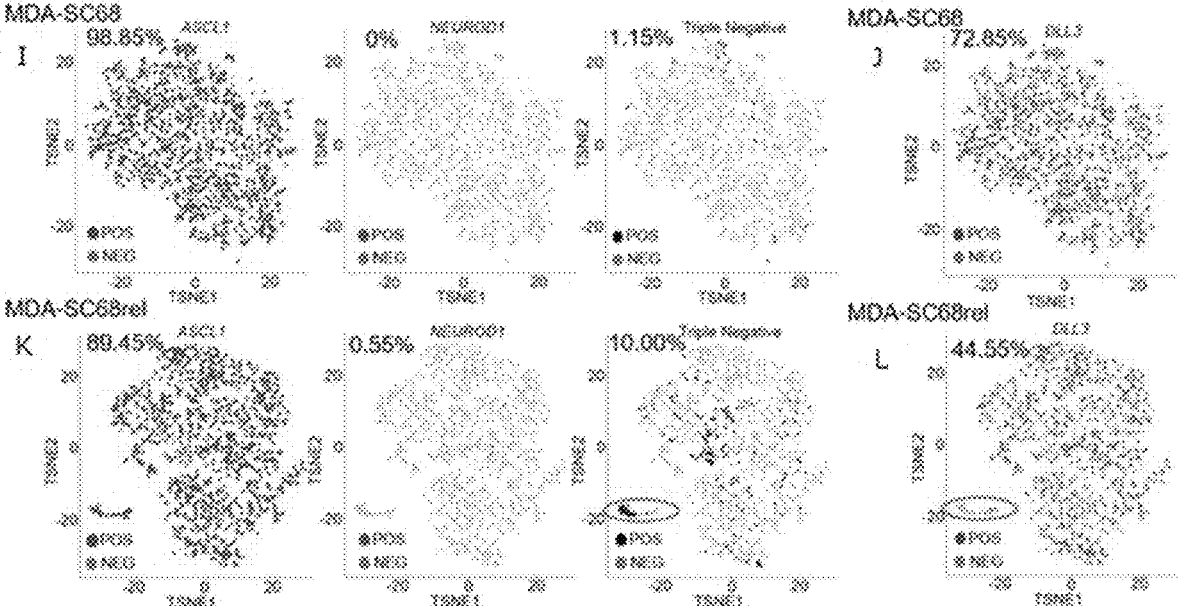
FIGS. 5I-L

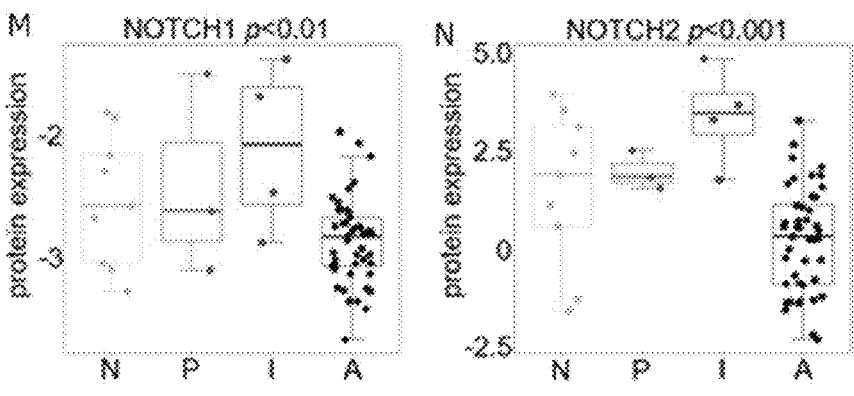
FIGS. 5M-N
FIGS. 6A-D

E
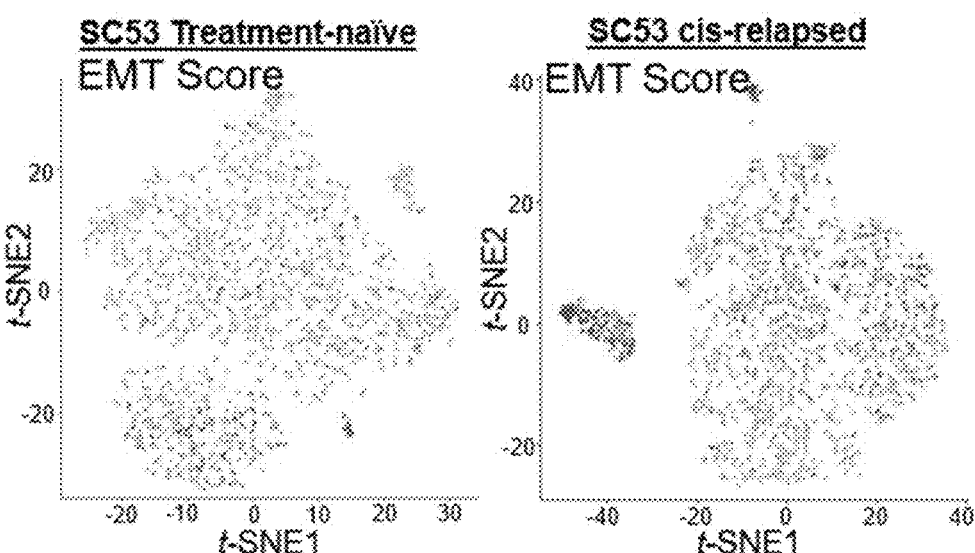
F
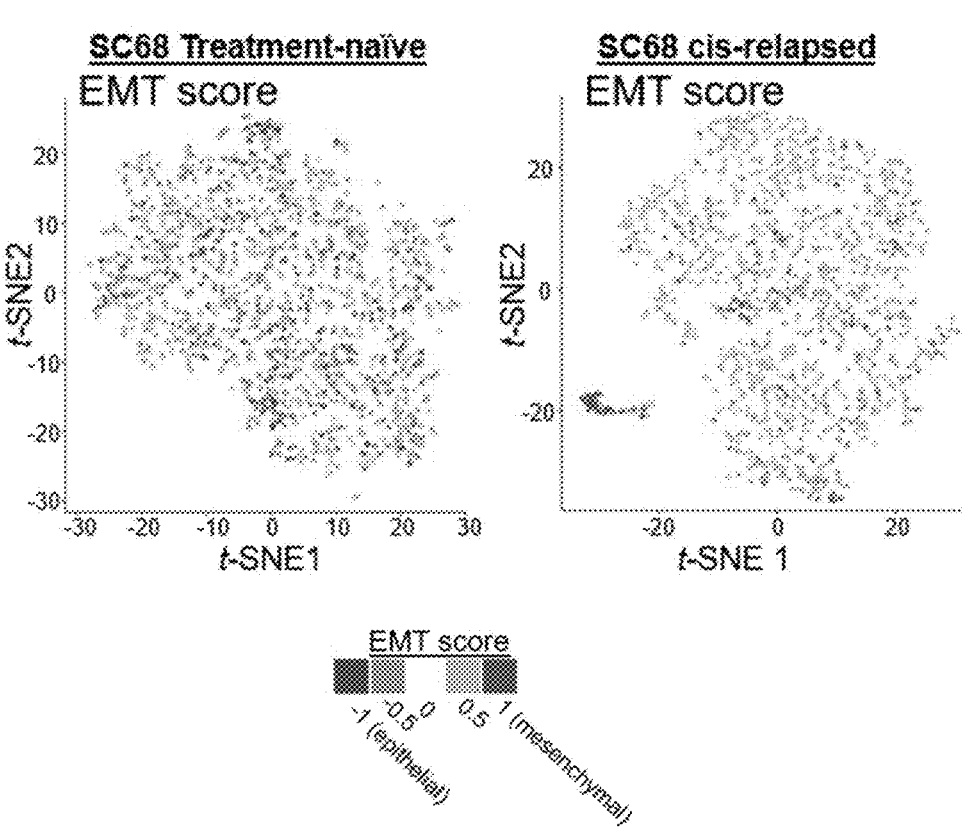
FIGS. 6E-F

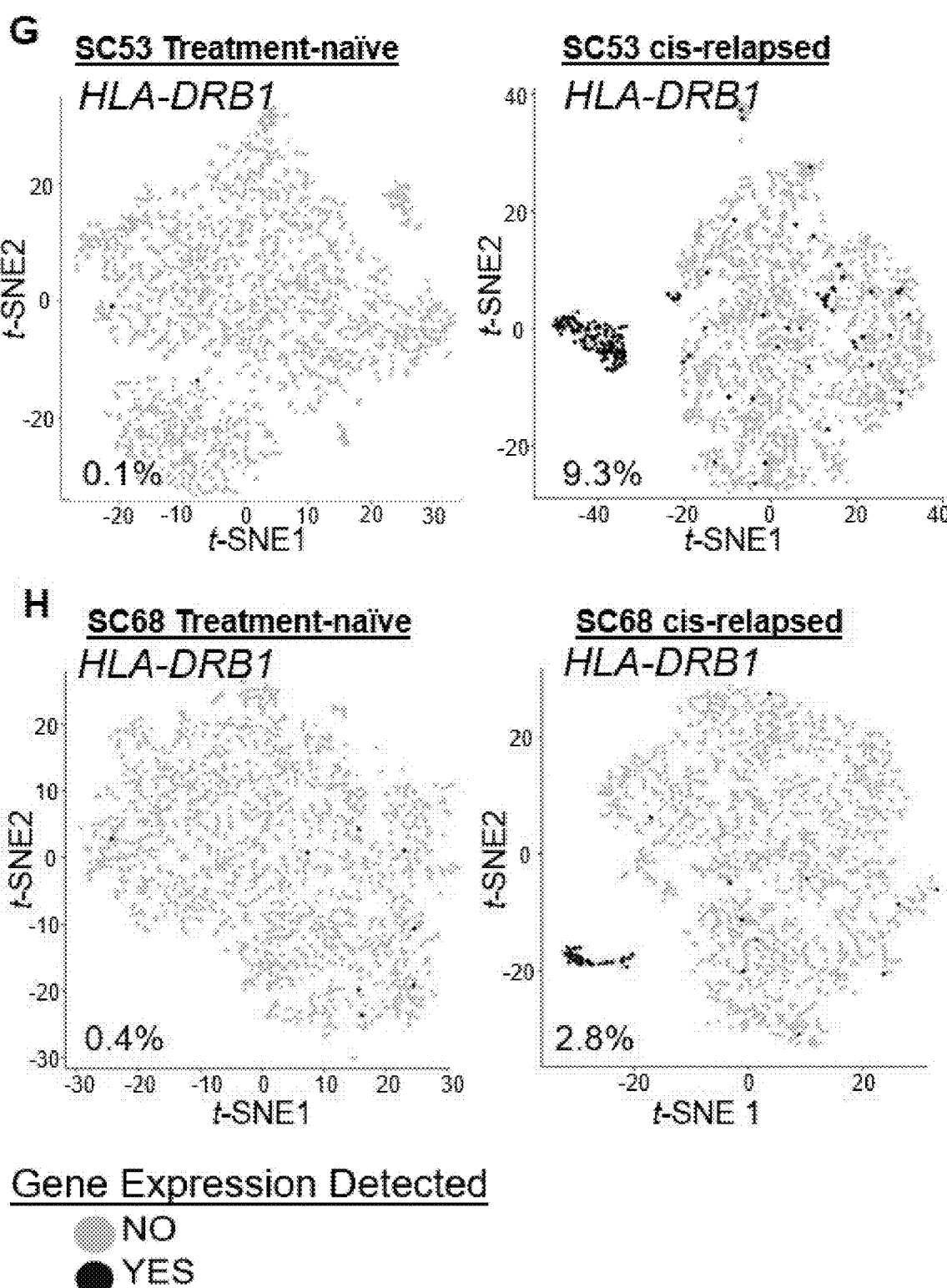
FIGS. 6G-H

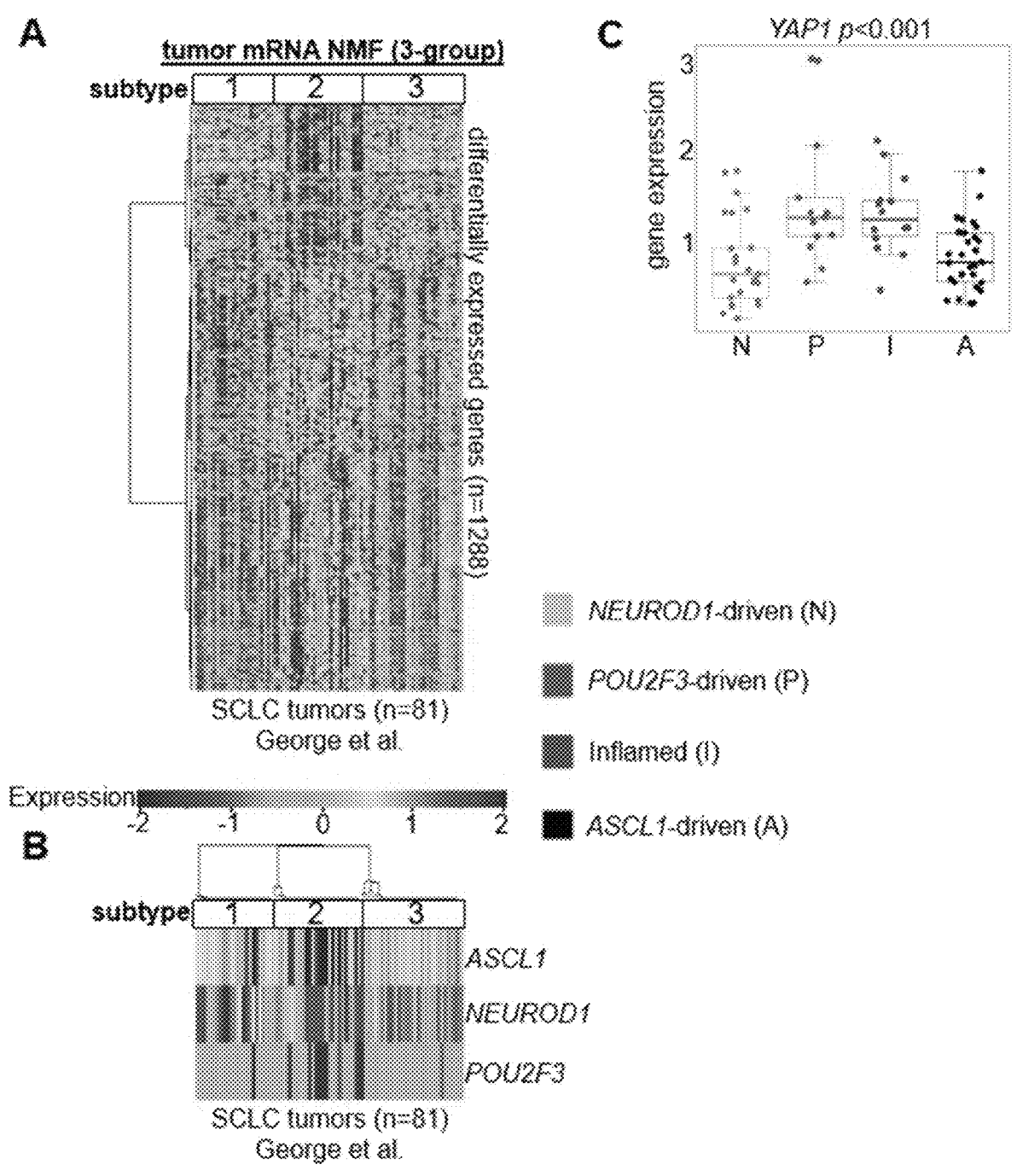
FIGS. 7A-C

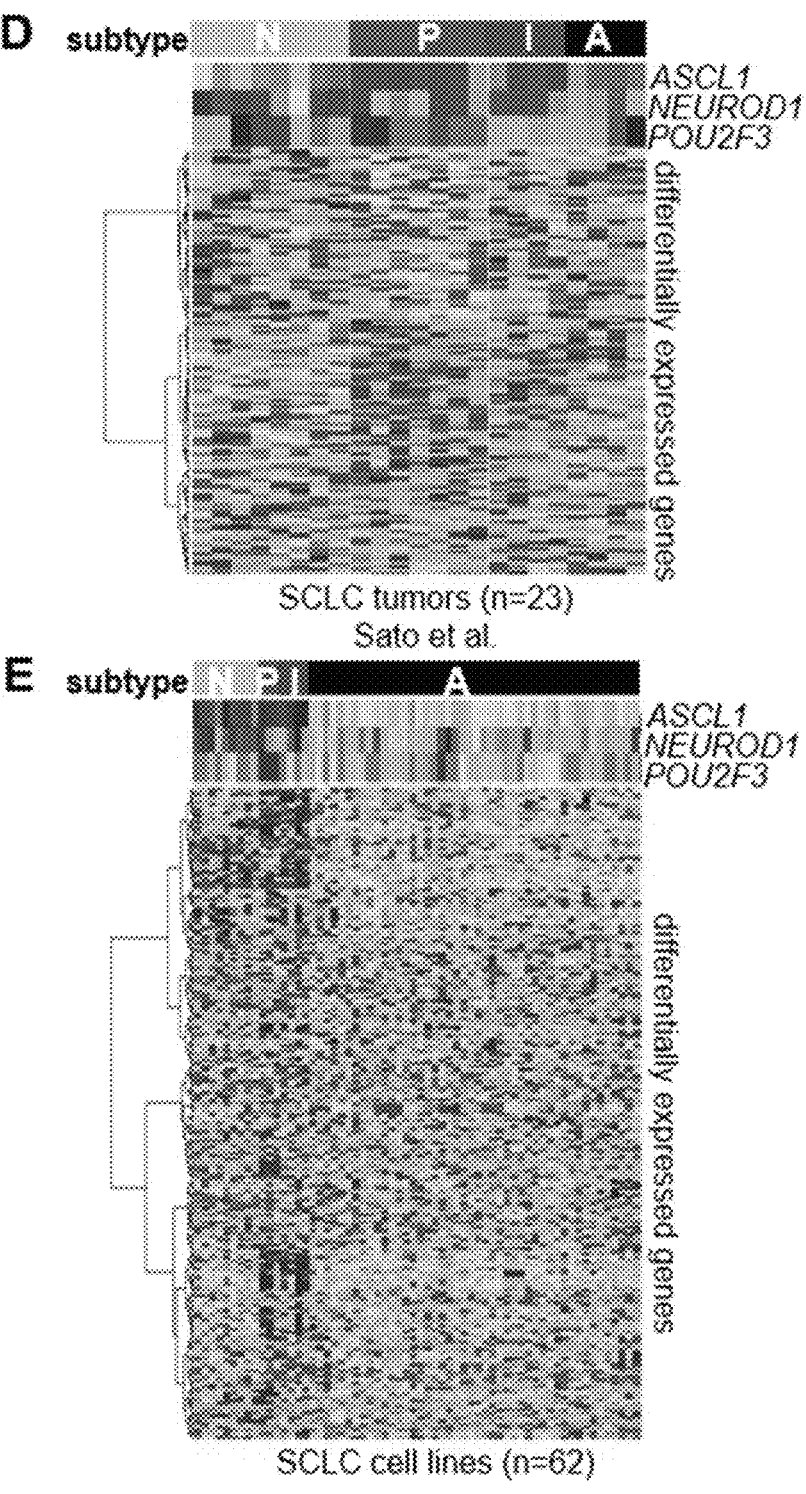
FIGS. 7D-E

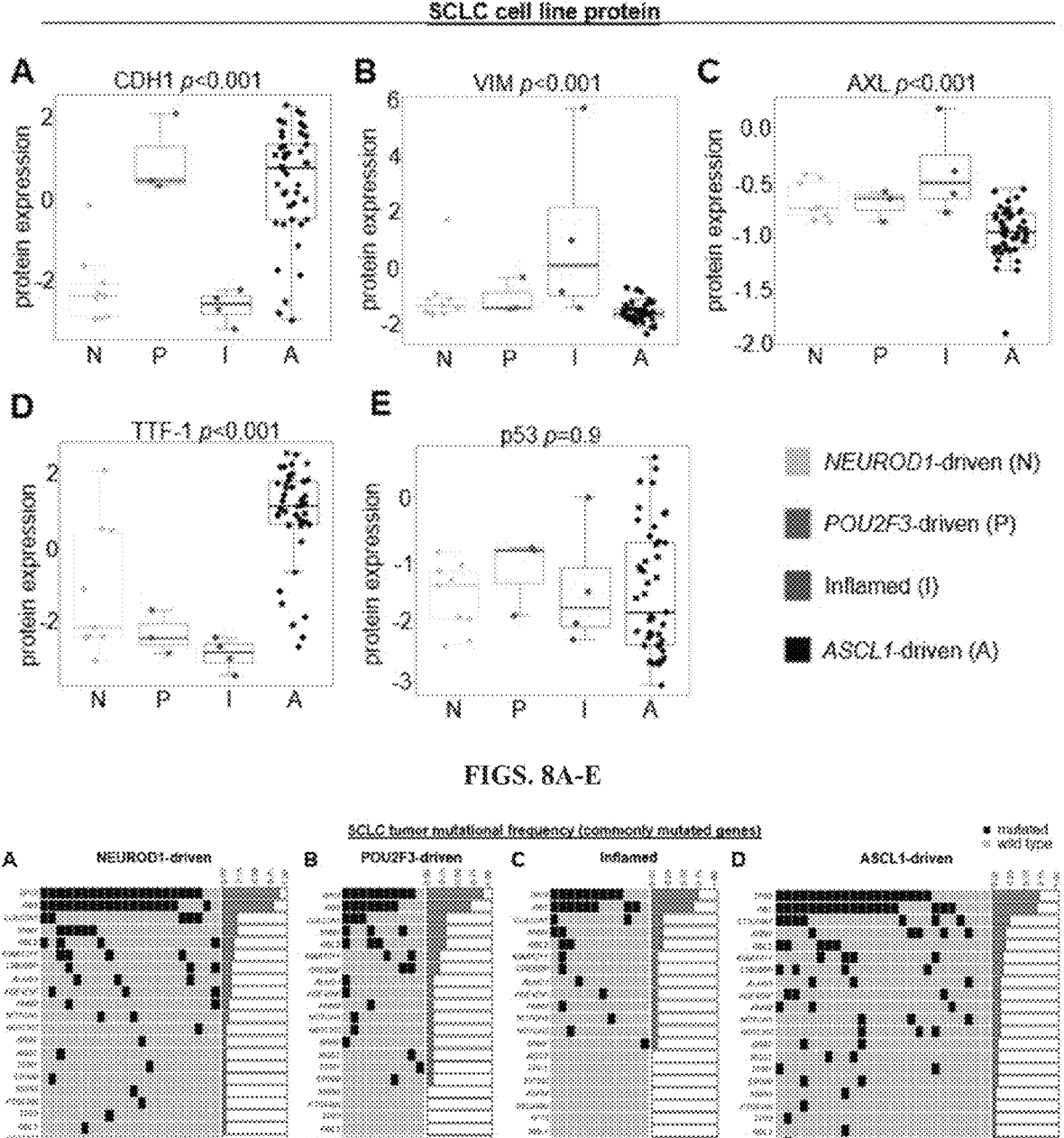
FIGS. 8A-E
FIGS. 9A-D

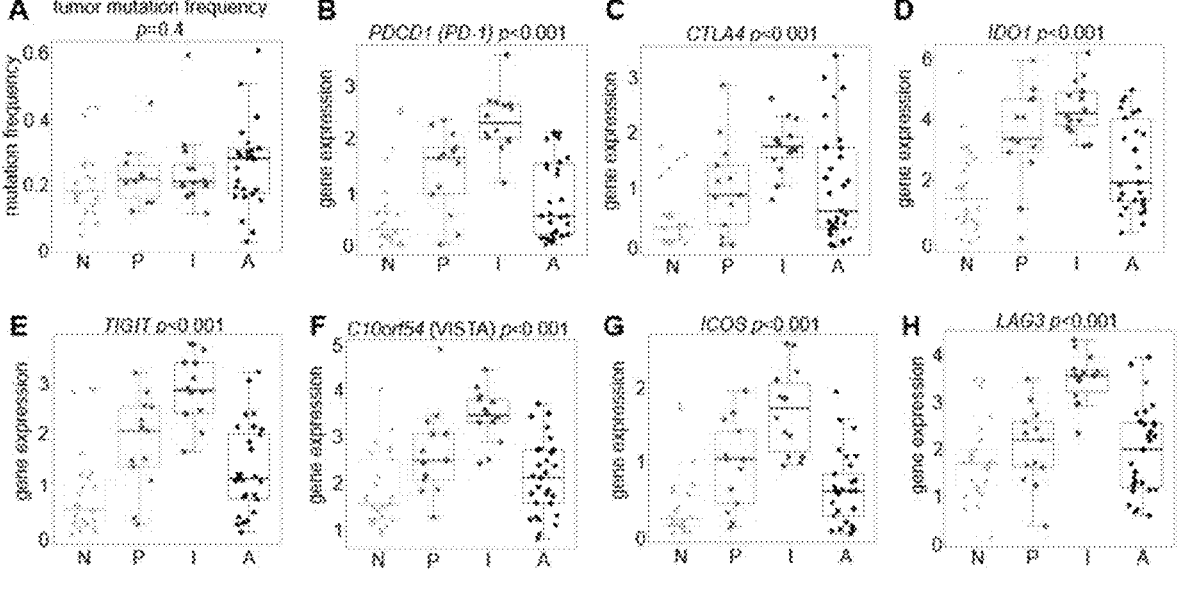
FIGS. 10A-H

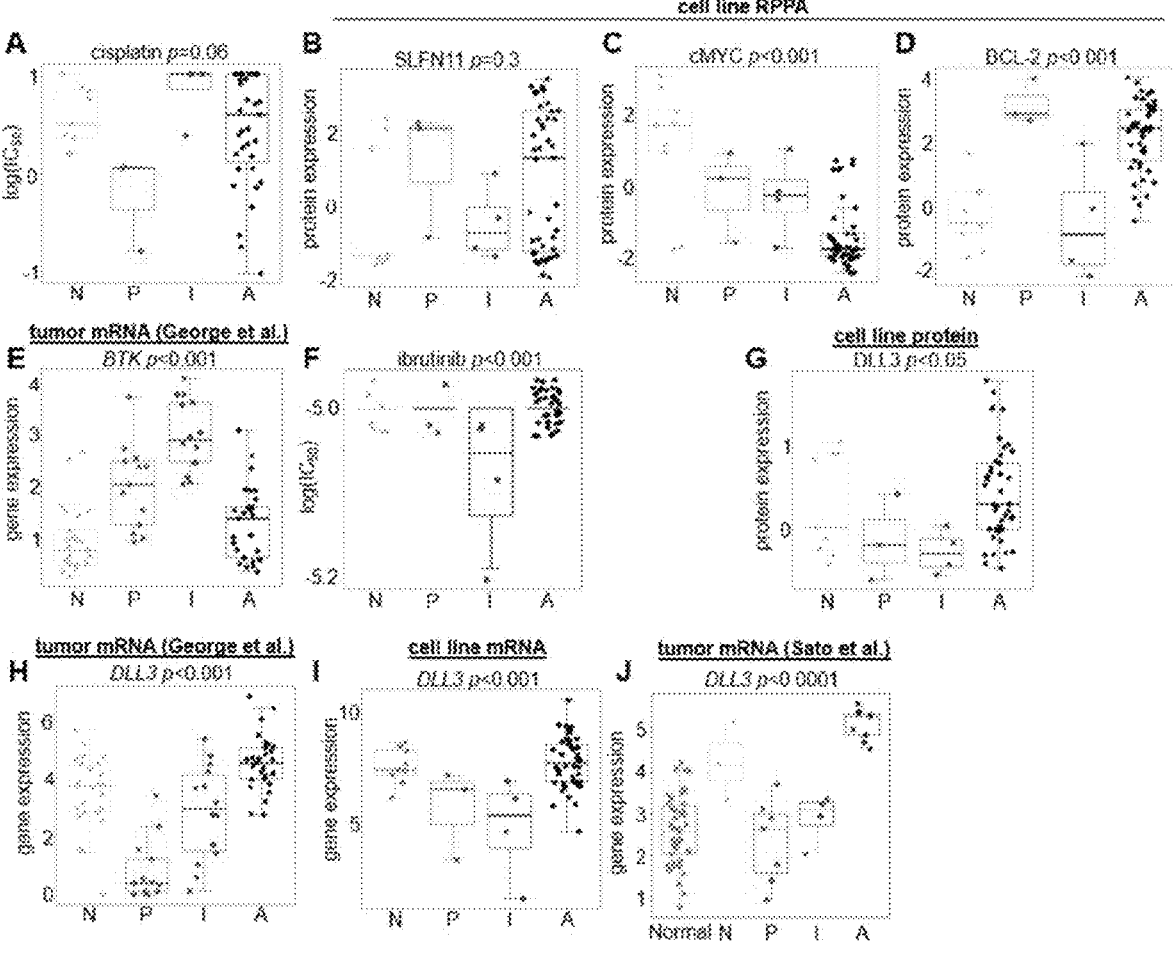
FIGS. 11A-J

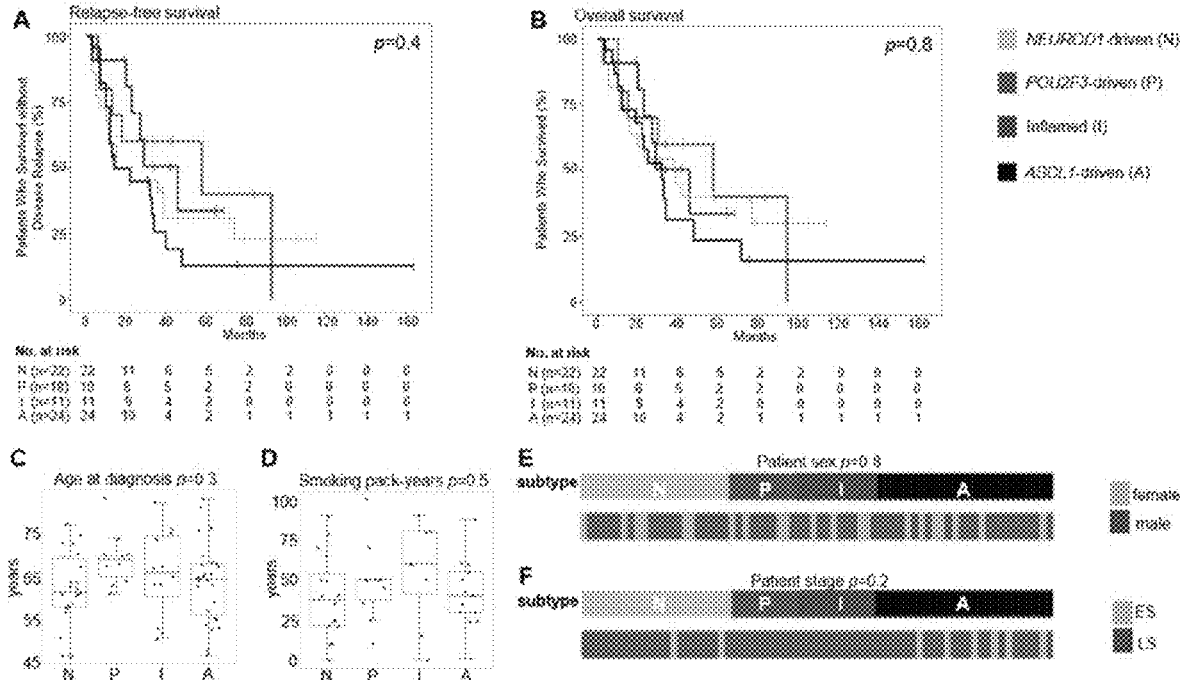
FIGS. 12A-F
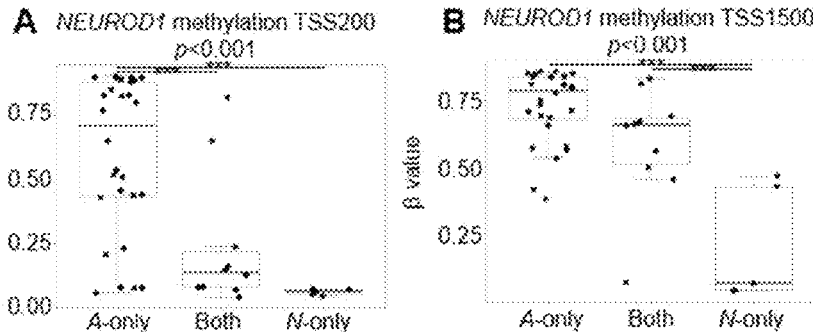
FIGS. 13A-B

MOLECULAR SUBTYPING OF SMALL CELL LUNG CANCER TO PREDICT THERAPEUTIC RESPONSES

REFERENCE TO RELATED APPLICATIONS

The present application is a divisional application from U.S. patent application Ser. No. 17/011,519, filed Sep. 3, 2020, which claims the priority benefit of U.S. provisional application No. 62/895,322, filed Sep. 3, 2019, the entire contents of which are incorporated herein by reference.

STATEMENT REGARDING FEDERALLY SPONSORED RESEARCH

This invention was made with government support under Grant No. R01 CA207295 awarded by the National Institutes of Health. The government has certain rights in the invention.

BACKGROUND

1. Field

The present invention relates generally to the fields of medicine and oncology. More particularly, it concerns methods for classifying small cell lung cancer patients as well as using such classification in treating patients having small cell lung cancer.

2. Description of Related Art

Small cell lung cancer (SCLC) is an aggressive neuroendocrine malignancy with dismal long-term survival rates (Byers & Rudin, 2015). Despite recent advancements in the standard of care—most notably with the recent addition of immunotherapy to platinum-based frontline chemotherapy—the absolute improvements in progression-free survival (PFS) and overall survival (OS) are modest (Antonia et al., 2016; Chung et al., 2020; Horn et al., 2018; Chung et al., 2018; Paz-Ares et al., 2019). In contrast to non-small cell lung cancer (NSCLC), where patient selection for targeted and immune-based therapies has dramatically altered treatment approaches and patient outcomes (Zimmermann et al., 2018), a persistent challenge in optimizing therapy for SCLC patients remains a lack of prospectively validated biomarkers. As a result, clinical trials for SCLC patients have focused on unselected populations and have yielded predictably disappointing results. Better defining the subsets of SCLC that predict sensitivity, or govern resistance, to targeted and immune-based therapies represents a fundamental unmet need for this disease.

SCLC was once characterized as a molecularly homogeneous tumor due to the near-universal loss of TP53 and RB1 and neuroendocrine/epithelial differentiation. The identification of subsets of MYC-driven SCLC that possess unique therapeutic vulnerabilities (Cardnell et al., 2017; Chalishazar et al., 2019; Mollaoglu et al., 2017) or chemoresistant, mesenchymal SCLC variants (Bottger et al., 2019; Allison Stewart et al., 2017) suggested the need to refine this characterization to accommodate inter-tumoral heterogeneity. Several investigators have recently described, with enhanced granularity, unique molecular subtypes in SCLC. The consensus definition of these molecular subtypes has evolved from classic and variant to neuroendocrine and non-neuroendocrine to, increasingly, transcription factor defined molecular subsets (Carney et al., 1985; Gazdar et al., 1985; Zhang et al., 2018; Rudin et al., 2019). These latter subsets were historically centered on the expression of neuroendocrine transcription factors ASCL1 and/or NEUROD1 (Borromeo et al., 2016). However, a third transcription factor, POU2F3, was recently identified as defining a previously unappreciated non-neuroendocrine, tuft-cell variant of SCLC (Huang et al., 2018). Despite the addition of this third subtype, many SCLC tumors still fall outside of these three groups, even with the addition of a putative fourth subtype driven by the transcription factor YAP1 (Rudin et al., 2019). However, it is not known to what extent specific subtype classification may predict responses to most chemo-, targeted-, or immune-based therapies.

SUMMARY

As such, provided herein are predictive markers for subdividing SCLC into definitive, mutually exclusive molecular subtypes by gene and/or protein expression analyses. These subtypes are defined by unique biological features that underlie discrete therapeutic vulnerabilities.

In one embodiment, provided herein are methods of classifying a patient having a small cell lung cancer, the method comprising: (a) obtaining a sample of the patient's cancer; (b) measuring an expression level of ASCL1, NEUROD1, and POU2F3 in the sample or determining a methylation status of ASCL1, NEUROD1, and POU2F3 in the sample; and (c) classifying the patient having a small cell lung cancer based on the expression level of ASCL1, NEUROD1, and POU2F3 in the sample or the methylation status of ASCL1, NEUROD1, and POU2F3 in the sample. In some aspects, the patient is a human.

In some aspects, if ASCL1 is expressed or ASCL1 is not methylated, then the patient is classified as having a small cell lung cancer that is sensitive to a BCL-2 inhibitor or a DLL3-targeting molecule. In some aspects, the methods further comprise administering a therapeutically effective amount of a BCL-2 inhibitor or a DLL3-targeting molecule to the patient.

In some aspects, if ASCL1 is expressed or ASCL1 is not methylated, then the methods further comprise measuring an expression level of SLFN11 in the sample, wherein if high levels of SLFN11 are expressed in the sample, then the patient is classified as having a small cell lung cancer that is sensitive to a PARP inhibitor, cisplatin, ATM inhibitor (e.g., AZD0156), ATR inhibitor (e.g., AZD6738), WEE1 inhibitor (e.g., AZD1775), mTOR inhibitor (e.g., AZD2014), a DLL3 targeting molecule, or a combination thereof. In some aspects, the methods further comprise administering a therapeutically effective amount of a PARP inhibitor, cisplatin, ATM inhibitor (e.g., AZD0156), ATR inhibitor (e.g., AZD6738), WEE1 inhibitor (e.g., AZD1775), mTOR inhibitor (e.g., AZD2014), a DLL3 targeting molecule, or a combination thereof to the patient.

In some aspects, if NEUROD1 is expressed or NEUROD1 is not methylated, then the patient is classified as having a small cell lung cancer that is sensitive to an Aurora kinase inhibitor. In some aspects, the methods further comprise administering a therapeutically effective amount of an Aurora kinase inhibitor to the patient.

In some aspects, if POU2F3 is expressed or POU2F3 is not methylated, then the patient is classified as having a small cell lung cancer that is sensitive to a PARP inhibitor, a nucleoside analogue, an anti-metabolite, or a platinum-containing chemotherapeutic agent. In some aspects, the methods further comprise administering a therapeutically effective amount of a PARP inhibitor, a nucleoside analogue, an anti-metabolite, or a platinum-containing chemotherapeutic agent to the patient.

In some aspects, if none of ASCL1, NEUROD1, and POU2F3 is expressed or ASCL1, NEUROD1, and POU2F3 are each methylated, then the patient is classified as having a small cell lung cancer that is sensitive to an immune checkpoint inhibitor or a BTK inhibitor. In some aspects, the methods further comprise administering a therapeutically effective amount of an immune checkpoint inhibitor or a BTK inhibitor to the patient. In some aspects, the sample is determined to express at least one of an immune checkpoint protein, an inflammatory marker, a STING pathway protein, CCL5, CXCL10, an MHC protein, CD274 (PD-L1), LAG3, C10orf54 (VISTA), ID01, LAG3, CD38, and ICOS.

In some aspects, if ASCL1 is expressed or ASCL1 is not methylated, then the methods further comprise administering a therapeutically effective amount of a platinum-containing chemotherapeutic agent to induce switching to an SCLC-I subtype, and then further treating the patient with an immune checkpoint inhibitor or a BTK inhibitor.

In some aspects, the expression of a gene is measured by detecting a level of mRNA transcribed from the gene. In some aspects, the mRNA is detected by microarray, RT-PCR, qRT-PCR, nanostring assay, or in situ hybridization. In some aspects, the expression of a gene is measured by detecting a level of cDNA produced from reverse transcription of mRNA transcribed from the gene. In some aspects, the expression of a gene is measured by detecting a level of a polypeptide encoded by the gene. In some aspects, the sample is a formalin-fixed, paraffin-embedded sample. In some aspects, the sample is a fresh frozen sample.

In some aspects, the methods further comprise administering at least a second anti-cancer therapy to the patient. In some aspects, the second anti-cancer therapy is a surgical therapy, chemotherapy, radiation therapy, cryotherapy, hormonal therapy, toxin therapy, immunotherapy, or cytokine therapy.

In some aspects, the patient has previously undergone at least one round of anti-cancer therapy. In some aspects, the patient has previously failed to respond to treatment. In some aspects, the patient has relapsed following treatment.

In some aspects, the methods further comprise reporting the classification of the patient. In some aspects, the reporting comprises preparing a written or electronic report. In some aspects, the methods further comprise providing the report to the patient, a doctor, a hospital, or an insurance company.

In some aspects, the methods further comprise performing the classification a second time. In some aspects, the second time is after the patient has developed resistance to a first anti-cancer therapy.

In some aspects, the patient falls into two or more classifications, wherein the patient is administered a therapeutic agent for each classification.

In one embodiment, provided herein are methods of selecting a patient having a small cell lung cancer for treatment with a BCL-2 inhibitor or a DLL3-targeting molecule, the method comprising (a) determining whether DLL-3 is expressed in the cancer, and (b) selecting the patient for treatment if DLL-3 is expressed in the cancer. In some aspects, step (a) comprises (i) obtaining or having obtained a biological sample from the patient; and (ii) performing or having performed an assay on the biological sample to determine whether DLL-3 is expressed in the cancer. In some aspects, the methods further comprise administering a therapeutically effective amount of a BCL-2 inhibitor or a DLL3-targeting molecule to the selected patient.

In one embodiment, provided herein are methods of treating a patient having a small cell lung cancer, the method comprising administering a therapeutically effective amount of a BCL-2 inhibitor or a DLL3-targeting molecule to the patient, wherein the patient's cancer expresses DLL-3.

In one embodiment, provided herein are methods of selecting a patient having a small cell lung cancer for treatment with a PARP inhibitor, a nucleoside analogue, an anti-metabolite, or a platinum-containing chemotherapeutic agent, the method comprising (a) determining whether POU2F3 is expressed in the cancer, and (b) selecting the patient for treatment if POU2F3 is expressed in the cancer. In some aspects, step (a) comprises (i) obtaining or having obtained a biological sample from the patient; and (ii) performing or having performed an assay on the biological sample to determine whether POU2F3 is expressed in the cancer. In some aspects, the methods further comprise administering a therapeutically effective amount of a PARP inhibitor, a nucleoside analogue, an anti-metabolite, or a platinum-containing chemotherapeutic agent to the selected patient.

In one embodiment, provided herein are methods of treating a patient having a small cell lung cancer, the method comprising administering a therapeutically effective amount of a PARP inhibitor, a nucleoside analogue, an anti-metabolite, or a platinum-containing chemotherapeutic agent to the patient, wherein the patient's cancer expresses POU2F3.

In one embodiment, provided herein are methods of treating a patient having a small cell lung cancer, the method comprising: (a) determining or having determined whether the patient's cancer expresses POU2F3; (b) selecting or having selected the patient for treatment when the cancer expresses POU2F3; and (c) administering or having administered to the selected patient a therapeutically effective amount of a PARP inhibitor, a nucleoside analogue, an anti-metabolite, or a platinum-containing chemotherapeutic agent. In some aspects, step (a) comprises (i) obtaining or having obtained a biological sample from the cancer; and (ii) performing or having performed an assay on the biological sample to determine whether POU2F3 is expressed.

In some aspects, whether POU2F3 is expressed in the cancer is determined by detecting a POU2F3 protein in the sample. In some aspects, the protein is detected by mass spectrometry, western blot, immunohistochemistry, ELISA, or RIA. In some aspects, whether POU2F3 is expressed in the cancer is determined by detecting a POU2F3 mRNA in the sample. In some aspects, the mRNA is detected by microarray, RT-PCR, qRT-PCR, nanostring assay, or in situ hybridization.

In one embodiment, provided herein are methods of selecting a patient having a small cell lung cancer for treatment with a PARP inhibitor, a nucleoside analogue, an anti-metabolite, or a platinum-containing chemotherapeutic agent, the method comprising (a) determining whether POU2F3 is methylated in the cancer, and (b) selecting the patient for treatment if POU2F3 is not methylated in the cancer. In some aspects, step (a) comprises (i) obtaining or having obtained a biological sample from the patient; and (ii) performing or having performed an assay on the biological sample to determine whether POU2F3 is methylated in the cancer. IN some aspects, the methods further comprise administering a therapeutically effective amount of a PARP inhibitor, a nucleoside analogue, an anti-metabolite, or a platinum-containing chemotherapeutic agent to the selected patient.

In one embodiment, provided herein are methods of treating a patient having a small cell lung cancer, the method comprising administering a therapeutically effective amount of a PARP inhibitor, a nucleoside analogue, an anti-metabolite, or a platinum-containing chemotherapeutic agent to the patient, wherein the POU2F3 gene in the patient's cancer is not methylated.

In one embodiment, provided herein are methods of treating a patient having a small cell lung cancer, the method comprising: (a) determining or having determined whether the POU2F3 gene in the patient's cancer is methylated; (b) selecting or having selected the patient for treatment when the POU2F3 gene in the patient's cancer is not methylated; and (c) administering or having administered to the selected patient a therapeutically effective amount of a PARP inhibitor, a nucleoside analogue, an anti-metabolite, or a platinum-containing chemotherapeutic agent. In some aspects, step (a) comprises (i) obtaining or having obtained a biological sample from the cancer; and (ii) performing or having performed an assay on the biological sample to determine whether the POU2F3 gene in the patient's cancer is methylated.

In some aspects, the sample is a formalin-fixed, paraffin-embedded sample. In some aspects, the sample is a fresh frozen sample. In some aspects, the methods further comprise administering at least a second anti-cancer therapy to the patient. In some aspects, the second anti-cancer therapy is a surgical therapy, chemotherapy, radiation therapy, cryotherapy, hormonal therapy, toxin therapy, immunotherapy, or cytokine therapy.

In some aspects, the patient has previously undergone at least one round of anti-cancer therapy. In some aspects, the patient has previously failed to respond to treatment. In some aspects, the patient has relapsed following treatment. In some aspects, the patient is a human.

In one embodiment, provided herein are methods of selecting a patient having a small cell lung cancer for treatment with an immune checkpoint inhibitor or a BTK inhibitor, the method comprising (a) determining whether ASCL1, NEUROD1, and POU2F3 are expressed in the cancer, and (b) selecting the patient for treatment if none of ASCL1, NEUROD1, and POU2F3 is expressed in the cancer. In some aspects, step (a) comprises (i) obtaining or having obtained a biological sample from the patient; and (ii) performing or having performed an assay on the biological sample to determine whether ASCL1, NEUROD1, and POU2F3 is expressed in the cancer. In some aspects, the methods further comprise administering a therapeutically effective amount of an immune checkpoint inhibitor or a BTK inhibitor to the selected patient.

In one embodiment, provided herein are methods of treating a patient having a small cell lung cancer, the method comprising administering a therapeutically effective amount of an immune checkpoint inhibitor or a BTK inhibitor to the patient, wherein the patient's cancer has been determined to expresses none of ASCL1, NEUROD1, and POU2F3.

In one embodiment, provided herein are methods of treating a patient having a small cell lung cancer, the method comprising: (a) determining or having determined whether the patient's cancer expresses ASCL1, NEUROD1, and POU2F3; (b) selecting or having selected the patient for treatment when the cancer expresses none of ASCL1, NEUROD1, and POU2F3; and (c) administering or having administered to the selected patient a therapeutically effective amount of an immune checkpoint inhibitor or a BTK inhibitor. In some aspects, step (a) comprises (i) obtaining or having obtained a biological sample from the cancer; and (ii) performing or having performed an assay on the biological sample to determine whether ASCL1, NEUROD1, and POU2F3 are expressed.

In some aspects, whether ASCL1, NEUROD1, and POU2F3 is expressed in the cancer is determined by detecting a ASCL1, NEUROD1, and POU2F3 protein in the sample. In some aspects, the protein is detected by mass spectrometry, western blot, immunohistochemistry, ELISA, or RIA. In some aspects, whether ASCL1, NEUROD1, and POU2F3 is expressed in the cancer is determined by detecting a ASCL1, NEUROD1, and POU2F3 mRNA in the sample. In some aspects, the mRNA is detected by microarray, RT-PCR, qRT-PCR, nanostring assay, or in situ hybridization.

In one embodiment, provided herein are methods of selecting a patient having a small cell lung cancer for treatment with an immune checkpoint inhibitor or a BTK inhibitor, the method comprising (a) determining whether ASCL1, NEUROD1, and POU2F3 are methylated in the cancer, and (b) selecting the patient for treatment if each of ASCL1, NEUROD1, and POU2F3 is methylated in the cancer. In some aspects, step (a) comprises (i) obtaining or having obtained a biological sample from the patient; and (ii) performing or having performed an assay on the biological sample to determine whether ASCL1, NEUROD1, and POU2F3 are methylated in the cancer. In some aspects, the methods further comprise administering a therapeutically effective amount of an immune checkpoint inhibitor or a BTK inhibitor to the selected patient.

In one embodiment, provided herein are methods of treating a patient having a small cell lung cancer, the method comprising administering a therapeutically effective amount of an immune checkpoint inhibitor or a BTK inhibitor to the patient, wherein it has been determined that each of ASCL1, NEUROD1, and POU2F3 is methylated in the patient's cancer.

In one embodiment, provided herein are methods of treating a patient having a small cell lung cancer, the method comprising: (a) determining or having determined whether each of ASCL1, NEUROD1, and POU2F3 is methylated in the patient's cancer; (b) selecting or having selected the patient for treatment when each of ASCL1, NEUROD1, and POU2F3 is methylated in the cancer; and (c) administering or having administered to the selected patient a therapeutically effective amount of an immune checkpoint inhibitor or a BTK inhibitor. In some aspects, step (a) comprises (i) obtaining or having obtained a biological sample from the cancer; and (ii) performing or having performed an assay on the biological sample to determine whether each of ASCL1, NEUROD1, and POU2F3 is methylated.

In some aspects, the sample is a formalin-fixed, paraffin-embedded sample. In some aspects, the sample is a fresh frozen sample. In some aspects, the methods further comprise administering at least a second anti-cancer therapy to the patient. In some aspects, the second anti-cancer therapy is a surgical therapy, chemotherapy, radiation therapy, cryotherapy, hormonal therapy, toxin therapy, immunotherapy, or cytokine therapy. In some aspects, the patient has previously undergone at least one round of anti-cancer therapy. In some aspects, the patient has previously failed to respond to treatment. In some aspects, the patient has relapsed following treatment. In some aspects, the patient is a human.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the inherent variation in the method being employed to determine the value, the variation that exists among the study subjects, or a value that is within 10% of a stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIGS. 1A-G: NMF identifies four transcriptional subtypes of SCLC. Cophenetic correlation from non-negative matrix factorization (NMF) analysis of resected SCLC tumors (A). Differential expression of NMF-selected genes (B) and, specifically, ASCL1, NEUROD1, and POU2F3 (C) across 4 clusters. Gene expression levels of ASCL1 (D), NEUROD1 (E), and POU2F3 (F) in every SCLC tumor with comparison of mean expression for each subtype. Differential gene expression of ASCL1, NEUROD1, POU2F3, and YAP1 along with transcriptional targets of each across 81 SCLC tumors categorized by subtype (G).

FIGS. 2A-K: Molecular and phenotypic distinctions between SCLC subtypes. Differential expression of neuroendocrine (NE) and non-neuroendocrine (non-NE) genes across all SCLC tumors within each subtype (A), including comparison of mean gene expression of neuroendocrine markers CHGA (B) and SYP (C) and REST, a transcriptional repressor of neuroendocrine gene expression (D), across SCLC tumor subtypes. Lung-specific epithelial-mesenchymal transition (EMT) score calculated for each SCLC tumor with comparison between mean EMT scores for each subtype (E). Differential expression of five genes most commonly amplified in SCLC tumors across each subtype (F). MYC gene expression across subtyped SCLC tumors (G). Differential gene expression of five genes most commonly deleted in SCLC tumors across each subtype (H). Comparison of mean protein expression of RB1 across SCLC cell line subtypes (I). Heatmap of mean methylation β values for genes regulated by methylation (GRMs) that are significantly, differentially methylated between SCLC-A and SCLC-N subtypes, including ASCL1 and NEUROD1 (J).

Plots comparing mean methylation β-values for representative sites associated with ASCL1 and NEUROD1 genes across subtyped SCLC cell lines from SCLC-A and SCLC-N subtypes indicating that each is a GRM (K).

FIGS. 3A-I: SCLC-I defines an inflamed subtype of SCLC with high expression of immune checkpoints. Comparison of mean gene expression of CD8+ T-cell markers (A), and heatmaps comparing expression of major histocompatibility complex (MHC) and antigen presenting genes (B) and 18-genes from interferon-γ-related T-cell gene expression profile (C) across subtyped SCLC tumors. Comparison of mean gene expression of CD274 (PD-L1) (D), CD80 (E), CD86 (F), CD38 (G), and STING-induced T-cell attractant chemokines (H-I) within each subtype of SCLC tumors.

FIGS. 4A-G: SCLC subtypes possess unique therapeutic vulnerabilities. Comparison between each SCLC cell line subtype of mean relative in vitro $IC_{50}$ values for PARP inhibitors, nucleoside analogs, anti-folates, AURK inhibitors, and BCL2 inhibitors (A). Representative examples of in vitro response to a PARPi (talazoparib, B) and an AURKi (alisertib, C). Comparison between each SCLC cell line subtype of mean relative in vitro $IC_{50}$ values for five PARP inhibitors (D), three AURK inhibitors (E), two BCL2 inhibitors (F), and the BTK-inhibitor ibrutinib (G).

Figure 5A:
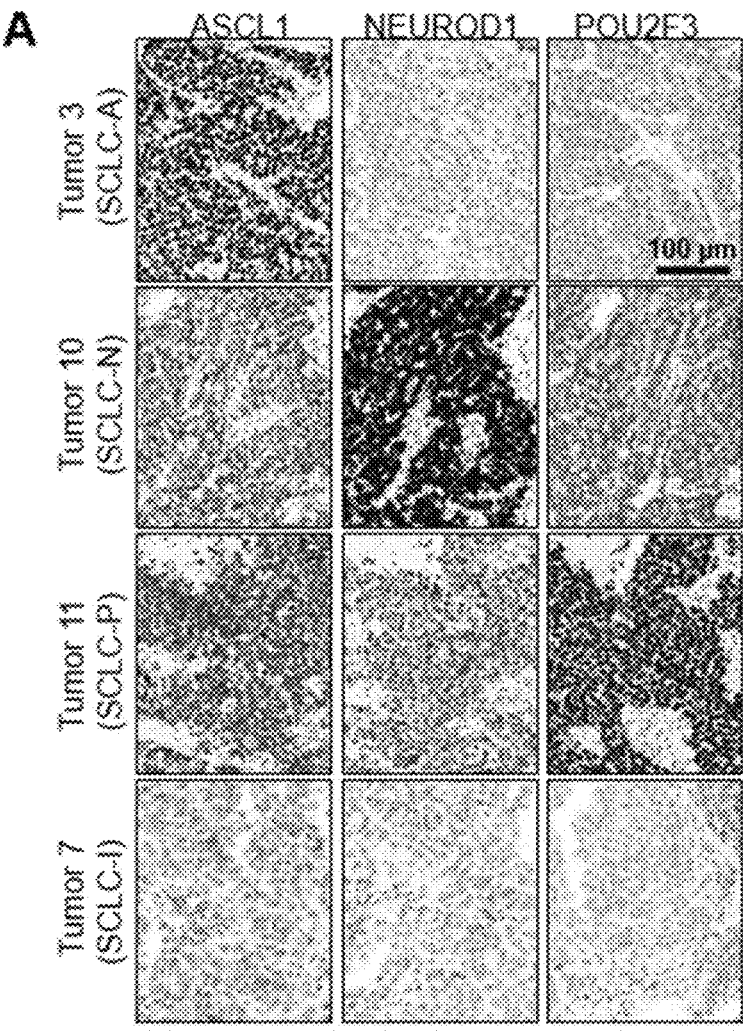

FIGS. 5A-N. Intratumoral heterogeneity of SCLC subtypes in tumors and tumor-derived models. Immunohistochemical (IHC) staining of consecutive sections of patient SCLC tumor for ASCL1, NEUROD1, and POU2F3 demonstrating staining pattern for example of each of four subtypes (A). Bar graph indicating percentage of tumor cell nuclei positive for ASCL1, NEUROD1, and POU2F3 by IHC in each of four tumors above (B). Spatially restricted IHC expression patterns of ASCL1 and NEUROD1 in heterogeneous tumor (C). t-SNE feature plots from single-cell RNAseq for ASCL1, NEUROD1, and absence of ASCL1/NEUROD1/POU2F3 (SCLC-I; triple negative) in representative CDX model of SCLC-A (MDA-SC16) (D) and SCLC-N(MDA-SC49) (E) subtypes. Heatmap highlighting differential methylation (beta value) of NEURON promoter both distal and proximal to transcriptional start site (TSS1500 and TSS200, respectively) in cell lines that express ASCL1-only, NEUROD1-only, or both (F). Comparison of mean fraction of SCLC-I (triple-negative) cells from single-cell RNAseq between CDXs derived from relapsed SCLC patients SCLC (relapsed) and those derived from never treated/currently frontline treated patients (frontline) (G). Expression of ASCL1, NEUROD1, and POU2F3, along with transcriptional targets of each, in individual cells of seven CTC-derived xenograft (CDX) models using single-cell RNAseq (H). t-SNE feature plots from single-cell RNAseq for ASCL1, NEUROD1, and absence of ASCL1/NEUROD1/POU2F3 ("triple negative") (I, K), as well as DLL3 (J, L) comparing parental MDA-SC68 CDX and cisplatin-resistant/relapsed MDA-SC68rel CDX models. Comparison of mean protein expression of Notch receptors NOTCH1 and NOTCH2 (M-N) across SCLC cell line subtypes.

FIGS. 6A-H: Emergence of SCLC-I populations coincides with cisplatin resistance in SCLC-A predominant xenograft models. t-SNE feature plots from single-cell RNAseq for ASCL1 comparing parental, treatment-naive and cisplatin-resistant/relapsed (cis-relapsed) CDX models (MDA-SC53, A; MDA-SC68, B). Highlighted portion of A and B illustrates distinct cluster with prominent ASCL1 loss (C, D). The cells in this region are now triple-negative (SCLC-I), with high EMT score (E, F), and expression of HLA genes (G, H).

FIGS. 7A-E: Differential expression NMF-identified genes (A) and, specifically, of ASCL1, NEUROD1, and POU2F3, across 3 subtype version of clustering analysis (B). Mean expression of YAP1 across SCLC tumor subtypes (C). Validation of four subtypes defined by gene expression of ASCL1, NEUROD1, POU2F3, or absence of all three in independent SCLC tumor (D) and SCLC cell line (E) cohorts.

FIGS. 8A-E: Comparison of mean protein expression of the epithelial marker CDH1 (A) and mesenchymal markers VIM and AXL (B-C) across SCLC cell line subtypes. Comparison of mean protein expression of lung tumor marker TTF1 (D) and p53 (E) across SCLC cell line subtypes.

FIGS. 9A-D: Frequency of mutations in 25 most frequently mutated in SCLC genes for tumors from each of the four subtypes (A-D).

FIGS. 10A-H: Comparison of mean tumor mutation frequency (defined as ratio of mutated genes to total genes) across SCLC tumor subtypes (A). Comparison of mean gene expression of various immune checkpoints (B-H) across SCLC tumor subtypes.

FIGS. 11A-F: Comparison of mean $IC_{50}$ values for in vitro treatment with cisplatin of SCLC cell lines from each subtype (A). Comparison of mean protein expression of predictive biomarkers including SLFN11, cMYC, and BCL2 (B-D) among SCLC cell lines. Expression of BTK gene among tumors of each subtype (E) and mean $IC_{50}$ values between subtypes for the BTK inhibitor ibrutinib (F). Differential mean expression of DLL3 protein among SCLC cell lines (G). Differential mean gene expression (H-J) among subtypes for DLL3 in tumor and cell lines data sets.

FIGS. 12A-F: Kaplan-Meier curves illustrating relapse-free (A) and overall survival (B) for patients with tumors of each subtype. Comparison of mean age at diagnosis (C) and smoking pack-years (D) for patients with tumors of each subtype. Comparison of fraction of male/female (E) and extensive-stage/limited-stage (F) for each subtype.

FIGS. 13A-B: Mean methylation beta-values of promoter region of NEUROD1 gene within 200 nucleotides (A) or 1500 nucleotides (B) from transcriptional start site (TSS) for cell lines classified as ASCL1-only (A-only), NEUROD1-only (N-only), or both.

Figure 14:
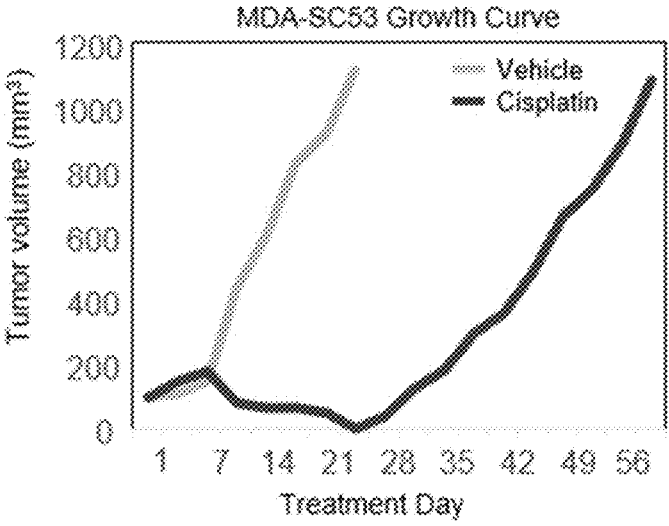

FIG. 14: Curves illustrating tumor growth in MDA-SC53 treated with vehicle (pink) or cisplatin (green), including subsequent growth following relapse and platinum resistance, prior to collection for single-cell RNAseq experiments. Similar curve for MDA-SC68 previously reported (Stewart et al., 2020b).

FIGS. 15A-F: t-SNE feature plots from single-cell RNAseq for YAP1 comparing parental, treatment-naive and cisplatin-resistant/relapsed (cis-relapsed) CDX models (MDA-SC53, A; MDA-SC68, B). t-SNE feature plots from single-cell RNAseq for triple-negative (TN)/SCLC-I cells, which lack ASCL1, NEUROD1, and POU2F3 (MDA-SC53, C; MDA-SC68, D). t-SNE feature plots from single-cell RNAseq for HLA-DQA1 (MDA-SC53, E; MDA-SC68, F).

FIGS. 16A-F: t-SNE feature plots from single-cell RNAseq for HES1, DLL3, and MYC comparing parental, treatment-naive and cisplatin-resistant/relapsed (cis-relapsed) CDX models (MDA-SC53, A, C, E; MDA-SC68, B, D, F).

Figure 17:
Figure 17:
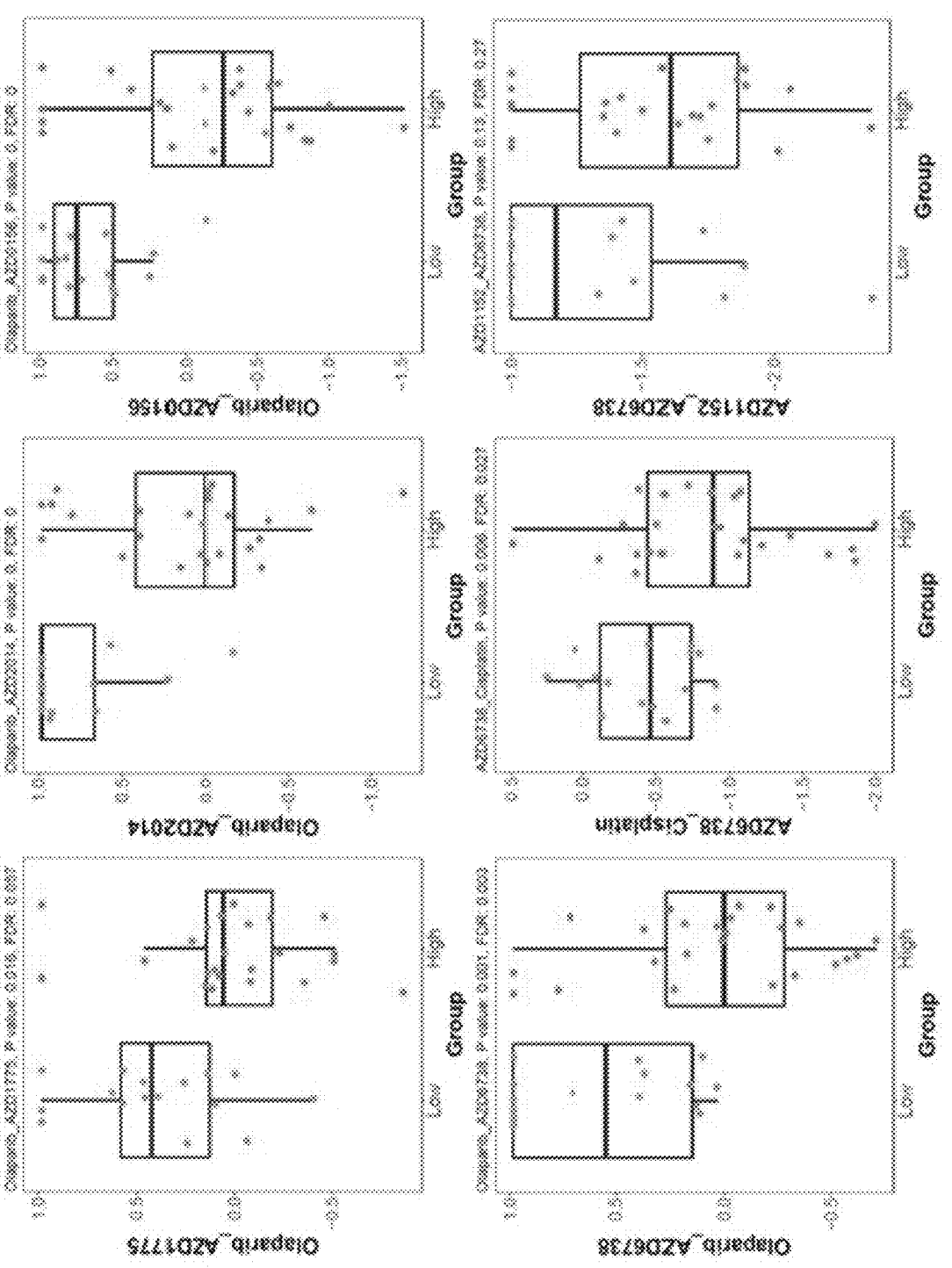

FIG. 17: Secondary subtype within SCLC-A possesses unique therapeutic vulnerabilities. Comparison between various SCLC-A cell lines having differing SLFN11 expression for sensitivity to PARP inhibitors, cisplatin, ATM inhibitors (e.g., AZD0156), ATR inhibitors (e.g., AZD6738), WEE1 inhibitors (e.g., AZD1775), mTOR inhibitors (e.g., AZD2014), and combinations thereof.

DETAILED DESCRIPTION

Accounting for 15% of all lung cancer diagnoses, small cell lung cancer (SCLC) is an aggressive malignancy with dismal clinical outcomes, due in part to failure to define clinical biomarkers predictive of unique, targetable vulnerabilities. Recent data has begun to delineate molecular subsets of SCLC by uncovering inter-tumoral heterogeneity in features such as DNA damage response, EMT, and neuroendocrine (NE) status. However, it remains unclear whether the subsets defined by these features are predictive of response to cancer therapies and could be employed as patient selection criteria.

Using RNAseq data from 81 resected SCLC tumor samples and 62 SCLC cell lines, non-negative matrix factorization (NMF) was used to optimize delineation of transcriptionally defined clusters. Reverse phase protein array (RPPA) and drug response data for cell lines were analyzed post-clustering to compare features between clusters. Clustering analyses were validated in vivo using CTC-derived patient xenograft (CDX) models, while single-cell RNAseq (scRNAseq) from these same models was used to assess intratumoral heterogeneity among clusters.

NMF identified four biologically distinct clusters among SCLC tumor samples and cell lines, each defined almost solely by differential expression of the transcription factors ASCL1 (SCLC-A), NEUROD1 (SCLC-N), and POU2F3 (SCLC-P), including a cluster defined by the absence of all three (SCLC-I, "Inflammed"). SCLC-A are neuroendocrine, epithelial tumors with susceptibility to drug classes including BCL-2 inhibitors. SCLC-N are neuroendocrine, cMYC-high tumors with susceptibilities including Aurora kinase inhibitors that are neither epithelial nor mesenchymal. SCLC-P are non-neuroendocrine, epithelial tumors vulnerable to PARP inhibitors, nucleoside analogs, anti-metabolites (e.g. pemetrexed), and platinum (cisplatin/carboplatin). Lastly, SCLC-I consists of mesenchymal, non-neuroendocrine tumors with high-expression of antigen presentation, immune checkpoint, and interferon-γ gene signatures that may represent those SCLC which are sensitive to immune checkpoint blockade. Categorization into these subtypes can be accurately recapitulated by immunohistochemical staining for the three transcription factors, as well as by DNA methylation profiles. Meanwhile, scRNAseq revealed intratumoral heterogeneity among cluster assignment within tumors that fluctuates coincident with the onset of therapeutic resistance.

SCLC tumors can be assigned to one of four molecular subtypes on the basis of differential expression of three transcription factors. These subtype assignments reflect profound distinctions in underlying biology and susceptibility to a range of candidate drug classes. While subtype assignment on a single-cell basis within a tumor is largely homogeneous, rare cells from distinct subtypes (or representing multiple subtypes), as well as shifting assignments following treatment indicate the possibility of subtype-switching, or subtype-selection, as mechanisms of therapeutic resistance.

I. Aspects of the Present Invention

SCLC has proven a recalcitrant challenge for the era of personalized cancer therapy due, at least in part, to under-appreciated inter- and intra-tumoral heterogeneity. Owing to their relatively increased frequency, highly neuroendocrine SCLC tumors driven by ASCL1 and NEUROD1, along with related factors such as cMYC and TTF1 expression, have been the source of many of the previous efforts to delineate intertumoral heterogeneity in SCLC (Carney et al., 1985; Gazdar et al., 1985; Zhang et al., 2018; Cardnell et al., 2017). The recent discovery of a variant of SCLC with a probable cell of origin as pulmonary tuft cells, in which POU2F3 is highly expressed (Huang et al., 2018), rather than pulmonary neuroendocrine cells, prompted further investigation as to how this new variant fits among the SCLC classifications and a general reevaluation of SCLC classification (Rudin et al., 2019). Toward this goal, the present findings represent the first comprehensive subclassification of SCLC to integrate gene and protein expression from multiple independent cohorts, with genetic, epigenetic, clinical, and drug response data.

While the present NMF and downstream analyses again identify SCLC-A and SCLC-N as the predominant subtypes, the results argue strongly that SCLC-P is a unique SCLC subtype with a largely distinct phenotype and distinct therapeutic vulnerabilities. Consistent with the hypothesis that SCLC-P does not originate from pulmonary neuroendocrine cells, these tumors have consistently low expression of neuroendocrine markers and high expression of the consensus non-neuroendocrine markers. While non-neuroendocrine SCLC, when described at all, has mostly been described as a single subtype (Zhang et al., 2018), a novel subtype described here, SCLC-I, is distinct from SCLC-P. Specifically SCLC-I exhibits higher expression of mesenchymal markers and an inflamed phenotype, with high expression of genes related to MHC, interferon-γ/STING pathway activation, and immune checkpoints, consistent with prior reports of the association between EMT and immune-related gene expression (Mak et al., 2016). Notably, the SCLC-I subtype is not defined by YAP1 expression, distinguishing this subtype from those proposed in other reports (Rudin et al., 2019). While this subtype is defined partly by its inflammatory features, the SCLC-I subtype is tumor intrinsic, as it is identified in systems devoid of tumor immune microenvironment, as in SCLC-I cell lines and SCLC-I populations in the present CDX experiments.

The translational implications of these four subtypes are significant, as each subtype demonstrates unique vulnerability to investigational therapies. Take, for instance, PARP inhibitors, for which high SLFN11 expression is the prevailing predictive biomarker at this time (Allison Stewart et al., 2017; Pietanza et al., 2018). While the highest SLFN11-expressing SCLC models are largely confined to the SCLC-A cohort and are sensitive to PARPi, it appears that selection of POU2F3 expressing tumors may capture a unique, SLFN11-independent cohort that is also sensitive to PARPi. Indeed, a recent study in which patient-derived xenografts (PDXs) were treated with the PARPi olaparib (plus temozolomide) in a murine co-clinical trial found the lone SCLC-P PDX model had the longest time to progression with both platinum+etoposide and olaparib+temozolomide (Farago et al., 2019). This provides additional support for the PARPi (and platinum) vulnerability of SCLC-P.

Alternatively, while ICB is now considered standard-of-care for SCLC, predictive biomarkers for this therapeutic class have remained elusive in this disease, with evidence supporting (and opposing) TMB and PD-L1 expression, to name a few (Chung et al., 2018; Hellmann et al., 2018). The present results suggest that SCLC-I captures several key features that are predictive of immune checkpoint inhibitor response in other tumors, including robust antigen presentation machinery, inflamed gene expression profile, and high expression of the immune checkpoint targets. In the largest data set, SCLC-I constitutes ~17% of all SCLC tumors, a comparable fraction to the response rates observed for ipilimumab/nivolumab (19-23%) and single-agent pembrolizumab (19%) in relapsed SCLC in CheckMate 032 (Antonia et al., 2016) and KEYNOTE-158 (Chung et al., 2020), respectively. Further, that SCLC-I is the most resistant subtype to conventional chemotherapies is consistent with data from Checkmate 331 suggesting preferential OS benefit for nivolumab (versus chemotherapy) in patients with platinum-resistant SCLC (Reck et al., 2018).

These data also provide some of the first insights as to the intratumoral heterogeneity of SCLC subtypes and how this might impact therapy selection and resistance. While bulk analyses often suggest that tumors and models are predominantly a single subtype, this is only sometimes true in higher resolution analyses. The present IHC suggests, for example, in some tumors, multiple subtypes are present in spatially distinct tumor locations. In these scenarios, a treatment tailored to a single subtype might yield a partial response that is quickly negated by the outgrowth of the non-targeted subtype—stressing the importance for careful evaluation of tumor subtype and consideration of combination therapies for instances of mixed subtypes. Many of the patient tumors and patient-derived xenograft tumors demonstrate subtler intra-tumoral heterogeneity, with small populations of cells identified as alternate subtypes amidst the dominant subtype.

Single-cell analyses reveal that intratumoral heterogeneity with respect to subtype may also be a dynamic process, as populations of more chemoresistant triple negative (SCLC-I) cells increase with platinum treatment. This could be the result of selection of pre-existing populations of SCLC-I cells that predate treatment or overt subtype switching from SCLC-A to SCLC-I. Several observations favor the latter scenario, most notably that in one of the two models (MDA-SC68), there are essentially no pre-existing SCLC-I cells that can be identified. In this case, the few cells that are triple negative lack other features of SCLC-I, such as HLA gene expression or high EMT score, and may instead reflect technical limitations of the single-cell RNAseq approach, including gene dropout. On the other hand, those triple-negative cells that emerge following relapse show consistent, robust features of SCLC-I. These data are consistent with recent evidence from single-cell RNAseq analysis of GEMM models showing subtype and phenotypic evolution or heterogeneity over developmental time (Ireland et al., 2020; Lim et al., 2017). Other in vitro data exploring NCI-H69 (a SCLC-A cell line), demonstrate the spontaneous appearance of a mesenchymal, inflamed descendent of this cell line in culture (Canadas et al., 2018). These data, however, link this switching phenomena to treatment and, specifically, platinum resistance—consistent with the fact that SCLC-I cells are markedly platinum resistant in vitro. The emergence of these SCLC-I cells, which may be therapeutically targetable via immune checkpoint blockade, may serve to explain the clinical benefit observed with combination chemoimmunotherapy in this disease (Horn et al., 2018; Paz-Ares et al., 2019).

Whether this is a case of natural selection of small fractions of SCLC-I cells that exist pre-treatment, or 'subtype switching' is unclear. It is essential to evaluate these subtype dynamics in samples from patients treated with these chemoimmunotherapy combinations to determine whether switching to other subtypes or the development of a novel subtype occurs on treatment or following relapse.

The present methylation data suggest that switching between SCLC-A and SCLC-N could be easily achieved via varied methylation of the NEUROD1 promoter or ASCL1 promoter, for example. This is compatible with evidence that increased expression and activity of epigenetic modifiers, such as EZH2, mediate resistance to platinum chemotherapy in SCLC. Constraining subtype switching, such as with an epigenetic modifier or Notch inhibitor, may be a feasible strategy to extend response to therapy. Alternatively, exploiting or even promoting subtype switching could be advantageous clinically, as well. Deliberate switching to SCLC-I, for instance, represents an option by which to express HLAs in an otherwise HLA-deficient tumor, which may overcome a key resistance mechanism to ICB.

Most SCLC tumors and models analyzed are easily classified into one of the four subtypes, permitting a realistic scenario in which prospective subtyping is performed in a single umbrella trial, wherein patients are assigned to a treatment arm (e.g., SCLC-I to combination ICB, SCLC-P to PARP inhibitors) on the basis of their SCLC subtype. Subtype could be determined by RNA-based signatures, as derived from the present NMF analyses, IHC for each of the three transcription factors, or even DNA methylation status of these transcription factors. This represents the first standard-of-care molecular biomarker selection for SCLC and a foundational step toward personalized therapy for this devastating disease.

II. Methods of Treatment and Methods of Detection

The present invention provides methods of treating a patient with small cell lung cancer. The methods involve identifying which of four subtypes of SCLC that the patient has based on the expression or methylation status of ASCL1, NEUROD1, and POU2F3. One subtype expresses ASCL1 but neither NEUROD1 nor POU2F3; a second subtype expresses NEUROD1 but neither ASCL1 nor POU2F3; a third subtype expresses POU2F3 but neither ASCL1 nor NEUROD1; a fourth subtype expresses none of ASCL1, NEUROD1, and POU2F3. The treatment for the patient is determined based on the subtype determination. Such treatment may also be in combination with another therapeutic regime, such as chemotherapy or immunotherapy. In addition, the treatment may be in combination due to the patient's cancer falling into more than one subtype, such as, for example, if one portion of the cancer's cell express ASCL1 and another portion of the cancer's cell express NEUROD1. The subtype of a given cancer may change over time as well, such that the present methods regarding identifying the subtype and selecting an appropriate treatment will need to be performed more than once, such as repeating the methods after a patient develops resistance to a selected therapy.

In various aspects, about 5%, 10%, 15%, 20%, 25%, 30%, 35%, 40%, 45%, 50%, 55%, 60%, 65%, 70%, 75%, 80%, 85%, 90%, 95%, or 100% of the cells that comprise the cancer may express ASCL1. In this case, the patient is selected for treatment with a BCL-2 inhibitor. Examples of BCL-2 and/or BCL-XL inhibitors include ABT-737, ABT-263 (navitoclax), ABT-199 (venetoclax), GX15-070 (obatoclax), HA14-1, TW-37, AT101, and BI-97C1 (sabutoclax). If the cells also express a high level of SLFN11, then the patient may be selected for treatment with a PARP inhibitor, cisplatin, ATM inhibitor (e.g., AZD0156), ATR inhibitor (e.g., AZD6738), WEE1 inhibitor (e.g., AZD1775), mTOR inhibitor (e.g., AZD2014), or a combination thereof. For example, the patient may be selected for treatment with a PARP inhibitor in combination with a second agent, such as, for example, AZD0156, AZD1775, AZD2014, or AZD6738. For example, the patient may be selected for treatment with cisplatin in combination with a second agent, such as, for example, AZD0156, AZD1775, AZD2014, or AZD6738. Examples of PARP inhibitors include olaparib, rucaparib, niraparib, talazoparib, veliparib, pamiparib, CEP 9722, E7016, iniparib, AZD2461, and 3-aminobenzamide.

In various aspects, about 5%, 10%, 15%, 20%, 25%, 30%, 35%, 40%, 45%, 50%, 55%, 60%, 65%, 70%, 75%, 80%, 85%, 90%, 95%, or 100% of the cells that comprise the cancer may express NEUROD1. In this case, the patient is selected for treatment with an Aurora kinase inhibitor, a JAK inhibitor, or a c-Met inhibitor. Examples of Aurora kinase inhibitors include alisertib, ZM447439, hesperidin, ilorasertib, VX-680, CCT 137690, lestaurtinib, NU 6140, PF 03814735, SNS 314 mesylate, TC-A 2317 hydrochloride, TAK-901, AMG-900, AS-703569, AT-9283, CYC-116, SCH-1473759, and TC-S 7010. Examples of JAK inhibitors include ruxolitinib, tofacitinib, oclacitinib, baricitinib, peficitinib, fedratinib, upadacitinib, filgotinib, cerdulatinib, gandotinib, lestaurtinib, momelotinib, pacritinib, and PF-04975842. Examples of c-Met inhibitors include BMS-777607, cabozantinib, MK-2461, AMG-458, JNJ-38877605, PF-04217903, and GSK-1363089. Other drugs to which patients having a cancer that expresses NEUROD1 may be sensitive include PF-562271, VS-507, KW-2449, pimozide, CB-64D, AC-220, omacetaxine mepasuccinate, XL-888, XL-880, ifosfamide, SL-0101, GW-5074, letrozole, CYC-202, and BIM-46187.

In various aspects, about 5%, 10%, 15%, 20%, 25%, 30%, 35%, 40%, 45%, 50%, 55%, 60%, 65%, 70%, 75%, 80%, 85%, 90%, 95%, or 100% of the cells that comprise the cancer may express POU2F3. In this case, the patient is selected for treatment with a PARP inhibitor, an AKT inhibitor, a Sky inhibitor, a JAK inhibitor, a SRC inhibitor, a BET inhibitor, an ERK inhibitor, an mTor inhibitor, an HSP90 inhibitor, a PI3K inhibitor, a CDK inhibitor, a topoisomerase inhibitor, a nucleoside analogue, an anti-metabolite, or a platinum-containing chemotherapeutic agent. Examples of PARP inhibitors include olaparib, rucaparib, niraparib, talazoparib, veliparib, pamiparib, CEP 9722, E7016, iniparib, AZD2461, and 3-aminobenzamide. Examples of AKT inhibitors include CCT-128930, GSK690693, MK 2206, SC79, capivasertib, ipatasertib, borussertib, uprosertib, perifosine, AZD-5363, and A-443654. Examples of Syk inhibitors include R-406, R-788 (fostamatinib), BAY 61-3606, and nilvadipine. Examples of JAK inhibitors include ruxolitinib, tofacitinib, oclacitinib, baricitinib, peficitinib, fedratinib, upadacitinib, filgotinib, cerdulatinib, gandotinib, lestaurtinib, momelotinib, pacritinib, AZD-1480, XL-019, SB-1578, WL-1034, and PF-04975842. Examples of SRC inhibitors include dasatinib, AZD-0530, KX2-391, bosutinib, saracatinib, and quercetin. Examples of BET inhibitors include GSK1210151A, GSK525762, (+)-JQ1, OTX-015, TEN-010, CPI-203, CPI-0610, LY294002, AZD5153, MT-1, and MS645. Examples of ERK inhibitors include SC-1 (pluripotin), AX 15836, BIX 02189, ERK5-IN-1, FR 180204, TCS ERK 11e, TMCB, and XMD 8-92. Examples of CDK inhibitors include R-547, palbociclib, LY-2835219, CYC-202, ribociclib, abemaciclib, and trilaciclib. Examples of mTor inhibitors include PF-04212384, OSI-027, rapamycin, AZD-2014, RG-7603, BGT-226, PI-103, GSK-2126458, everolimus, temsirolimus, ridaforolimus, sirolimus, dactolisib, and sapanisertib. Examples of anti-metabolites and nucleoside analogues include teriflunomide, pemetrexed, ONX-0801, fluorouracil, cladribine, methotrexate, mercaptopurine, gemcitabine, capecitabine, hydroxyurea, fludarabine, 2-fluoroadenosine, pralatrexate, nelarabine, cladribine, clofarabine, decitabine, azacitidine, cytarabine, floxuridine, and thioguanine. Examples of platinum-containing chemotherapeutic agents include cisplatin, carboplatin, oxaliplatin, nedaplatin, picoplatin, and satraplatin. Other drugs to which patients having a cancer that expresses POU2F3 may be sensitive include ENMD-2076, HPI-1, CP-868596, TL-32711, FGF inhibitor, AS-703569, vandetanib, CYC-116, KW-2499, GSK-2334470, BMS-582664, AEG-40730, ICG-001, CB-64D, SCH-1473759, MK-2461, CH-5132799, dovitinib, AM-2282, PP-242, ZSTK-474, crizotinib, apitolisib, AT-9283, MPC-3100, alisertib, LOR-253, INK-128, AZD-8055, omacetaxine mepasuccinate, everolimus, XL-888, XL-880, PF-04929113, PF-4942847, dactolisib, PF-04691502, TAK-901, CUDC-305, tretinoin, GSK-461364, BAY-80-6946, danorubicin, doxorubicin, valrubicin, YK-4-279, PF-4176340, BKM-120, APO-866, EB-1627, axitinib, XR-5944, XR-5000, BX-912, mitoxantrone, LY-294002, ixabepilone, GDC-0941, BMS-536924, 3-AP, thiotepa, belinostat, and ABT-348.

In various aspects, about 5%, 10%, 15%, 20%, 25%, 30%, 35%, 40%, 45%, 50%, 55%, 60%, 65%, 70%, 75%, 80%, 85%, 90%, 95%, or 100% of the cells that comprise the cancer may express none of ASCL1, NEUROD1, and POU2F3. These cells may express immune checkpoint proteins, inflammatory markers, STING pathway proteins, CCL5, CXCL10, MHC proteins, CD274 (PD-L1), LAG3, C10orf54 (VISTA), ID01, CD38, and ICOS. In this case, the patient is selected for treatment with an immune checkpoint inhibitor, a BTK inhibitor, a Syk inhibitor, a multikinase inhibitor, an ERK inhibitor, an VEGFR inhibitor, a MEK inhibitor, a FGFR inhibitor. Examples of BTK inhibitors include ibrutinib, LCB 03-0110, LFM-A13, PCI 29732, PF 06465469, and terreic acid. Examples of Syk inhibitors include R-406, R-788 (fostamatinib), BAY 61-3606, and nilvadipine. Examples of multikinase inhibitors include LY-2801653, ENMD-2076, ponatinib, and pazopanib. Examples of ERK inhibitors include SC-1 (pluripotin), AX 15836, BIX 02189, ERK5-IN-1, FR 180204, TCS ERK 11e, TMCB, and XMD 8-92. Examples of VEGFR inhibitors include ASP-4130 (tivozanib), lenvatinib, RG-7167, sorafenib, sunitinib, bevacizumab, cabozantinib, regorafenib, nintedanib, and apatinib. Examples of MEK inhibitors include RO-5126766, AZD-8330, TAK-733, XL-518, PD-0325901, ARRY-162, trametinib, pimasertib, cobimetinib, binimetinib, and selumetinib. Examples of FGFR inhibitors include AZD-4547, PD-173074, LY-2874455, BGJ-398, ponatinib, nintedanib, dovitinib, danusertib, and brivanib. Other drugs to which patients having a cancer that expresses none of ASCL1, NEUROD1, and POU2F3 may be sensitive include AZD-1480, AZD-0530, ASP-3026, fulvestrant, SCH-1473759, MK-2461, LY-2090314, PP-242, 17-AAG, BPR1J-097, INK-128, AZD-8055, omacetaxine mepasuccinate, everolimus, XL-888, XL-880, dactolisib, PF-04691502, OSI-027, rapamycin, CUDC-305, and bleomycin.

Immune checkpoints either turn up a signal (e.g., co-stimulatory molecules) or turn down a signal. Immune checkpoint proteins that may be targeted by immune checkpoint blockade include adenosine A2A receptor (A2AR), B7-H3 (also known as CD276), B and T lymphocyte attenuator (BTLA), CCL5, CD27, CD38, CD8A, CMKLR1, cytotoxic T-lymphocyte-associated protein 4 (CTLA-4, also known as CD152), CXCL9, CXCR5, glucocorticoid-induced tumour necrosis factor receptor-related protein (GITR), HLA-DRB1, ICOS (also known as CD278), HLA-DQA1, HLA-E, indoleamine 2,3-dioxygenase 1 (ID01), killer-cell immunoglobulin (KIR), lymphocyte activation gene-3 (LAG-3, also known as CD223), Mer tyrosine kinase (MerTK), NKG7, OX40 (also known as CD134), programmed death 1 (PD-1), programmed death-ligand 1 (PD-L1, also known as CD274), PDCD1LG2, PSMB10, STAT1, T cell immunoreceptor with Ig and ITIM domains (TIGIT), T-cell immunoglobulin domain and mucin domain 3 (TIM-3), and V-domain Ig suppressor of T cell activation (VISTA, also known as C10orf54). In particular, the immune checkpoint inhibitors target the PD-1 axis and/or CTLA-4.

The immune checkpoint inhibitors may be drugs, such as small molecules, recombinant forms of ligand or receptors, or antibodies, such as human antibodies (e.g., International Patent Publication WO2015/016718; Pardoll, Nat Rev Cancer, 12(4): 252-264, 2012; both incorporated herein by reference). Known inhibitors of the immune checkpoint proteins or analogs thereof may be used, in particular chimerized, humanized, or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

In some embodiments, a PD-1 binding antagonist is a molecule that inhibits the binding of PD-1 to its ligand binding partners. In a specific aspect, the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, a PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or an oligopeptide. Exemplary antibodies are described in U.S. Pat. Nos. 8,735,553, 8,354,509, and 8,008,449, all of which are incorporated herein by reference. Other PD-1 axis antagonists for use in the methods provided herein are known in the art, such as described in U.S. Patent Application Publication Nos. 2014/0294898, 2014/022021, and 2011/0008369, all of which are incorporated herein by reference.

In some embodiments, a PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence)). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342.

Another immune checkpoint protein that can be targeted in the methods provided herein is the cytotoxic T-lympho-cyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA-4 is similar to the T-cell co-stimulatory protein, CD28, and both molecules bind to CD80 and CD86, also called B7-1 and B7-2 respectively, on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a human-ized antibody, or a chimeric antibody), an antigen binding fragment thereof, an immunoadhesin, a fusion protein, or oligopeptide. Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in U.S. Pat. No. 8,119,129; PCT Publn. Nos. WO 01/14424, WO 98/42752, WO 00/37504 (CP675, 206, also known as tremelimumab; formerly ticilimumab); U.S. Pat. No. 6,207,156; Hurwitz et al. (1998) Proc Natl Acad Sci USA, 95(17): 10067-10071; Camacho et al. (2004) J Clin Oncology, 22(145): Abstract No. 2505 (antibody CP-675206); and Mokyr et al. (1998) Cancer Res, 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilim-umab. Accordingly, in one embodiment, the antibody comprises the CDR1, CDR2, and CDR3 domains of the VH region of ipilimumab, and the CDR1, CDR2, and CDR3 domains of the VL region of ipilimumab. In another embodiment, the antibody competes for binding with and/or binds to the same epitope on CTLA-4 as the above-mentioned antibodies. In another embodiment, the antibody has an at least about 90% variable region amino acid sequence identity with the above-mentioned antibodies (e.g., at least about 90%, 95%, or 99% variable region identity with ipilim-umab). Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

Another immune checkpoint protein that can be targeted in the methods provided herein is lymphocyte-activation gene 3 (LAG-3), also known as CD223. The complete protein sequence of human LAG-3 has the Genbank acces-sion number NP-002277. LAG-3 is found on the surface of activated T cells, natural killer cells, B cells, and plasma-cytoid dendritic cells. LAG-3 acts as an "off" switch when bound to MHC class II on the surface of antigen-presenting cells. Inhibition of LAG-3 both activates effector T cells and inhibitor regulatory T cells. In some embodiments, the immune checkpoint inhibitor is an anti-LAG-3 antibody (e.g., a human antibody, a humanized antibody, or a chimeric antibody), an antigen binding fragment thereof, an immu-noadhesin, a fusion protein, or oligopeptide. Anti-human-LAG-3 antibodies (or VH and/or VL domains derived there-from) suitable for use in the present methods can be generated using methods well known in the art. Alterna-tively, art recognized anti-LAG-3 antibodies can be used. An exemplary anti-LAG-3 antibody is relatlimab (also known as BMS-986016) or antigen binding fragments and variants thereof (see, e.g., WO 2015/116539). Other exemplary anti-LAG-3 antibodies include TSR-033 (see, e.g., WO 2018/201096), MK-4280, and REGN3767. MGD013 is an anti-LAG-3/PD-1 bispecific antibody described in WO 2017/019846. FS118 is an anti-LAG-3/PD-L1 bispecific antibody described in WO 2017/220569.

Another immune checkpoint protein that can be targeted in the methods provided herein is V-domain Ig suppressor of T cell activation (VISTA), also known as C10orf54. The complete protein sequence of human VISTA has the Gen-bank accession number NP_071436. VISTA is found on white blood cells and inhibits T cell effector function. In some embodiments, the immune checkpoint inhibitor is an anti-VISTA3 antibody (e.g., a human antibody, a humanized antibody, or a chimeric antibody), an antigen binding frag-ment thereof, an immunoadhesin, a fusion protein, or oli-gopeptide. Anti-human-VISTA antibodies (or VH and/or VL domains derived therefrom) suitable for use in the present methods can be generated using methods well known in the art. Alternatively, art recognized anti-VISTA antibodies can be used. An exemplary anti-VISTA antibody is JNJ-61610588 (also known as onvatilimab) (see, e.g., WO 2015/097536, WO 2016/207717, WO 2017/137830, WO 2017/175058). VISTA can also be inhibited with the small molecule CA-170, which selectively targets both PD-L1 and VISTA (see, e.g., WO 2015/033299, WO 2015/033301).

Another immune checkpoint protein that can be targeted in the methods provided herein is indoleamine 2,3-dioxy-genase (IDO). The complete protein sequence of human IDO has Genbank accession number NP_002155. In some embodiments, the immune checkpoint inhibitor is a small molecule IDO inhibitor. Exemplary small molecules include BMS-986205, epacadostat (INCB24360), and navoximod (GDC-0919).

Another immune checkpoint protein that can be targeted in the methods provided herein is CD38. The complete protein sequence of human CD38 has Genbank accession number NP_001766. In some embodiments, the immune checkpoint inhibitor is an anti-CD38 antibody (e.g., a human antibody, a humanized antibody, or a chimeric antibody), an antigen binding fragment thereof, an immunoadhesin, a fusion protein, or oligopeptide. Anti-human-CD38 antibod-ies (or VH and/or VL domains derived therefrom) suitable for use in the present methods can be generated using methods well known in the art. Alternatively, art recognized anti-CD38 antibodies can be used. An exemplary anti-CD38 antibody is daratumumab (see, e.g., U.S. Pat. No. 7,829, 673).

Another immune checkpoint protein that can be targeted in the methods provided herein is ICOS, also known as CD278. The complete protein sequence of human ICOS has Genbank accession number NP_036224. In some embodiments, the immune checkpoint inhibitor is an anti-ICOS antibody (e.g., a human antibody, a humanized antibody, or a chimeric antibody), an antigen binding fragment thereof, an immunoadhesin, a fusion protein, or oligopeptide. Anti-human-ICOS antibodies (or VH and/or VL domains derived therefrom) suitable for use in the present methods can be generated using methods well known in the art. Alternatively, art recognized anti-ICOS antibodies can be used. Exemplary anti-ICOS antibodies include JTX-2011 (see, e.g., WO 2016/154177, WO 2018/187191) and GSK3359609 (see, e.g., WO 2016/059602).

Another immune checkpoint protein that can be targeted in the methods provided herein is T cell immunoreceptor with Ig and ITIM domains (TIGIT). The complete protein sequence of human TIGIT has Genbank accession number NP_776160. In some embodiments, the immune checkpoint inhibitor is an anti-TIGIT antibody (e.g., a human antibody, a humanized antibody, or a chimeric antibody), an antigen binding fragment thereof, an immunoadhesin, a fusion protein, or oligopeptide. Anti-human-TIGIT antibodies (or VH and/or VL domains derived therefrom) suitable for use in the present methods can be generated using methods well known in the art. Alternatively, art recognized anti-TIGIT antibodies can be used. An exemplary anti-TIGIT antibody is MK-7684 (see, e.g., WO 2017/030823, WO 2016/028656).

Another immune checkpoint protein that can be targeted in the methods provided herein is OX40, also known as CD134. The complete protein sequence of human OX40 has Genbank accession number NP_003318. In some embodiments, the immune checkpoint inhibitor is an anti-OX40 antibody (e.g., a human antibody, a humanized antibody, or a chimeric antibody), an antigen binding fragment thereof, an immunoadhesin, a fusion protein, or oligopeptide. Anti-human-OX40 antibodies (or VH and/or VL domains derived therefrom) suitable for use in the present methods can be generated using methods well known in the art. Alternatively, art recognized anti-OX40 antibodies can be used. An exemplary anti-OX40 antibody is PF-04518600 (see, e.g., WO 2017/130076). ATOR-1015 is a bispecific antibody targeting CTLA4 and OX40 (see, e.g., WO 2017/182672, WO 2018/091740, WO 2018/202649, WO 2018/002339).

Another immune checkpoint protein that can be targeted in the methods provided herein is glucocorticoid-induced tumour necrosis factor receptor-related protein (GITR), also known as TNFRSF18 and AITR. The complete protein sequence of human GITR has Genbank accession number NP_004186. In some embodiments, the immune checkpoint inhibitor is an anti-GITR antibody (e.g., a human antibody, a humanized antibody, or a chimeric antibody), an antigen binding fragment thereof, an immunoadhesin, a fusion protein, or oligopeptide. Anti-human-GITR antibodies (or VH and/or VL domains derived therefrom) suitable for use in the present methods can be generated using methods well known in the art. Alternatively, art recognized anti-GITR antibodies can be used. An exemplary anti-GITR antibody is TRX518 (see, e.g., WO 2006/105021).

A. Detection

In some aspects, the present disclosure concerns immunodetection methods for detecting expression of ASCL1, NEUROD1, and POU2F3. A wide variety of assay formats are contemplated for detecting protein products, including immunohistochemistry, enzyme linked immunosorbent assay (ELISA), radioimmunoassay (RIA), immunoradiometric assay, fluoroimmunoassay, chemiluminescent assay, bioluminescent assay, dot blotting, FACS analyses, and Western blot to mention a few. The steps of various useful immunodetection methods have been described in the scientific literature. In general, the immunobinding methods include obtaining a sample of the cancer, and contacting the sample with an antibody specific for the protein to be detected, as the case may be, under conditions effective to allow the formation of immunocomplexes. In general, the detection of immunocomplex formation is well known in the art and may be achieved through the application of numerous approaches. These methods are generally based upon the detection of a label or marker, such as any of those radioactive, fluorescent, biological and enzymatic tags. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

With regard to detecting expression of mRNA products, or a corresponding cDNA, mRNA is first extracted from the cancer cells. The extracted mRNA may be amplified prior to detection. Alternatively, the extracted mRNA may be reverse transcribed to cDNA prior to amplification of the cDNA. Any nucleic acid amplification assay which can be utilized, including but not limited to the polymerase chain reaction (RT-PCR), branched DNA signal amplification, ligase chain reaction, isothermal nucleic acid sequence based amplification (NASBA), Q-beta replication, transcription-based amplification, amplifiable RNA reporters, boomerang DNA amplification, strand displacement activation, cycling probe technology, and other self-sustained sequence replication assays, as well as variations on these including methods for nucleic acid enrichment such as by using restriction digestion with polymerase chain reaction and the use of nested primers. Similarly, any method capable of detecting an amplified nucleic acid product, including but not limited to agarose gel electrophoresis, fluorescence-based detection methods, real-time PCR, ELISA detection methods, electrochemiluminescence, high performance liquid chromatography, reverse dot blot methods, and nucleic acid sequencing methods, may be used.

With regard to detecting methylation of a gene, there are mainly techniques known which are used for the detection of the methylation of gene. The methylation status of specific CpG dinucleotides can be determined using isoschizomers of bacterial restriction endonucleases which are characterized by different sensitivities vis-à-vis 5-methylcytosine. Examples thereof are the enzymes HpaII and MspI—both cut CCGG sequences, HpaII however only if the internal cytosine is not methylated. The treatment of double-stranded genomic DNA with sodium bisulfate leads to the deamination of unmethylated cytosine residues into uracil residues and to the formation of two single strands that are no longer complementary. During this treatment, 5-methyl cytosine is maintained. The differences in sequence produced in this way form the basis of the differentiation between methylated and unmethylated DNA. DNA treated with bisulfite can be used directly in PCR in which uracil residues (previously unmethylated cytosine) and thymidine residues are amplified as thymidine and only 5-methylcytosine residues are amplified as cytosine residues. Depending on the application, the primers used for the PCR differentiate between methylated and unmethylated sequences or amplify fragments independently of the methylation status. PCR fragments which have been amplified using non-discriminating primers can, for instance, be sequenced directly to determine the share in methylated and unmethylated CpGs. Antibodies against 5-methyl cytosine recognize CpG methylation in denatured, single-stranded DNA are used mainly for the immunohistochemical staining of the CpG methylation on the chromosomes of individual, fixed cells.

As used herein, the term "sample" refers to any sample suitable for the detection methods provided by the present invention. The sample may be any sample that includes material suitable for detection or isolation. Sources of samples include blood, pleural fluid, peritoneal fluid, urine, saliva, malignant ascites, broncho-alveolar lavage fluid, synovial fluid, and bronchial washes. In one aspect, the sample is a blood sample, including, for example, whole blood or any fraction or component thereof. A blood sample suitable for use with the present invention may be extracted from any source known that includes blood cells or components thereof, such as venous, arterial, peripheral, tissue, cord, and the like. For example, a sample may be obtained and processed using well-known and routine clinical methods (e.g., procedures for drawing and processing whole blood). In one aspect, an exemplary sample may be peripheral blood drawn from a subject with cancer. In some aspects, the biological sample comprises a plurality of cells. In certain aspects, the biological sample comprises fresh or frozen tissue. In specific aspects, the biological sample comprises formalin fixed, paraffin embedded tissue. In some aspects, the biological sample is a tissue biopsy, fine needle aspirate, blood, serum, plasma, cerebral spinal fluid, urine, stool, saliva, circulating tumor cells, exosomes, or aspirates and bodily secretions, such as sweat. In some aspects, the biological sample contains cell-free DNA.

B. Treatment

The term "subject" or "patient" as used herein refers to any individual to which the subject methods are performed. Generally the patient is human, although as will be appreciated by those in the art, the patient may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of patient.

"Treatment" and "treating" refer to administration or application of a therapeutic agent to a subject or performance of a procedure or modality on a subject for the purpose of obtaining a therapeutic benefit of a disease or health-related condition. For example, a treatment may include administration chemotherapy, immunotherapy, radiotherapy, performance of surgery, or any combination thereof.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the invasiveness of a tumor, reduction in the growth rate of the cancer, or prevention of metastasis. Treatment of cancer may also refer to prolonging survival of a subject with cancer.

Likewise, an effective response of a patient or a patient's "responsiveness" to treatment refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse. For example, an effective response can be reduced tumor size or progression-free survival in a patient diagnosed with cancer.

Regarding neoplastic condition treatment, depending on the stage of the neoplastic condition, neoplastic condition treatment involves one or a combination of the following therapies: surgery to remove the neoplastic tissue, radiation therapy, and chemotherapy. Other therapeutic regimens may be combined with the administration of the anticancer agents, e.g., therapeutic compositions and chemotherapeutic agents. For example, the patient to be treated with such anti-cancer agents may also receive radiation therapy and/or may undergo surgery.

For the treatment of disease, the appropriate dosage of a therapeutic composition will depend on the type of disease to be treated, as defined above, the severity and course of the disease, previous therapy, the patient's clinical history and response to the agent, and the discretion of the physician. The agent may be suitably administered to the patient at one time or over a series of treatments.

C. Combination Therapy

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. A tissue, tumor, or cell can be contacted with one or more compositions or pharmacological formulation(s) comprising one or more of the agents or by contacting the tissue, tumor, and/or cell with two or more distinct compositions or formulations. Also, it is contemplated that such a combination therapy can be used in conjunction with radiotherapy, surgical therapy, or immunotherapy.

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few hours apart, or a few days apart.

An anti-cancer first treatment may be administered before, during, after, or in various combinations relative to a second anti-cancer treatment. The administrations may be in intervals ranging from concurrently to minutes to days to weeks. In embodiments where the first treatment is provided to a patient separately from the second treatment, one would generally ensure that a significant period of time did not expire between the time of each delivery, such that the two compounds would still be able to exert an advantageously combined effect on the patient. In such instances, it is contemplated that one may provide a patient with the first therapy and the second therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a subtype-specific anti-cancer therapy is "A" and another anti-cancer therapy is "B":

| | | | | | |
|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A |
| B/A/B/A | B/A/A/B | A/A/A/B | B/A/A/A | A/B/A/A | A/A/B/A |

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammalI and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DFMO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.
3. Immunotherapy The skilled artisan will understand that additional immunotherapies may be used in combination or in conjunction with methods of the invention. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, Infection Immun., 66(11):5329-5336, 1998; Christodoulides et al., Microbiology, 144(Pt 11):3027-3037, 1998); cytokine therapy, e.g., interferons α, β, and γ, IL-1, GM-CSF, and TNF (Bukowski et al., Clinical Cancer Res., 4(10):2337-2347, 1998; Davidson et al., J. Immunother., 21(5):389-398, 1998; Hellstrand et al., Acta Oncologica, 37(4):347-353, 1998); gene therapy, e.g., TNF, IL-1, IL-2, and p53 (Qin et al., Proc. Natl. Acad. Sci. USA, 95(24):14411-14416, 1998; Austin-Ward and Villaseca, Revista *Medica* de Chile, 126(7):838-845, 1998; U.S. Pat. Nos. 5,830,880 and 5,846,945); and monoclonal antibodies, e.g., anti-CD20, anti-ganglioside GM2, and anti-p185 (Hanibuchi et al., Int. J. Cancer, 78(4):480-485, 1998; U.S. Pat. No. 5,824,311). It is contemplated that one or more anti-cancer therapies may be employed with the antibody therapies described herein.

In some embodiment, the immune therapy could be adoptive immunotherapy, which involves the transfer of autologous antigen-specific T cells generated ex vivo. The T cells used for adoptive immunotherapy can be generated either by expansion of antigen-specific T cells or redirection of T cells through genetic engineering. Isolation and transfer of tumor specific T cells has been shown to be successful in treating melanoma. Novel specificities in T cells have been successfully generated through the genetic transfer of transgenic T cell receptors or chimeric antigen receptors (CARs). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. CARs have successfully allowed T cells to be redirected against antigens expressed at the surface of tumor cells from various malignancies including lymphomas and solid tumors.

In one embodiment, the present application provides for a combination therapy for the treatment of cancer wherein the combination therapy comprises adoptive T cell therapy and a checkpoint inhibitor. In one aspect, the adoptive T cell therapy comprises autologous and/or allogenic T-cells. In another aspect, the autologous and/or allogenic T-cells are targeted against tumor antigens.
4. Surgery Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.
5. Other Agents It is contemplated that other agents may be used in combination with certain aspects of the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs)

inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

III. Kits

Kits are envisioned containing diagnostic agents, therapeutic agents, and/or other therapeutic and delivery agents. The kit may comprise reagents capable of use in determining the expression of at least ASCL1, NEUROD1, and POU2F3. The kit may also comprise a suitable container means, which is a container that will not react with components of the kit, such as an eppendorf tube, a syringe, a bottle, or a tube. The container may be made from sterilizable materials such as plastic or glass. The kit may further include an instruction sheet that outlines the procedural steps of the methods, such as the same procedures as described herein or are otherwise known to those of ordinary skill.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Statistical Analyses. Non-negative matrix factorization (NMF) algorithm (Skoulidis et al., 2015) with the following criteria for gene selection: gene expression bimodal index $\geq 1.5$, mean expression value $\geq 25$th percentile, and standard deviation of expression value $\geq 50$th percentile was utilized to identify the optimal number of clusters for SCLC tumor data set. Generalized linear model via penalized maximum likelihood (glmnet R package) was applied to identify markers, and then performed hierarchical clustering using these selected markers to the independent SCLC tumor and cell line cohorts. ANOVA was used to compare molecular profiling data including gene and protein expression, EMT score, and drug response data. Fisher's exact test was used to compute the association between categorical clinical variables and mutations with each subtype. Log rank test was used to compare the Kaplan-Meier RFS and OS curves. Data statistics and bioinformatics analyses were performed using R (available on the world wide web at r-project.org/) and Bioconductor packages (available on the world wide web at bioconductor.org/).

Gene and protein expression. Gene expression data included publicly available data for SCLC tumors and cell lines (George et al., 2015; Sato et al., 2013; Polley et al., 2016). Protein expression was assessed for ~200 total and phosphor-proteins in SCLC cell lines by RPPA as previously described (Byers et al., 2012). Lung-specific EMT score was calculated using gene expression values as previously described (Byers et al., 2013).

Drug response data. With the exception of cisplatin (Allison Stewart et al., 2017; Gay et al., 2019), drug response data included publicly available data sets (Polley et al., 2016). For cisplatin, cell lines were plated at 2,000 cells per well in 96-well plates 24 hours prior to treatment with drug using standard cell culture conditions. Each line was treated, in triplicate, with cisplatin at starting concentration of 10 μmon followed by 1:3 serial dilutions and DMSO-only control. Following 120-hour incubations, cell viability was assessed using CellTiter-Glo Luminescent Cell Viability Assay (Promega). $IC_{50}$ values were estimated using software program drexplorer with fitting of multiple dose-response models and selection of best model using the residual standard error.

DNA methylation. For the methylation analysis, data was retrieved from and the NCI Small Cell Lung Cancer Screening Project (Polley et al., 2016). Data was analyzed using R v3.6.3 (R Foundation for Statistical Computing, Vienna, Austria).

SCLC cell line DNA methylation data was generated using Infinium HumanMethylation450 BeadChip array that targets >450,000 methylation sites. The scanner data and image output files were managed with the Illumina Beadstudio Methylation Module. The normalized measurements presented as methylation β values, represent the degree of methylation at each methylation site, with 0 being unmethylated, and 1 being fully methylated.

Rank correlations and associated p-values were computed for each gene between the degree of methylation and the associated RNA_seq gene expression measurements. Chromosomes X and Y were excluded from the analysis. Any probe that was consistently unmethylated across all cell lines was also excluded (the average β-value $\leq 0.25$ across all cell line measurements). To correct for multiple hypothesis testing, Benjamini—Hochberg method was used to control false discovery rate. Adjusted p-value=0.05 and p<0 were applied in order to identify the set of Gene Regulated by Methylation (GRM). The set of GRM genes have statistically significant correlation in the degree of methylation and the associated mRNA expression level. Genes regulated by methylation (GRMs) were defined as genes whose expression is significantly anti-correlated with methylation β-values for sites associated with that gene (including promoter, untranslated regions, and gene body) (Lin et al., 2014). Cell lines analyzed included 20 from SCLC-A, 5 from SCLC-N, 2 from SCLC-I, and 1 from SCLC-P. As the latter two subtypes were underrepresented, the comparison was restricted to SCLC-A and SCLC-N.

Histology and immunohistochemistry. Patients were consented to tissue collection protocol LAB90-020 ("Molecular Approaches to Novel Therapies for Cancer: Research Repository of Normal and Neoplastic Tissues"). Tissue, once collected, was reviewed by staff thoracic pathologist to confirm SCLC.

Consecutive four-micrometer-thick tissue sections were cut from formalin-fixed paraffin embedded (FFPE) tissue for immunohistochemistry. IHC staining was performed with a Bond Max automated staining system (Leica Microsystems Inc., Vista, CA) using standard automated protocols. Leica Bond Retrieval Solution #2 (Leica Biosystems, equivalent to EDTA, pH 9.0) for 20 minutes was used for epitope retrieval. The primary antibody (ASCL1: 1:100, Clone 24B72D11.1, 556604, BDBiosciences, San Jose, CA; NEUROD1: 1:100 Clone EPR20766, ab213725, Abcam, Cambridge, UK; and POU2F3: 1:200, polyclonal, NBP1-83966, Novus Biologicals, Centennial, CO, USA) was incubated for 15 minutes at room temperature and detected using the Bond Polymer Refine Detection kit (Leica Biosystems) with DAB as chromogen. FFPE cell lines pellets with known protein expression of ASCL1, NEUROD1, and POU2F3 were used to establish the above optimal IHC conditions and assess sensitivity and specificity for each antibody. Positive tumor cells and H-scores were calculated as described previously (Pietanza et al., 2018).

Circulating-tumor cell derived xenograft model generation. Patients diagnosed with SCLC at the University of Texas MD Anderson Cancer Center were selected on the basis of extensive-stage disease irrespective of age, gender or other clinical criteria. These patients underwent informed consent to Institutional Review Board (IRB)-approved protocol LAB10-0442 ("Evaluation of blood-based test for the detection of circulating tumor cells and circulating proteins and microRNAs and molecular analysis for polymorphisms and mutations") and blood was collected. Technical details are as previously described (Stewart et al., 2020b). One vial of blood was collected for isolation and banking of plasma and peripheral blood mononuclear cells for use as a normal control. Ten milliliters of blood collected in EDTA vials was used for isolation of CTCs according to a previously published protocol (Hodgkinson et al., 2014). CTCs were isolated within 24 h of sample collection. Briefly, whole blood was incubated with RosetteSep™ CTC Enrichment Cocktail Containing Anti-CD36 (Stemcell Technologies) and layered over a Ficoll gradient. The CTC layer was isolated, cells were spun down, mixed 1:1 with Matrigel and injected subcutaneously into the flank of NOD.Cg-Prkdcscid Il2rgtmlWjl/SzJ (NSG) mice. Mice were monitored for formation of a flank tumor and were euthanized when tumor burden reached 1000-1500 mm³. Pieces of the tumor were fixed in paraformaldehyde for histological analyses, snap frozen in liquid nitrogen for genetic and proteomic analyses, viably frozen in 10% DMSO in FBS for future use, and transplanted into the flank of athymic nude mice for CDX model maintenance. CDX models were maintained in vivo by serial transplantation of tumors and all analyses performed to date were from passages ≤4. CDXs were derived from extensive-stage (ES) patients at different points of their treatment course.

Cisplatin-relapsed variations of two models (MDA-SC53 and MDA-SC68) were generated as previously described (Stewart et al., 2020b). Briefly, after transplanted tumors reached 120-150 mm³ vehicle was administered intraperitoneally once per week or cisplatin 4-6 mg/kg was administered intraperitoneally once per week. For treatment naïve tumors were harvested after they reached 1,000 mm³ for single-cell RNAseq. For cisplatin relapse, treatment was briefly halted at maximal response until tumors again reached 150 mm³, at which point it was resumed until tumor volume reached 1,000 mm³, at which point tumors were harvested and processed for single-cell RNAseq.

Mice used for establishment of CDX models were 6 week old female NSG mice from Jackson Labs, while maintenance of CDX models and drug treatment studies were performed using 6 week old female athymic nude mice from Envigo. All animals were maintained in accordance with the Institutional Animal Care and Use Committee of the MD Anderson Cancer Center and the NIH Guide for the Care and Use of Laboratory animals.

Single-cell RNAseq. Tumors were harvested from mice directly into cold tissue storage solution (MACS) and shipped overnight. The next day, tumors were processed by enzymatic dissociation with Collagenase IV (600 U/mL) and DNAse (2 μg/mL) for a maximum of 45 min and neutralized in collection buffer (1% BSA, 10% FBS, 2 mM EDTA in RPMI). Circulating tumor cells were isolated from blood samples on a Ficoll gradient. Dissociated cells were spun down and treated with ACK lysis buffer (A1049201, GIBCO) for 3 min on ice and washed with collection buffer. Cells were then stained for anti-human HLA A647 (Biolegend 311414), Calcein AM (C3100MP) and DAPI (Lifetech D1306, 1 μg/mL) and sorted by Fluorescence-Activated Cell sorting (FACS) to select only live, human cells for downstream single cell transcriptomic analyses. Sorted cells were washed once with 0.04% BSA in PBS and counted on Countess II automated cell counter (ThermoFisher). 12,200 cells were loaded per lane on the 10× Chromium platform and processed for cDNA synthesis and library preparation as per manufacturer's protocol using version 2 chemistry. cDNA and libraries were checked for quality on Agilent 4200 Tapestation and quantified by KAPA qPCR before sequencing on a single lane of a HiSeq4000 (Illumina).

Cell Ranger v2.0 was used to convert Illumina base call files to FASTQ files. These FASTQ files were aligned to the hg19 human reference genome and transcriptome provided by 10× genomics. The gene vs cell count matrix from Cell Ranger was used for downstream analysis. The raw reads were processed using the Cell Ranger pipeline to obtain the UMI (unique molecular identifier). CDX samples from the same model were pooled together. Cells that have less than 3,000 expressed genes were filtered out, and genes that were expressed in less than 10% cells were also filtered out. After filtering, each CDX model was down-sampled to 2,000 for inter-model comparison. The UMI counts were transformed and normalized using the SEURAT package v2.3.1 (Butler et al., 2018). Cell cycle effects were adjusted by regressing out the G2M and S phase gene expression scores using "ScaleData( )" function in SEURAT. Principle component analysis (PCA) was performed using the highly variable genes that were identified by SEURAT function "FindVariableGenes( )". The first seven principal components were used for clustering and tSNE transformation, representing 63.7%~66.4% of total variances. Cell populations were identified using the SEURAT "FindClusters( )" function with resolution set to 0.6.

Example 1— Defining the Transcriptional Subtypes of SCLC

Using previously published RNA-sequencing (RNAseq) data from 81 surgically resected SCLC tumors (George et al., 2015), non-negative matrix factorization (NMF) was applied (Skoulidis et al., 2015) in an unbiased attempt to identify SCLC subtypes. Maximization of cophenetic correlation values was used to select the optimal number of distinct gene expression-derived clusters, with both three cluster and four cluster options possessing virtually equivalent cophenetic correlation values approaching 1.0 (FIG. 1A). Both the three cluster and four cluster options included nearly identical groups with high ASCL1 (SCLC-A) or high NEUROD1 (SCLC-N) (FIGS. 1B, 1C, 7A, 7B). However, the four-cluster option was able to separate the remaining tumors into a POU2F3 (SCLC-P) subgroup and a distinct group of SCLC tumors negative for all three transcription factors ("triple negative") (FIGS. 1B, 1C, 5A, 5B). Differential expression of ASCL1, NEUROD1, and POU2F3 (FIG. 1C) along with subsequent analyses support SCLC-P and this triple negative subtype as biologically distinct and, thus, the four-cluster approach was preferred.

Figure 1G:
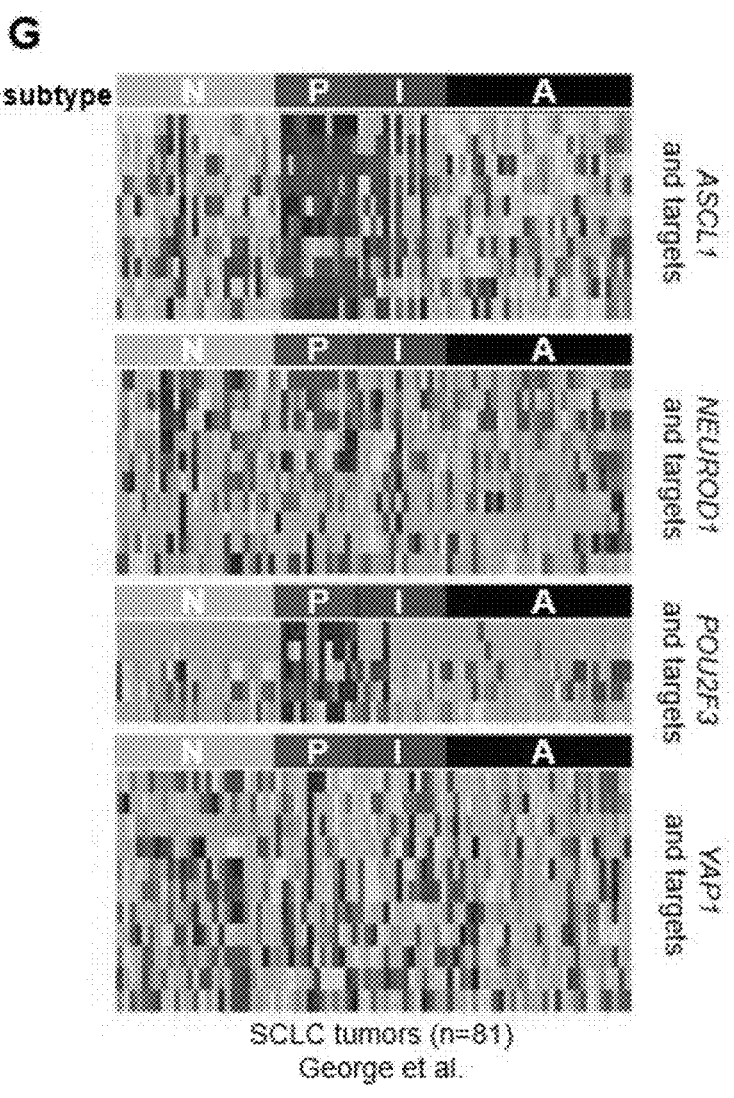

Among the NMF-defined gene lists for each subtype, differential expression was observed not only of each transcription factor (FIGS. 1C-F), but of their transcriptional targets (FIG. 1G) (Borromeo et al., 2016; Huang et al., 2018). In the triple negative subtype, no prevailing transcriptional signature emerges from the defining gene list and, instead, the uniquely expressed genes from the NMF include numerous immune checkpoints, human leukocyte antigens, and other immune associated genes. As such, this subtype was designated SCLC-inflamed, or SCLC-I. SCLC tumors were not equally distributed across the four subtypes, instead demonstrating proportions as follows: SCLC-A—36%, SCLC-N—31%, SCLC-I—17%, and SCLC-P—16%. Previously, in addition to the three transcription factor-defined subtypes (SCLC-A, -N, and -P), a fourth subtype defined by the transcription factor YAP1 had been proposed (Rudin et al., 2019). However, a consistent enrichment of YAP1 and its transcriptional targets was not observed in the triple negative subtype (FIG. 1G). YAP1 expression (FIG. 7C) and the expression of its transcriptional targets (FIG. 1G) was higher in both SCLC-P and SCLC-I compared to the other two subtypes. However, the SCLC-P and SCLC-I subtypes possess comparable mean expression of YAP1 and none of the four subtypes was found to be specifically defined by YAP1 expression.

While transcriptionally characterized SCLC data sets are rare, the four subtypes were validated in independent cohorts, including RNA microarray data from 23 SCLC tumor samples (Sato et al., 2013) (FIG. 7D) and RNAseq from 62 SCLC cell lines (Stewart et al., 2020a) (FIG. 7E). These analyses confirm the presence of all four subtypes, in varying proportions, in both validation cohorts.

Example 2— Defining Features of Transcriptional Subtypes

Figure 2A:
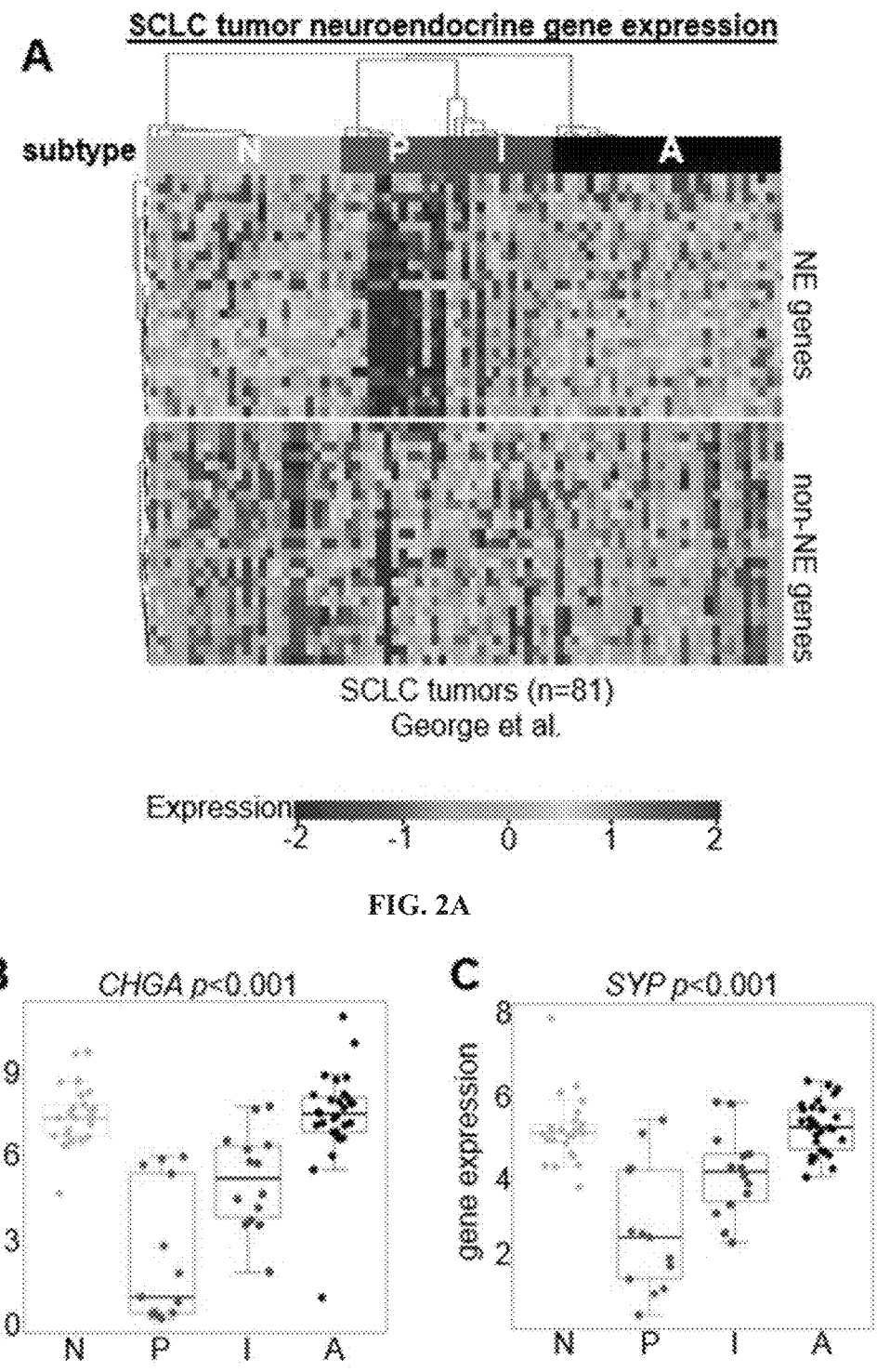

Recent investigations into SCLC phenotypes have focused on distinguishing between neuroendocrine (NE) and non-neuroendocrine (non-NE) SCLC varieties. Using previously defined NE and non-NE gene lists (Zhang et al., 2018), a clear distinction between NE subtypes (SCLC-A and -N) and non-NE subtypes (SCLC-P and -I) was observed (FIG. 2A). For example, SCLC-A and -N have significantly higher expression of two commonly assessed neuroendocrine markers, Chromogranin A (CHGA) and Synaptophysin (SYP) (FIGS. 2B-C), while REI Silencing Transcription Factor (REST), which is known to repress the expression of neuroendocrine genes (Lim et al., 2017), is significantly higher in both SCLC-P and -I (FIG. 2D).

While SCLC is generally considered an epithelial malignancy, epithelial-mesenchymal transition (EMT) has been proposed as potential mechanism of resistance in this disease (Bottger et al., 2019; Allison Stewart et al., 2017). Using a previously validated EMT score wherein more positive values indicate mesenchymal differentiation (Byers et al., 2013), SCLC-I is the most mesenchymal and SCLC-A is the most epithelial (FIG. 2E). Reverse-phase protein array (RPPA) data which quantify the expression of over 200 cancer-related total and phospho-proteins for all 62 SCLC cell lines supports this conclusion, as SCLC-I express very low levels of the epithelial marker E-cadherin (CDH1) and high levels of mesenchymal markers Vimentin (VIM) and AXL (FIGS. 8A-C).

Thyroid-transcription factor 1 (TTF1) expression is variable across SCLC tumors and has been proposed to define distinct SCLC subsets (Cardnell et al., 2017). Proteomic analysis of the SCLC cell lines demonstrates that the majority of TTF1-positive SCLC models fall within the SCLC-A subtype (FIG. 8D), consistent with NKX2-1 (the gene form of TTF1) as a known transcriptional target of ASCL1 (Borromeo et al., 2016).

Whole genome sequencing efforts revealed a high mutation rate in SCLC and near universal loss of TP53 and RB1 (George et al., 2015). However, efforts to identify and validate actionable mutations for SCLC patient treatment have yielded few prospects. Whether these four distinct subtypes are associated with specific genomic alterations was tested. Using the criteria established by George et al. for functional significance, the mutational landscape across the four subtypes was examined (FIGS. 9A-D) and no significant differences in frequency between subtypes was observed (George et al., 2015). Additional observations from the RPPA analysis including little variation with respect to p53 expression across subtypes (FIG. 8E), in line with the similar mutational frequencies of TP53.

These investigators also reported several commonly amplified genes (MYC, MYCL1, MYCN, FGFR1, and IRS2) (George et al., 2015). While this copy number information is unavailable, gene expression values for these genes was used as a proxy for CNV (FIG. 2F). The majority of these genes show no variation in expression across subtypes, with the exception that MYC expression is significantly higher in the SCLC-P subtype (FIG. 2G), suggesting that MYC-amplifications may preferentially associate with SCLC-P. With respect to commonly deleted (FHIT, CDKN2A, RB1, and TP53) genomic loci (George et al., 2015), little subtype-specific variation in gene expression of these was observed (FIG. 2H). However, despite similar gene expression, RPPA analysis of subtyped cell lines show a significantly higher frequency of intact RB1 protein expression in the SCLC-I subtype (FIG. 2I).

Figure 2J:
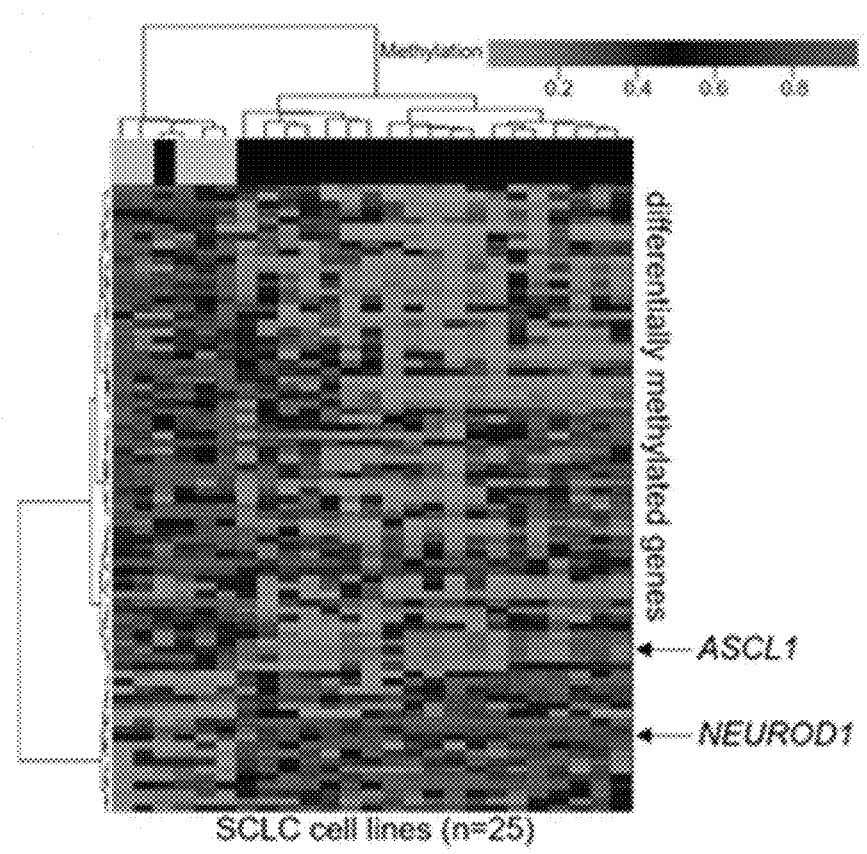
Figure 2K:
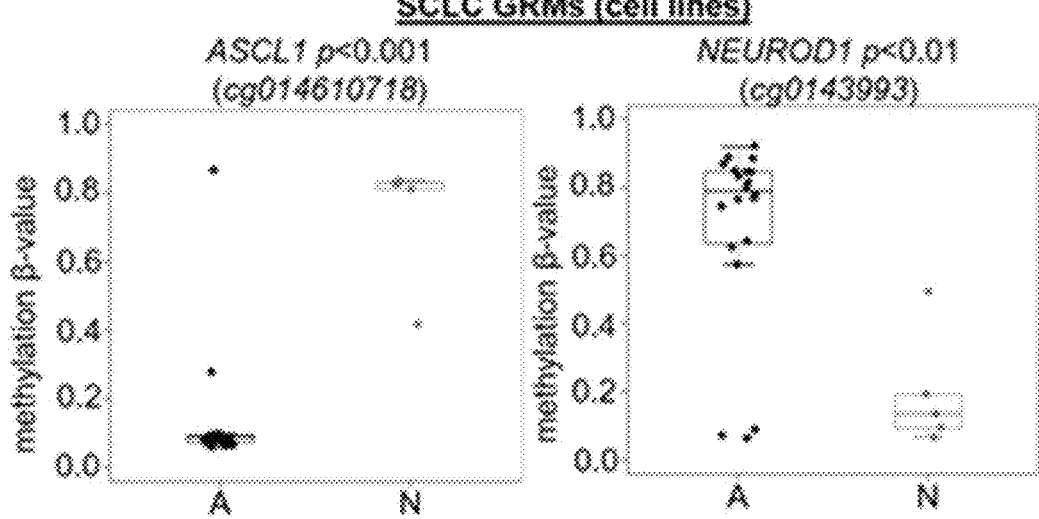

Since genomic distinctions do not drive subtype differences, whether epigenetic variations, such as promoter/gene methylation, may instead underlie these transcriptional differences was investigated. Evidence demonstrating the importance of epigenetic regulation of ASCL1, NEUROD1, and POU2F3 in SCLC or otherwise is scarce, although previous data have identified NEUROD1 methylation status as a potential biomarker in breast cancer (Fiegl et al., 2008) and ASCL1 methylation status as a predictor of ASCL1 expression in some pulmonary neuroendocrine tumors (Truong et al., 2017). Methylation array analysis was performed on 28 SCLC cell lines and identified genes regulated by methylation (GRMs) with differential methylation patterns between SCLC-A and SCLC-N(FIG. 2J). Notably, multiple sites in ASCL1 and NEUROD1 themselves show differential methylation between these subtypes (as in FIG. 2K). SCLC-A and SCLC-N can be easily distinguished by a robust methylation signature, or simply the methylation status of ASCL1 and NEUROD1, supporting the hypothesis that epigenetic mechanisms may underlie subtype.

Thus, a phenotypic portrait of each subtype emerges from the coalescence of genomic, transcriptomic, and proteomic data across multiple cohorts. SCLC-A is a neuroendocrine, epithelial subtype characteristic of what was once considered prototypical TTF1-positive SCLC. While still highly neuroendocrine, SCLC-N largely lacks TTF1 expression. Meanwhile, non-NE SCLC seems to consist of a mix of SCLC-P and SCLC-I, which can be further subdivided on the basis of EMT and, possibly, functional RB1 protein expression.

Example 3— SCLC-I is a Novel, Inflamed SCLC Subtype

In SCLC, responses to immune checkpoint blockade (ICB) are rare, which has been attributed to absent human leukocyte antigen (HLA) protein, low expression of interferon signatures and immune checkpoints, and scant cyto-
toxic T-cell infiltration (Hamilton & Rath, 2019). The
expression of both CD8A and CD8B, which encode the CD8
antigen specific to CD8+ cytotoxic T-cells, is significantly
higher in SCLC-I, suggesting greater cytotoxic T-cell infil-
tration in these tumors (FIG. 3A). Genes encoding HLAs
and other critical proteins for antigen presentation are
expressed at significantly higher levels in SCLC-I tumors
(FIG. 3B). An 18-gene interferon-γ-related T-cell gene
expression profile (GEP) (Ayer et al., 2017), which predicts
response to ICB independent of tumor mutational burden
(TMB) (Ott et al., 2019), was compared between the four
subtypes and revealed SCLC-I tumors consistently had the
highest expression of these genes (FIG. 3C). While complete
whole genome or exome DNA sequencing data were
unavailable for these SCLC tumors in order to calculate a
precise TMB, the proportion of mutated genes among the
total genes was used as a proxy and no significant variation
in this feature was observed across the subtypes (FIG. 10A).
This suggests that the inflamed phenotype, and potential
ICB vulnerability, of SCLC-I may be independent of TMB.
SCLC-I tumors have higher expression of numerous
immune checkpoints, including CD274, which encodes Pro-
grammed Death Ligand 1 (PD-L1), as well as PDCD1,
which encodes its receptor Programmed Cell Death Protein
1 (PD-1) (FIGS. 3D, 10B). The same is true for CD80 and
CD86, which encode the ligands for Cytotoxic T-lympho-
cyte-associated protein 4 (CTLA4), and CTLA4 itself
(FIGS. 3C-D, 10C). Other targetable immune checkpoints
more highly expressed in SCLC-I include CD38, IDO1,
TIGIT, C10orf54 (VISTA), ICOS, and LAG3 (FIG. 3E,
10D-H). Additionally, Stimulator of Interferon Genes
(STING)-induced T-cell attractant chemokines CCL5 and
CXCL10 are more highly expressed in SCLC-I, again sup-
porting an inflamed microenvironment prone to ICB
response (FIG. 3F-G) (Kitajima et al., 2019; Pantelidou et
al., 2019; Parkes et al., 2017; Sen et al., 2019).

Example 4— Unique Therapeutic Vulnerabilities
Across Subtypes

While there are biological differences between each sub-
type, it not known to what extent these differences yield
distinct responses to anti-cancer therapies. To investigate
subtype-specific vulnerabilities, SCLC cell line in vitro drug
response data for over 500 drugs were used (Gay, 2019;
Polley et al., 2016). For cisplatin, the backbone of the
standard of care for SCLC, a trend toward SCLC-P models
as the most sensitive (p=0.06) was observed, while SCLC-N
and SCLC-I models were resistant to cisplatin and SCLC-A
models experienced a range of sensitivities (FIG. 11A). For
each subtype, a drug or drug class that worked especially
well was identified, often accompanied by differential
expression of the drug target or putative predictive bio-
marker.

The SCLC-P subtype was significantly more sensitive to
all five PARP inhibitors (PARPi) tested in these data sets
(FIGS. 4A, 4B, 4D). While previous reports have identified
the expression of SLFN11 as a key predictor of PARPi
sensitivity in SCLC, it is notable that PARPi sensitivity
observed for the SCLC-P subgroup was accompanied by
only modest expression of SLFN11 (Allison Stewart et al.,
2017; Cardnell et al., 2017; Lok et al., 2017; Mural et al.,
2016; Pietanza et al., 2018), whereas most of the highest
SLFN11-expressing models are SCLC-A (FIG. 11B). Addi-
tionally, the SCLC-P subtype was consistently most sensi-
tive to anti-metabolites and nucleoside analogues, a novel putative vulnerability to classes of drugs not commonly
employed for SCLC (Table 1; FIG. 4A).

TABLE 1

| Additional selected drugs for which SCLC-P are most vulnerable. | |
| --- | --- |
| Drug | ANOVA p-value |
| Fludarabine | <0.001 |
| Pemetrexed | <0.001 |
| Cytarabine | <0.001 |
| 5-fluorouracil | <0.01 |
| Methotrexate | 0.04 |
| Clofarabine | 0.04 |
| Pralatrexate | 0.05 |
| Floxuridine | 0.05 |

SCLC-N tumor models are highly sensitive to multiple
AURK inhibitors (AURKi) (FIGS. 4A, 4E). Prior preclinical
and retrospective clinical data have identified cMYC protein
expression as a predictive biomarker for AURKi sensitivity
(Cardnell et al., 2017; Mollaoglu et al., 2017; Gay et al.,
2019; Owonikoko et al., 2017). Accordingly, SCLC-N cell
lines have robust expression of cMYC (FIG. 11C). As
expected, SCLC-P cell lines are also similarly sensitive to
AURKi (FIG. 4C).

Meanwhile, SCLC-A models are sensitive to multiple
B-cell lymphoma 2 (BCL2) inhibitors (BCL2i) (FIGS. 4A,
4F). Expression of BCL2 protein is a known correlate of
BCL2i sensitivity in SCLC (Cardnell et al., 2017; Gay et al.,
2019; Lochmann et al., 2018) and many of the cell lines with
the highest BCL2 expression are among the SCLC-A sub-
type (FIG. 11D). SCLC-A is the largest subgroup and
SCLC-A cell lines demonstrate a range of, or even bimodal
expression of, established predictive biomarkers (e.g.
SLFN11; FIG. 11B). Thus, additional second-order bio-
marker analysis beyond binary consideration of ASCL1 may
be required to identify further candidates in this subtype. By
way of example, among SCLC-A, cell lines that are SCLC-
A/SLFN11-positive were found to be sensitive to various
drugs in comparison to SCLC-A/SLFN11-negative cell lines
(FIG. 17).

ICBs are predicted to be most effective in SCLC-I, but
this cannot be accurately assessed in vitro. Interestingly,
another target commonly associated with immune cells,
Bruton's tyrosine kinase (BTK), is highly expressed among
SCLC-I tumors (FIG. 11E). Accordingly, this subtype was
the most sensitive to the BTK inhibitor ibrutinib (FIGS. 4G,
11F). BTK inhibitors are approved for several hematologic
malignancies but have not been previously explored as a
target in SCLC.

In addition to differential vulnerabilities to chemothera-
pies and small molecule inhibitors, it was hypothesized that
SCLC subtypes may possess unique expression patterns of
cell surface proteins (i.e. the surfaceome), as previously
exemplified by the high expression of numerous genes
encoding immune checkpoints. As with these immune
checkpoints, these candidates may be overlooked when
considering SCLC as a homogeneous disease, but uncovered
when querying on a subtype-specific basis. While small
molecule inhibition of these proteins may be pharmacologi-
cally challenging or inefficacious, they could prove ame-
nable to immune-based therapies, including chimeric anti-
gen receptor (CAR) and antibody-drug conjugate (ADC)
strategies. The inhibitory Notch ligand Delta-like ligand 3
(DLL3), for instance, was previously identified as highly
expressed in SCLC and other neuroendocrine tumors, and
was the target for the ADC rovalpituzumab tesirine (Rova- T), which was explored in a Phase II clinical trial for SCLC. While the trial demonstrated only modest activity, as well as unexpected toxicity of the conjugated cytotoxic molecule, DLL3 remains a target of interest with CAR T-cell and bispecific T-cell engager (BiTE) products in development. DLL3 protein was found to be significantly more highly expressed in SCLC-A tumors and virtually unexpressed in SCLC-P and -I tumors (FIG. 11G), again suggesting that SCLC subtype may predict a subtype-specific surfaceome for patient selection and target discovery. Indeed, across all three transcriptional data sets, DLL3 was consistently most highly expressed in SCLC-A and lowest in SCLC-P and -I (FIGS. 11H-J).

Example 5— Clinical Features of SCLC Subtypes

Basic clinical data for the patients from the NMF analysis are available (PMID: 26168399). Relapse-free and overall survival data was available for 67 of these patients and there were no significant differences in relapse-free (FIG. 12A) or overall survival (FIG. 12B). Demographic information such as age at diagnosis (FIG. 12C), mean total pack-years of smoking (FIG. 12D), and sex (FIG. 12E) were also not significantly different among the groups. The majority of these tumors were from early stage patients who underwent surgical resection and very few are from extensive-stage patients. The survival values observed exceed those typically seen for SCLC (Byers & Rudin, 2015) due to the bias toward very early stage disease, as the tumors included in this cohort are not representative of the SCLC population on-the-whole. The few extensive-stage patients were among the SCLC-A and SCLC-N subtypes, but there was no significant difference in frequency of non-limited stage status (FIG. 12F). Further investigation in ES-SCLC treated systemically is certainly warranted to delve into differences in prognosis and responses to specific therapies.

Example 6— Intratumoral Heterogeneity of SCLC Subtypes

The prior analyses reveal the potential impact of comprehensive characterization of intertumoral heterogeneity among SCLCs. However, these data sets lack the resolution to discern whether intratumoral heterogeneity exists among these subtypes. Using monoclonal antibodies for ASCL1, NEUROD1, and POU2F3 protein, immunohistochemistry was performed on three consecutive sections of 14 SCLC tumors and scored each for the fraction of tumor nuclei which stained positive for each protein, as well as the intensity (as measured by percentage of tumor nuclei multiplied by intensity on 0-3 scale, or H-score) (Table 2). This analysis revealed instances of tumors that represented a single subtype, as in tumors #3 (SCLC-A), 10 (SCLC-N), 11 (SCLC-P), and 7 (SCLC-I) (FIGS. 5A, 5B). However, even these tumors have small, but detectable populations of cells expressing at least low levels of the other transcription factors. Others have made similar observations regarding this apparent intratumoral heterogeneity (Simpson et al., 2020). In rare cases, the tumors appear truly mixed, with evidence that multiple subtypes are present in substantial proportions within a single tumor—consider tumor #5, which demonstrates a roughly 70/30 proportion of ASCL1/NEUROD1 positivity. Interestingly, the ASCL1 and NEUROD1 expressing cells are found in geographically distinct nests (FIG. 5C). Thus, intratumoral heterogeneity can exist, raising the possibility that these subtypes may represent a spectrum or continuum and that intratumoral subtype heterogeneity or subtype switching may underlie key elements of the biology and natural history of SCLC. Indeed, recent studies using SCLC GEMMs suggest that individual tumor cells undergo temporal evolution from one transcription-factor defined subtype to another (Ireland et al., 2020).

To validate the immunohistochemistry findings, single-cell RNAseq was used. A series of circulating tumor cell (CTC)-derived xenograft (CDX) models were derived from SCLC patients (Stewart et al., 2018; Stewart et al., 2019; Stewart et al., 2020b), including patients awaiting/receiving frontline therapy (MDA-SC4, MDA-SC39, MDA-SC68, and MDA-SC75) and patients whose disease has relapsed (MDA-SC16, MDA-SC49, and MDA-SC55). These models have been extensively validated to ensure recapitulation of the original patient's molecular and clinical response characteristics (Stewart et al., 2018; Stewart et al., 2020b). Tumors from these models were dissociated into single-cell suspensions and subjected to 10×Genomics single-cell RNAseq with subsequent filtering steps selecting 2,000 cells for each model (Stewart et al., 2019; Stewart et al., 2020b). Based on single-cell expression of ASCL1, NEUROD1, and POU2F3, both SCLC-A and SCLC-N predominant models were found within the xenograft library (Table 3). Six of these models were SCLC-A and one was SCLC-N(FIG. 5H). POU2F3 was not appreciably detected in any of the models. t-Distributed Stochastic Neighbor Embedding (t-SNE) feature plots illustrate the presence or absence of single-cell expression of ASCL1 and NEUROD1, along with cells that are considered triple-negative (as in SCLC-I) (examples in FIG. 5D, 5E). These plots underscore that even in clearly ASCL1-predominant (FIG. 5D) or NEUROD1-predominant (FIG. 5E) xenograft tumors, there is modest intratumoral heterogeneity with respect to subtype on a cell-by-cell basis.

Relapsed models possessed significantly higher fractions of triple negative cells (FIG. 5G). Using t-SNE feature plots for the treatment-naïve, cisplatin-sensitive MDA-SC68 parental model, virtually ubiquitous ASCL1 expression and negligible presence of triple negative cells was observed (FIG. 5I). DLL3/DLL3 is an inhibitory Notch ligand and transcriptional target of ASCL1 that is highly expressed in SCLC-A cell lines along with inverse expression of NOTCH1/2 (FIGS. 11G, 5M, 5N). DLL3, also a putative therapeutic target in SCLC, is also robustly expressed in MDA-SC68 (FIG. 5J). If instead the MDA-SC68rel model, which is relapsed after in vivo cisplatin treatment and now cisplatin-resistant, is considered, ASCL1 expression has decreased with formerly ASCL1+ cells now replaced by triple negative cells (FIG. 5K)— consistent with the earlier observation about increasing triple negative populations in relapsed tumors. Accordingly, the expression of DLL3 is diminished in MDA-SC68rel relative to MDA-SC68, in particular among the newly triple negative cells (FIG. 5L). This simple demonstration of shifts from SCLC-A to SCLC-I illustrates the impact this phenomenon can exert over the expression of desired therapeutic target, as in DLL3 (Rudin et al., 2017).

Figure 15:
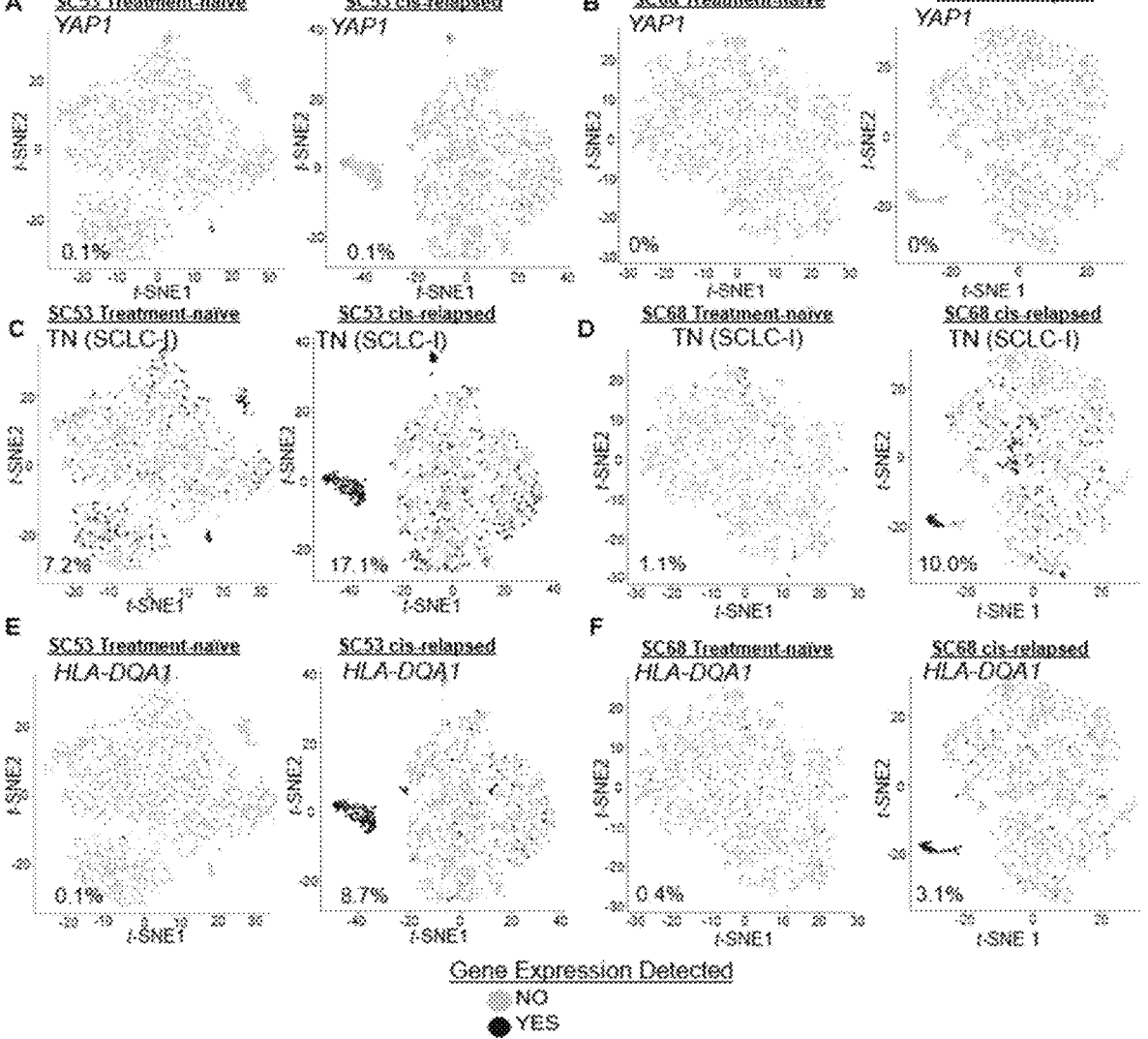

Single-cell RNAseq also permits exploration of co-expression of subtype-defining transcription factors with single-cell resolution. Each cell can be classified into one of seven categories on the basis of the binary presence/absence of ASCL1, NEUROD1, and POU2F3 expression (and co-expression) (Table 3). While most cells express only one of the transcription factors, the expression is not entirely mutually exclusive. While fewer than 1% of cells in any of the models expressed POU2F3, these rare POU2F3-positive cells all exhibit co-expression of ASCL1. Furthermore, in MDA-SC39, nearly 10% of the cells express both ASCL1 and NEUROD1, although this fraction is much lower in other tumors. While bulk analyses showed that ASCL1 and NEURON may be sometimes co-expressed in the same tumor (examples in FIGS. 1C-E) and that this may occur in a mutually exclusive pattern (as in FIG. 5C), these data demonstrate that such co-expression can occur at the single-cell level. In light of this, it was considered that epigenetic regulation might govern a continuum of expression ranging from ASCL1-only to NEUROD1-only, with co-expression representing a transition state. SCLC cell lines were classified as ASCL1-only, NEUROD1-only, or "both" on the basis of gene expression. Using publicly available methylation data, it was observed that these three classifications can be discriminated by the methylation beta-values of the region upstream of the NEUROD1 transcriptional start site (TSS) (FIGS. 5F, 13A-B). Specifically, ASCL1-only cell lines have relatively high methylation of sites both proximal and more distal to the NEURON TSS, while NEUROD1-only cell lines have virtually no methylation of proximal and little methylation of more distal sites. Cell lines classified as "both" demonstrate low methylation of proximal sites but methylation of more distal sites nearly as high as the ASCL1-only cell lines.

resent a novel mechanism underlying platinum resistance. Two platinum-sensitive, ASCL1-predominant CDX models developed from treatment-naïve patients (MDA-SC53 and MDA-SC68) were selected. These models were treated with cisplatin to maximal response and then throughout relapse ("cis-relapsed") and collected for single-cell RNAseq along with a matched vehicle treated tumor of same size ("treatment-naïve") (FIG. 14 and (Stewart et al., 2020b)). Using t-SNE feature plots, the presence or absence of expression of ASCL1 between the parental treatment-naïve model and the cis-relapsed model were compared and, in both cases, a reduction in ASCL1-positive proportion was observed (FIGS. 6A-B) and the emergence of a distinct "island" cluster (highlighted by rectangle, FIGS. 6A-B). In both cases, this cluster contains a majority of the ASCL1-negative cells that emerge post-relapse. A closer view of this cluster (FIGS. 6C-D), highlights that the ASCL1-negative cells do not gain expression of NEUROD1, POU2F3, or even YAP1 (FIGS. 15A-B). Instead, this cluster contains

TABLE 2

Frequency and intensity of ASCL1/NEUROD1/POU2F3
expression in human SCLC tumors

| Tumor ID | % Nuclei ASCL1+ | ASCL1 H-score | % Nuclei NEUROD1+ | NEUROD1 H-score | % Nuclei POU2F3+ | POU2F3 H-score |
|---|---|---|---|---|---|---|
| 1 | 42.55 | 67.25 | 82.66 | 199.14 | 17.85 | 48.02 |
| 2 | 72.74 | 154.98 | 7.70 | 12.02 | 8.32 | 23.93 |
| 3 | 86.20 | 187.78 | 0.13 | 0.24 | 0.04 | 1.04 |
| 4 | 76.08 | 154.33 | 43.49 | 96.47 | 1.34 | 3.52 |
| 5 | 72.64 | 176.55 | 32.79 | 80.23 | 0.54 | 1.55 |
| 6 | 2.68 | 2.89 | 0.55 | 1.41 | 57.57 | 150.87 |
| 7 | 12.16 | 12.66 | 0.21 | 0.40 | 0.52 | 1.49 |
| 8 | 82.63 | 183.79 | 53.66 | 107.01 | 1.02 | 2.92 |
| 9 | 71.26 | 116.52 | 9.21 | 21.71 | 0.96 | 2.74 |
| 10 | 36.26 | 42.90 | 87.19 | 226.72 | 1.49 | 4.18 |
| 11 | 5.50 | 5.58 | 0.05 | 0.10 | 85.64 | 229.74 |
| 12 | 90.67 | 187.39 | 1.07 | 1.18 | 2.72 | 7.61 |
| 13 | 67.06 | 99.76 | 12.08 | 19.06 | 0.86 | 2.44 |
| 14 | 58.22 | 119.07 | 34.83 | 59.82 | 0.99 | 2.87 |

TABLE 3

Single-cell expression of ASCL1/NEUROD1/POU2F3 in patient-derived SCLC xenografts

| Model | A–N–P– | A–N–P+ | A–N+P– | A–N+P+ | A+N–P– | A+N–P+ | A+N+P– | A+N+P+ |
|---|---|---|---|---|---|---|---|---|
| | | | Frontline | | | | | |
| SC4 | 3.85% | 0 | 0 | 0 | 95.80% | 0 | 0.35% | 0 |
| SC39 | 1.60% | 0 | 0 | 0 | 88.70% | 0 | 9.70% | 0 |
| SC53 | 7.20% | 0 | 0.40% | 0 | 92.00% | 0.10% | 0.30% | 0 |
| SC68 | 1.15% | 0 | 0 | 0 | 98.85% | 0 | 0 | 0 |
| SC75 | 5.60% | 0 | 0 | 0 | 93.95% | 0 | 0.45% | 0 |
| | | | Relapsed | | | | | |
| SC16 | 6.95% | 0 | 0 | 0 | 88.25% | 0 | 4.65% | 0 |
| SC49 | 9.90% | 0 | 89.45% | 0 | 0 | 0 | 0.55% | 0 |
| SC53rel | 17.10% | 0 | 0.85% | 0 | 80.80% | 0.10% | 1.20% | 0 |
| SC55 | 6.45% | 0 | 0.65% | 0 | 89.30% | 0.65% | 2.95% | 0 |
| SC68CR | 10.00% | 0 | 0 | 0 | 89.45% | 0 | 0.55% | 0 |

Example 7— Emergence of SCLC-I Populations Accompanies Platinum Resistance

In the single-cell RNAseq data, a significant trend toward increased triple negative (i.e. SCLC-I) cells in platinum-relapsed models was identified (FIG. 5G). As SCLC-I represents a highly platinum-resistant subtype, it was reasoned that intratumoral shifts toward increasing SCLC-I may rep-cells that are largely triple negative (SCLC-I) (FIGS. 15C-D). Not only are the cells in this cluster reminiscent of SCLC-I due to their triple negative status, but they are distinctly mesenchymal based on EMT score, relative to their peers (FIGS. 6E-F)—again typical of SCLC-I cells. Furthermore, while cells from treatment-naïve models express are almost universally negative for expression of HLAs, as expected for SCLC-A cells, those from the cis-relapsed model consistently gain expression of MHC class II genes, including HLA-DRB1 and HLA-DQA1 (FIGS. 6G-H, 15E-F). As predicted, the expression of HLA genes is restricted to cells in the triple-negative, SCLC-I island cluster.

Figure 16:
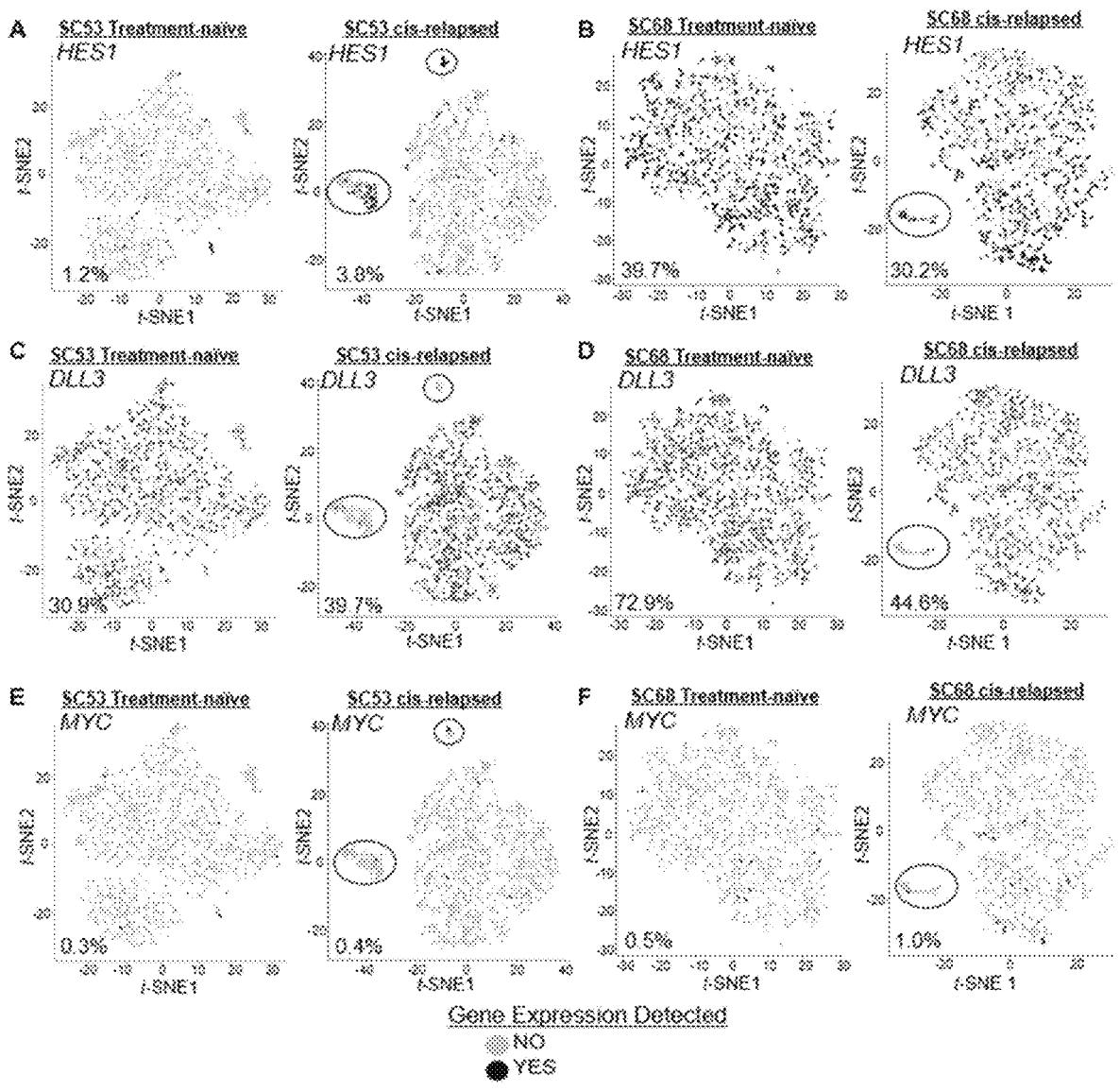

Prior studies have proposed that Notch activation is capable of mediating a switch between neuroendocrine and non-neuroendocrine SCLC cell fates (Ireland et al., 2020; Lim et al., 2017), similar to that observed in SCLC-A to SCLC-I. Expression of the Notch pathway transcriptional target HES1 was compared between treatment-naïve and cis-relapsed pairs as a proxy for Notch activation. In MDA-SC53, a modest increase in HES1 expression, indicating Notch activation, was seen following relapse, although this expression was highly restricted to regions populated by SCLC-I cells (FIGS. 16A, 15C). While in MDA-SC68, HES1 expression is modestly reduced following relapse, although the SCLC-I cluster maintains significant HES1 expression (FIG. 16B). The Notch inhibitory ligand, and putative SCLC target, DLL3 demonstrates precisely the inverse, as expected for a molecule that reduces Notch activation. In both MDA-SC53 and MDA-SC68, DLL3 expression is essentially absent in SCLC-I clusters (FIGS. 16C-D), although overall DLL3 is modestly increased post-relapse in MDA-SC53 and markedly decreased in MDA-SC68. These fluctuations in Notch targets and inhibitors are consistent with prior data highlighting the role of Notch signaling in SCLC phenotypic switching. While one recent study identified MYC activation as a critical initiator of this process, our models demonstrated minimal MYC, MYCL, or MYCN expression in regions populated by SCLC-I (FIGS. 16E-F).

Together, these single-cell analyses suggest that cisplatin resistance coincides with the emergence of a cluster of cells that typify the SCLC-I subtype, apparently derived from cells originally SCLC-A that have undergone subtype switching associated with fluctuations in Notch pathway activation.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Allison Stewart et al., "Dynamic variations in epithelial-to-mesenchymal transition (EMT), ATM, and SLFN11 govern response to PARP inhibitors and cisplatin in small cell lung cancer," Oncotarget, 8:28575-28587, 2017.

Antonia et al. Nivolumab alone and nivolumab plus ipilimumab in recurrent small-cell lung cancer (CheckMate 032): a multicentre, open-label, phase ½ trial. Lancet Oncol 17, 883-895, (2016).

Ayers, M. et al. IFN-gamma-related mRNA profile predicts clinical response to PD-1 blockade. J Clin Invest 127, 2930-2940, (2017).

Bonnafous et al., Abstract 5037: Targeting MICA with therapeutic antibodies for the treatment of cancer. Journal for Immuno Therapy of Cancer, 1:P41 (2013).

Borromeo, M. D. et al. ASCL1 and NEUROD1 Reveal Heterogeneity in Pulmonary Neuroendocrine Tumors and Regulate Distinct Genetic Programs. Cell Rep 16, 1259-1272, (2016).

Bottger, F. et al. Tumor Heterogeneity Underlies Differential Cisplatin Sensitivity in Mouse Models of Small-Cell Lung Cancer. Cell Rep 27, 3345-3358 e3344, (2019).

Butler, A., Hoffman, P., Smibert, P., Papalexi, E. & Satija, R. Integrating single-cell transcriptomic data across different conditions, technologies, and species. Nat Biotechnol 36, 411-420, (2018).

Byers, L. A. & Rudin, C. M. Small cell lung cancer: where do we go from here? Cancer 121, 664-672, (2015).

Byers, L. A. et al. An epithelial-mesenchymal transition gene signature predicts resistance to EGFR and PI3K inhibitors and identifies Axl as a therapeutic target for overcoming EGFR inhibitor resistance. Clin Cancer Res 19, 279-290, (2013).

Byers et al., "Proteomic profiling identifies dysregulated pathways in small cell lung cancer and novel therapeutic targets including PARP1," Cancer Discov., 2:798-811, 2012.

Canadas, I., Thummalapalli, R., Kim, J. W., Kitajima, S., Jenkins, R. W., Christensen, C. L., Campisi, M., Kuang, Y., Zhang, Y., Gjini, E., et al. (2018). Tumor innate immunity primed by specific interferon-stimulated endogenous retroviruses. Nat Med 24, 1143-1150.

Cardnell, R. J. et al. Protein expression of TTF1 and cMYC define distinct molecular subgroups of small cell lung cancer with unique vulnerabilities to aurora kinase inhibition, DLL3 targeting, and other targeted therapies. Oncotarget 8, 73419-73432, (2017).

Carney, D. N. et al. Establishment and identification of small cell lung cancer cell lines having classic and variant features. Cancer Res 45, 2913-2923 (1985).

Chalishazar, M. D. et al. MYC-Driven Small-Cell Lung Cancer is Metabolically Distinct and Vulnerable to Arginine Depletion. Clin Cancer Res 25, 5107-5121, (2019).

Chung H. C., L.-M. J. A., Kao S. C., Miller W. H., Ros W., Gao B., Marabelle A., Gottfried M., Zer A., Delord J., Penel N., Jalal S. I., Xu L., Zeigenfuss S., Pruitt S. K., Piha-Paul S. A. in ASCO Annual Meeting. 8506 (2018).

Chung, H. C., Piha-Paul, S. A., Lopez-Martin, J., Schellens, J. H. M., Kao, S., Miller, W. H., Jr., Delord, J. P., Gao, B., Planchard, D., Gottfried, M., et al. (2020). Pembrolizumab After Two or More Lines of Previous Therapy in Patients With Recurrent or Metastatic SCLC: Results From the KEYNOTE-028 and KEYNOTE-158 Studies. J Thorac Oncol 15, 618-627.

Das, M. (2017). Labetuzumab govitecan in metastatic colorectal cancer. Lancet Oncol 18, e563.

Dotan, E., Cohen, S. J., Starodub, A. N., Lieu, C. H., Messersmith, W. A., Simpson, P. S., Guarino, M. J., Marshall, J. L., Goldberg, R. M., Hecht, J. R., et al. (2017). Phase I/II Trial of Labetuzumab Govitecan (Anti-CEACAM5/SN-38 Antibody-Drug Conjugate) in Patients

41

With Refractory or Relapsing Metastatic Colorectal Cancer. J Clin Oncol 35, 3338-3346.

Farago, A. F. et al. Combination Olaparib and Temozolomide in Relapsed Small Cell Lung Cancer. Cancer Discov, (2019).

Fiegl, H. et al. Methylated NEUROD1 promoter is a marker for chemosensitivity in breast cancer. Clin Cancer Res 14, 3494-3502, (2008).

Gazdar, A. F., Carney, D. N., Nau, M. M. & Minna, J. D. Characterization of variant subclasses of cell lines derived from small cell lung cancer having distinctive biochemical, morphological, and growth properties. Cancer Res 45, 2924-2930 (1985).

Gay, C. M. et al. Differential Sensitivity Analysis for Resistant Malignancies (DISARM) Identifies Common Candidate Therapies across Platinum-Resistant Cancers. Clin Cancer Res 25, 346-357, (2019).

Gay C M, D. L., Stewart C A, Xi Y, Cardnell R J, Swisher S G, Roth J A, Glisson B S, Wang J, Heymach J V & Byers L A (2019). ASCL1, NEUROD1, and POU2F3 drive distinct subtypes of small cell lung cancer with unique therapeutic vulnerabilities. Paper presented at: Interational Association for the Study of Lung Cancer World Conference on Lung Cancer (Barcelona, Spain).

George et al., "Comprehensive genomic profiles of small cell lung cancer," Nature, 524:47-53, 2015.

Hamilton, G. & Rath, B. Immunotherapy for small cell lung cancer: mechanisms of resistance. Expert Opin Biol Ther 19, 423-432, (2019).

Hellmann, M. D. et al. Tumor Mutational Burden and Efficacy of Nivolumab Monotherapy and in Combination with Ipilimumab in Small-Cell Lung Cancer. Cancer Cell 33, 853-861 e854, (2018).

Hodgkinson, C. L. et al. Tumorigenicity and genetic profiling of circulating tumor cells in small-cell lung cancer. Nat Med 20, 897-903, (2014).

Horn, L. et al. First-Line Atezolizumab plus Chemotherapy in Extensive-Stage Small-Cell Lung Cancer. N Engl J Med 379, 2220-2229, (2018).

Huang, Y. H. et al. POU2F3 is a master regulator of a tuft cell-like variant of small cell lung cancer. Genes Dev 32, 915-928, (2018).

Ireland, A. S., Micinski, A. M., Kastner, D. W., Guo, B., Wait, S. J., Spainhower, K. B., Conley, C. C., Chen, O. S., Guthrie, M. R., Soltero, D., et al. (2020). MYC Drives Temporal Evolution of Small Cell Lung Cancer Subtypes by Reprogramming Neuroendocrine Fate. Cancer Cell.

Kitajima, S. et al. Suppression of STING Associated with LKB1 Loss in KRAS-Driven Lung Cancer. Cancer Discov 9, 34-45, (2019).

Lim, J. S., Ibaseta, A., Fischer, M. M., Cancilla, B., O'Young, G., Cristea, S., Luca, V. C., Yang, D., Jahchan, N. S., Hamard, C., et al. (2017). Intratumoural heterogeneity generated by Notch signalling promotes small-cell lung cancer. Nature 545, 360-364.

Lin, S. H. et al. Genes suppressed by DNA methylation in non-small cell lung cancer reveal the epigenetics of epithelial-mesenchymal transition. BMC Genomics 15, 1079, (2014).

Lochmann, T. L. et al. Venetoclax Is Effective in Small-Cell Lung Cancers with High BCL-2 Expression. Clin Cancer Res 24, 360-369, (2018).

Lok, B. H. et al. PARP Inhibitor Activity Correlates with SLFN11 Expression and Demonstrates Synergy with Temozolomide in Small Cell Lung Cancer. Clin Cancer Res 23, 523-535, (2017).

Mak, M. P. et al. A Patient-Derived, Pan-Cancer EMT Signature Identifies Global Molecular Alterations and Immune Target Enrichment Following Epithelial-to-Mesenchymal Transition. Clin Cancer Res 22, 609-620, (2016).

Mollaoglu, G. et al. MYC Drives Progression of Small Cell Lung Cancer to a Variant Neuroendocrine Subtype with Vulnerability to Aurora Kinase Inhibition. Cancer Cell 31, 270-285, (2017).

Mural, J. et al. Resistance to PARP inhibitors by SLFN11 inactivation can be overcome by ATR inhibition. Oncotarget 7, 76534-76550, (2016).

Ott, P. A. et al. T-Cell-Inflamed Gene-Expression Profile, Programmed Death Ligand 1 Expression, and Tumor Mutational Burden Predict Efficacy in Patients Treated With Pembrolizumab Across 20 Cancers: KEYNOTE-028. J Clin Oncol 37, 318-327, (2019).

Owonikoko, T. et al. OA05.05 Randomized Phase 2 Study: Alisertib (MLN8237) or Placebo+Paclitaxel as Second-Line Therapy for Small-Cell Lung Cancer (SCLC). Journal of Thoracic Oncology 12, S261-S262, (2017).

Pantelidou, C. et al. PARP Inhibitor Efficacy Depends on CD8(+) T-cell Recruitment via Intratumoral STING Pathway Activation in BRCA-Deficient Models of Triple-Negative Breast Cancer. Cancer Discov 9, 722-737, (2019).

Parkes, E. E. et al. Activation of STING-Dependent Innate Immune Signaling By S-Phase-Specific DNA Damage in Breast Cancer. J Natl Cancer Inst 109, (2017).

Paz-Ares, L., Dvorkin, M., Chen, Y., Reinmuth, N., Hotta, K., Trukhin, D., Statsenko, G., Hochmair, M. J., Ozguroglu, M., Ji, J. H., et al. (2019). Durvalumab plus platinum-etoposide versus platinum-etoposide in first-line treatment of extensive-stage small-cell lung cancer (CASPIAN): a randomised, controlled, open-label, phase 3 trial. Lancet 394, 1929-1939.

Pietanza, M. C. et al. Randomized, Double-Blind, Phase II Study of Temozolomide in Combination With Either Veliparib or Placebo in Patients With Relapsed-Sensitive or Refractory Small-Cell Lung Cancer. J Clin Oncol 36, 2386-2394, (2018).

Polley et al., "Small Cell Lung Cancer Screen of Oncology Drugs, Investigational Agents, and Gene and microRNA Expression," 108:djw122, 2016.

Reck M., V. D., Ciuleanu T., Gettinger S., Peters S., Horn L., Audigier-Valette C., Pardo N., Juan-Vidal O., Cheng Y., Zhang H., Shi M., Wolf J., Antonia S. J., Nakagawa K., Selvaggi G., Baudelet C., Chang H., Spigel D. R. in ESMO Immuno-Oncology Congress. x39-x43 (2018).

Rudin et al., "Molecular subtypes of small cell lung cancer: a synthesis of human and mouse model data," Nat. Rev. Clin. Oncol., 19:289-297, 2019.

Rudin, C. M. et al. Rovalpituzumab tesirine, a DLL3-targeted antibody-drug conjugate, in recurrent small-cell lung cancer: a first-in-human, first-in-class, open-label, phase 1 study. Lancet Oncol 18, 42-51, (2017).

Sato et al., "PRC2 overexpression and PRC2-target gene repression relating to poorer prognosis in small cell lung cancer," Sci Rep. 3:1911, 2013.

Sen et al., "Targeting DNA damage repair in small cell lung cancer and the biomarker landscape," Transl Lung Cancer Res., 7:50-68, 2018.

Sharkey, R. M., Govindan, S. V., Cardillo, T. M., Donnell, J., Xia, J., Rossi, E. A., Chang, C. H., and Goldenberg, D. M. (2018). Selective and Concentrated Accretion of SN-38

43 44 with a CEACAM5-Targeting Antibody-Drug Conjugate (ADC), Labetuzumab Govitecan (IMMU-130). Mol Cancer Ther 17, 196-203.

Simpson, K. L., Stoney, R., Frese, K. K., Simms, N., Rowe, W., Pearce, S. P., Humphrey, S., Booth, L., Morgan, D., Dynowski, M., et al. (2020). A biobank of small cell lung cancer CDX models elucidates inter- and intratumoral phenotypic heterogeneity. Nature Cancer 1, 437-451.

Skoulidis, F., Byers, L. A., Diao, L., Papadimitrakopoulou, V. A., Tong, P., Izzo, J., Behrens, C., Kadara, H., Parra, E. R., Canales, J. R., et al. (2015). Co-occurring genomic alterations define major subsets of KRAS-mutant lung adenocarcinoma with distinct biology, immune profiles, and therapeutic vulnerabilities. Cancer Discov 5, 860-877.

Stewart C. A., G. C. M., Xi Y., Siva V., Fujimoto J., Tong P., Diao L., Li L., Bolisetty M., Kalhor N., Lawson P., Vasquez M., Tran H., Wistuba I. I., Glisson B., Zhang J., Swisher S. G., Roth J. A., Heymach J. V., Robson P., Wang J., Byers L. A. in AACR Annual Meeting (2018).

Stewart C. A., G. C. M., Xi Y., Fujimoto J., Hartsfield P M., Tran H., Fernandez L., Lu D., Wang Y., Dittamore R., Zhang J., Swisher S. G., Roth J. A., Oliver T. G., Heymach J. V., Wistuba I. I., Glisson B. S. Robson P., Wang J., Byers L. A. in AACR Annual Meeting 2019.

Thistlethwaite, F. C., Gilham, D. E., Guest, R. D., Rothwell, D. G., Pillai, M., Burt, D. J., Byatte, A. J., Kirillova, N., Valle, J. W., Sharma, S. K., et al. (2017). The clinical efficacy of first-generation carcinoembryonic antigen (CEACAM5)-specific CAR T cells is limited by poor persistence and transient pre-conditioning-dependent respiratory toxicity. Cancer Immunol Immunother 66, 1425-1436.

Truong, N., Chun, S. M., Kim, T. I., Suh, Y. A. & Jang, S. J. Hypermethylation of adjacent CpG sites is negatively correlated with the expression of lineage oncogene ASCL1 in pulmonary neuroendocrine tumors. Tumour Biol 39, 1010428317706225, (2017).

Whalen, K. A., White, B. H., Quinn, J. M., Kriksciukaite, K., Alargova, R., Au Yeung, T. P., Bazinet, P., Brockman, A., DuPont, M. M., Oller, H., et al. (2019). Targeting the Somatostatin Receptor 2 with the Miniaturized Drug Conjugate, PEN-221: A Potent and Novel Therapeutic for the Treatment of Small Cell Lung Cancer. Mol Cancer Ther 18, 1926-1936.

White, B. H., Whalen, K., Kriksciukaite, K., Alargova, R., Au Yeung, T., Bazinet, P., Brockman, A., DuPont, M., Oller, H., Lemelin, C. A., et al. (2019). Discovery of an SSTR2-Targeting Maytansinoid Conjugate (PEN-221) with Potent Activity in Vitro and in Vivo. J Med Chem 62, 2708-2719.

Zhang, W. et al. Small cell lung cancer tumors and preclinical models display heterogeneity of neuroendocrine phenotypes. Transl Lung Cancer Res 7, 32-49, (2018).

Zimmermann, S., Peters, S., Owinokoko, T. & Gadgeel, S. M. Immune Checkpoint Inhibitors in the Management of Lung Cancer. Am Soc Clin Oncol Educ Book 38, 682-695, (2018).

What is claimed is:

1. A method of treating a human patient having a small cell lung cancer, the method comprising
(a) obtaining a sample of the patient's cancer;
(b) measuring an expression level of ASCL1, NEUROD1, and POU2F3 in the sample or determining a methylation status of ASCL1, NEUROD1, and POU2F3 in the sample;

(c) classifying the patient's small cell lung cancer based on the expression level of ASCL1, NEUROD1, and POU2F3 in the sample or the methylation status of ASCL1, NEUROD1, and POU2F3 in the sample, and wherein:
(i) the patient is classified as sensitive to a BCL-2 inhibitor or DLL-3 targeting molecular when ASCL1 is expressed or ASCL1 is not methylated in the sample;
(ii) the patient is classified as sensitive to an Aurora kinase inhibitor when NEUROD1 is expressed or NEUROD1 is not methylated in the sample;
(iii) the patient is classified as sensitive to a PARP inhibitor, a nucleoside analogue, an anti-metabolite, or a platinum-containing chemotherapeutic agent when POU2F3 is expressed or POU2F3 is not methylated in the sample; or
(iv) the patient is classified as sensitive to a Bruton's tyrosine kinase (BTK) inhibitor when the sample is ASCL1, NEUROD1, and POU2F3 triple negative or ASCL1, NEUROD1, and POU2F3 are each methylated in the sample; and
(d) administering to the classified patient a therapeutically effective amount of a first anti-cancer therapy comprising:
(i) a BCL-2 inhibitor or DLL-3 targeting molecule, wherein ASCL1 is expressed or ASCL1 is not methylated in the sample;
(ii) an Aurora kinase inhibitor, wherein NEUROD1 is expressed or NEUROD1 is not methylated in the sample;
(iii) a PARP inhibitor, a nucleoside analogue, an anti-metabolite, or a platinum-containing chemotherapeutic agent, wherein POU2F3 is expressed or POU2F3 is not methylated in the sample; or
(iv) a Bruton's tyrosine kinase (BTK) inhibitor, wherein the sample is ASCL1, NEUROD1, and POU2F3 triple negative or ASCL1, NEUROD1, and POU2F3 are each methylated.

2. The method of claim 1, wherein the expression of a gene is measured by detecting a level of mRNA transcribed from the gene.

3. The method of claim 1, wherein the expression of a gene is measured by detecting a level of a polypeptide encoded by the gene.

4. The method of claim 1, wherein the sample is a formalin-fixed, paraffin-embedded sample or a fresh frozen sample.

5. The method of claim 1, further comprising performing the classification a second time.

6. The method of claim 5, wherein the second time is after the patient has developed resistance to the first anti-cancer therapy.

7. The method of claim 1, wherein the patient falls into two or more classifications, wherein the patient is administered a therapeutic agent for each classification.

8. A method of treating a human patient having a small cell lung cancer, the method comprising:
(a) obtaining a sample of the patient's cancer;
(b) measuring an expression level of ASCL1 and SLFN11 in the sample or determining a methylation status of ASCL1 in the sample;
(c) classifying the patient's small cell lung cancer based on the expression level of ASCL1 and SLFN11 in the sample or the methylation status of ASCL1 in the sample, wherein:

(i) the patient is classified as being sensitive to treatment with a PARP inhibitor, cisplatin, ATM inhibitor, ATR inhibitor, WEE1 inhibitor, mTOR inhibitor, a DLL3 targeting molecule, or a combination thereof when ASCL1 is expressed at an increased level as compared to an inflamed-subtype of small cell lung cancer (SCLC-I); or (ii) the patient is classified as being sensitive to treatment with a PARP inhibitor, cisplatin, ATM inhibitor, ATR inhibitor, WEE1 inhibitor, mTOR inhibitor, a DLL3 targeting molecule, or a combination thereof when ASCL1 is not methylated and SLFN11 is expressed at an increased level as compared to an inflamed-subtype of small cell lung cancer (SCLC-I); and (d) administering to the patient a therapeutically effective amount of a first anti-cancer therapy comprising a PARP inhibitor, cisplatin, ATM inhibitor, ATR inhibitor, WEE1 inhibitor, mTOR inhibitor, a DLL3 targeting molecule, or a combination thereof, wherein:

(i) ASCL1 is expressed at an increased level as compared to an inflamed-subtype of small cell lung cancer (SCLC-I); or (ii) ASCL1 is not methylated and SLFN11 is expressed at an increased level as compared to an inflamed-subtype of small cell lung cancer (SCLC-I).

9. The method of claim 8, wherein the ATM inhibitor is AZD0156, the ATR inhibitor is AZD6738, the WEE1 inhibitor is AZD1775, and/or the mTOR inhibitor is AZD2014.

* * * * *